(12) United States Patent
Johnson et al.

(10) Patent No.: US 11,593,715 B2
(45) Date of Patent: *Feb. 28, 2023

(54) METHODS FOR TRAINING AND USING A NEUROME THAT EMULATES THE BRAIN OF A USER

(71) Applicant: HI LLC, Los Angeles, CA (US)

(72) Inventors: Bryan Johnson, Culver City, CA (US); Ethan Pratt, Santa Clara, CA (US); Jamu Alford, Lake Arrowhead, CA (US); Husam Katnani, Braintree, MA (US); Julian Kates-Harbeck, Marina Del Rey, CA (US); Ryan Field, Culver City, CA (US); Gabriel Lerner, Los Angeles, CA (US); Antonio H. Lara, Valencia, CA (US)

(73) Assignee: HI LLC, Los Angeles, CA (US)

( * ) Notice: Subject to any disclaimer, the term of this patent is extended or adjusted under 35 U.S.C. 154(b) by 34 days.

This patent is subject to a terminal disclaimer.

(21) Appl. No.: 17/408,121

(22) Filed: Aug. 20, 2021

(65) Prior Publication Data

US 2021/0383277 A1 Dec. 9, 2021

Related U.S. Application Data

(63) Continuation of application No. 17/188,298, filed on Mar. 1, 2021, now Pat. No. 11,132,625.

(Continued)

(51) Int. Cl.
*G06F 3/01* (2006.01)
*G06N 20/00* (2019.01)
(Continued)

(52) U.S. Cl.
CPC .......... *G06N 20/00* (2019.01); *A61B 5/7264* (2013.01); *G06F 3/015* (2013.01);
(Continued)

(58) Field of Classification Search
None
See application file for complete search history.

(56) References Cited

U.S. PATENT DOCUMENTS

| 5,377,100 | A | 12/1994 | Pope et al. |
| 5,720,619 | A | 2/1998 | Fisslinger |

(Continued)

FOREIGN PATENT DOCUMENTS

| WO | WO02043564 | 6/2002 |
| WO | WO2012135068 | 10/2012 |

(Continued)

OTHER PUBLICATIONS

PCT International Search Report and Written Opinion for International Appln. No. PCT/US2019/024027, Applicant HI LLC, forms PCT/ISA/210, 220 and 237 dated Aug. 19, 2019 (13 pages).

(Continued)

*Primary Examiner* — Tahmina N Ansari
(74) *Attorney, Agent, or Firm* — Michael J. Bolan; Vista IP Law Group, LLP

(57) ABSTRACT

A system for training a neurome that emulates a brain of a user comprises a non-invasive brain interface assembly configured for detecting neural activity of the user in response to analog instances of a plurality of stimuli peripherally input into the brain of the user from at least one source of content, memory configured for storing a neurome configured for outputting a plurality of determined brain states of an avatar in response to inputs of the digital instances of the plurality of stimuli, and a neurome training processor configured for determining a plurality of brain states of the user based on the detected neural activity of the user, and modifying the neurome based on the plurality of determined brain states of the user and the plurality of determined brain states of the avatar.

33 Claims, 31 Drawing Sheets

Related U.S. Application Data

(60) Provisional application No. 63/047,991, filed on Jul. 3, 2020, provisional application No. 63/031,507, filed on May 28, 2020, provisional application No. 62/984,845, filed on Mar. 4, 2020.

(51) Int. Cl.
- A61B 5/00 (2006.01)
- G06K 9/00 (2022.01)
- G06N 3/004 (2023.01)
- G06N 3/006 (2023.01)
- G06N 3/02 (2006.01)
- G06N 3/08 (2023.01)
- G06Q 30/0201 (2023.01)
- A61B 5/16 (2006.01)
- G06Q 30/0242 (2023.01)

(52) U.S. Cl.
CPC ......... *G06K 9/00496* (2013.01); *G06N 3/004* (2013.01); *G06N 3/006* (2013.01); *G06N 3/02* (2013.01); *G06N 3/08* (2013.01); *G06Q 30/0201* (2013.01); *A61B 5/165* (2013.01); *G06Q 30/0242* (2013.01)

(56) References Cited

U.S. PATENT DOCUMENTS

| | | | |
|---|---|---|---|
| 5,853,370 | A | 12/1998 | Chance et al. |
| 6,488,617 | B1 | 12/2002 | Katz |
| 8,209,224 | B2 | 6/2012 | Pradeep et al. |
| 8,473,024 | B2 | 6/2013 | Causevic et al. |
| 8,609,162 | B2 | 12/2013 | Giuliano et al. |
| 8,762,202 | B2 | 6/2014 | Pradeep et al. |
| 9,101,279 | B2 * | 8/2015 | Ritchey ............... A61B 5/6803 |
| 9,114,140 | B2 | 8/2015 | Giuliano et al. |
| 9,265,974 | B2 | 2/2016 | You et al. |
| 9,339,227 | B2 | 5/2016 | Darcy et al. |
| 9,417,106 | B2 | 8/2016 | Tobita |
| 9,440,064 | B2 | 9/2016 | Wingeier et al. |
| 9,704,205 | B2 | 7/2017 | Akutagawa et al. |
| 9,712,736 | B2 | 7/2017 | Kearns et al. |
| 9,729,252 | B2 | 8/2017 | Tyler et al. |
| 9,736,603 | B2 | 8/2017 | Osborne et al. |
| 9,943,698 | B2 | 4/2018 | Chase et al. |
| 9,946,344 | B2 | 4/2018 | Ayaz et al. |
| D817,553 | S | 5/2018 | Aaskov et al. |
| D825,112 | S | 8/2018 | Saez |
| 10,091,554 | B1 | 10/2018 | Newell et al. |
| 10,143,414 | B2 | 12/2018 | el Kaliouby et al. |
| 10,188,860 | B2 | 1/2019 | Wingeier et al. |
| 10,234,942 | B2 | 3/2019 | Connor |
| 10,258,760 | B1 | 4/2019 | Sherpa et al. |
| 10,772,561 | B2 | 9/2020 | Donaldson |
| 11,132,625 | B1 * | 9/2021 | Johnson ............... G06N 20/00 |
| 2003/0176806 | A1 | 9/2003 | Pineda et al. |
| 2004/0049134 | A1 | 3/2004 | Tosaya et al. |
| 2006/0150989 | A1 | 7/2006 | Migaly |
| 2006/0161218 | A1 | 7/2006 | Danilov |
| 2008/0177197 | A1 | 7/2008 | Lee et al. |
| 2009/0083129 | A1 | 3/2009 | Pradeep et al. |
| 2009/0164549 | A1 * | 6/2009 | Jung ............... G06F 16/27 709/201 |
| 2012/0172743 | A1 | 7/2012 | Aguilar et al. |
| 2013/0289385 | A1 | 10/2013 | Lozano et al. |
| 2013/0297599 | A1 | 11/2013 | Henshall |
| 2013/0311132 | A1 | 11/2013 | Tobita |
| 2014/0023999 | A1 * | 1/2014 | Greder ............... A61B 5/375 434/236 |
| 2014/0200432 | A1 | 7/2014 | Banerji et al. |
| 2014/0228701 | A1 | 8/2014 | Chizeck et al. |
| 2014/0303450 | A1 | 10/2014 | Caponi |
| 2015/0248651 | A1 | 9/2015 | Akutagawa et al. |
| 2015/0290454 | A1 | 10/2015 | Tyler et al. |
| 2015/0297109 | A1 | 10/2015 | Garten |
| 2015/0338917 | A1 | 11/2015 | Steiner et al. |
| 2015/0355462 | A1 | 12/2015 | Saito et al. |
| 2016/0077547 | A1 | 3/2016 | Aimone |
| 2016/0220163 | A1 | 8/2016 | Yamada |
| 2016/0242690 | A1 | 8/2016 | Principe et al. |
| 2016/0270656 | A1 | 9/2016 | Samec et al. |
| 2017/0042439 | A1 | 2/2017 | Yeow |
| 2017/0164893 | A1 * | 6/2017 | Narayan ............ A61B 5/14539 |
| 2017/0173262 | A1 * | 6/2017 | Veltz ............... G16H 20/17 |
| 2017/0188876 | A1 | 7/2017 | Marci et al. |
| 2017/0202518 | A1 | 7/2017 | Furman et al. |
| 2017/0229037 | A1 | 8/2017 | Gazzaley |
| 2017/0262943 | A1 | 9/2017 | Akutagawa et al. |
| 2017/0347906 | A1 | 12/2017 | Intrator |
| 2017/0352283 | A1 | 12/2017 | Lau |
| 2018/0092557 | A1 * | 4/2018 | Bickford ............... A61B 5/375 |
| 2018/0278984 | A1 * | 9/2018 | Aimone ............ H04N 21/4788 |
| 2019/0021657 | A1 | 1/2019 | Mohammadrezazadeh et al. |
| 2019/0082990 | A1 | 3/2019 | Poltorak |
| 2019/0200888 | A1 | 7/2019 | Poltorak |
| 2019/0201691 | A1 | 7/2019 | Poltorak |
| 2019/0224441 | A1 | 7/2019 | Poltorak |
| 2019/0246929 | A1 | 8/2019 | Poltorak |
| 2019/0247662 | A1 | 8/2019 | Poltorak |
| 2019/0269372 | A1 * | 9/2019 | Gupta ............... A61B 5/24 |
| 2019/0321583 | A1 | 10/2019 | Poltorak |
| 2019/0388020 | A1 * | 12/2019 | Stauch ............... A61B 5/0022 |
| 2021/0045678 | A1 * | 2/2021 | Narayan ............ A61B 5/0531 |
| 2021/0383277 | A1 * | 12/2021 | Johnson ............ A61B 5/377 |

FOREIGN PATENT DOCUMENTS

| | | |
|---|---|---|
| WO | WO2014055932 | 4/2014 |
| WO | 2939706 | 11/2015 |
| WO | WO2019104008 | 5/2019 |

OTHER PUBLICATIONS

Lee, B.T., Seok, J.H., Lee., B.C, Cho, S.W., Chai, J.H., Choi, I.G., Ham, B.J., "Neural correlates of affective processing in response to sad and angry facial stimuli in patients with major depressive disorder," Prog Neuropsychopharmacol Biol Psychiatry, 32(3), 778-85 (2008.

A.C. Felix-Ortiz, A.C., Burgos-Robles, A., Bhagat, N.D., Leppla, C.A., Tye, K.M., "Bidirectional modulation of anxiety-related and social behaviors by amygdala projections to the medial prefrontal cortex," Neuroscience 321, 197-209 (2016).

Beauregard, M., Levesque, J. & Bourgouin, P., "Neural correlates of conscious self-regulation of emotion," J. Neurosci. (2001): 21, RC165.

Phan, K. L., Wager, T., Taylor, S. F. & Liberzon, I., "Functional neuroanatomy of emotion: a meta-analysis of emotion activation studies in PET and fMRI," Neuroimage, 16, 331-348 (2002).

Canli, T. & Amin, Z., "Neuroimaging of emotion and personality: scientific evidence and ethical considerations," Brain Cogn., 50, 414-431 (2002).

McCloskey, M. S., Phan, K. L. & Coccaro, E. F., "Neuroimaging and personality disorders," Curr. Psychiatry Rep., 7, 65-72 (2005).

Heekeren, H. R., Marrett, S., Bandettini, P. A. & Ungerleider, L. G., "A general mechanism for perceptual decision-making in the human brain," Nature, 431, 859-862 (2004).

Shin LM, Rauch SL, Pitman RK., "Amygdala, Medial Prefrontal Cortex, and Hippocampal Function in PTSD," Ann N Y Acad Sci., 1071(1) (2006).

Lis E, Greenfield B, Henry M, Guile JM, Dougherty G., "Neuroimaging and genetics of borderline personality disorder: a review," J Psychiatry Neurosci., 32(3), 162-173 (2007).

Etkin A, Wager TD, "Functional neuroimaging of anxiety: a meta-analysis of emotional processing in PTSD, social anxiety disorder, and specific phobia," Am J Psychiatry, 164(10),1476-1488 (2007).

Hamilton, P., Etkin A., "Functional Neuroimaging of Major Depressive Disorder: A Meta-Analysis and New Integration of Baseline Activation and Neural Response Data", Am J Psychiatry, 169(7), 693-703 (2012).

(56) References Cited

OTHER PUBLICATIONS

Sheline YI, Price JL, Yan Z, Mintun MA, "Resting-state functional MRI in depression unmasks increased connectivity between networks via the dorsal nexus," Proc Natl Acad Sci., 107(24), 11020-11025 (2010).
Bari A, Robbins TW, "Inhibition and impulsivity: Behavioral and neural basis of response control," Prog Neurobiol., 108:44-79 (2013).
Kagias, Konstantinos et al. "Neuronal responses to physiological stress," Frontiers in genetics, 3:222 (2012).
Clark, Ian A., et al., "First steps in using machine learning on fMRI data to predict intrusive memories of traumatic film footage", 0005-7967/2014 The Authors. Published by Elsevier Ltd. Behaviour Research and Therapy. This is an open access article under the CC by license (http://creativecommons.org/licenses/by/3.0/); 10 pgs.
George, Mark S., M.D., "Changes in Mood and Hormone Levels After Rapid-Rate Transcranial Magnetic Stimulation (rTMS) of the Prefrontal Cortex", Journal of Neuropsychiatry, vol. 8, No. 2, Spring 1996, 9 pages.
Milad, M. R., et al., "Neuroscience of fear extinction: Implications for assessment and treatment of fear-based and anxiety related disorders", Behaviour Research and Therapy (2014), http://dx.doi.org/10.1016/j.brat.2014.08.006, 7 pages.
S.Z.K, Tan et al.,"Eternal sunshine of the neuromodulated mind: Altering fear memories through neuromodulation", Experimental Neurology 314 (2019) 9-19, 11 pages.
Zhang, Fei-Fei, et al., "Brain structure alterations in depression: Psychoradiological evidence", CNS Neurosci T 2018, John Wiley & Sons Ltd her. 2018;24:994-1003, 10 pages.
Stefan K. Ehrlich, et al., "A closed-loop, music-based brain-computer interface for emotion mediation," PLoS ONE 14(3): e0213516. https://doi.org/10.1371/journal.pone.0213516; Mar. 18, 2019.
Patrick Gomez, et al., "Relationships Between Musical Structure and Psychophysiological Measures of Emotion", American Psychological Association, vol. 7, No. 2, 2007, pp. 377-387, 10 pages.
Fernando Lopes da Silva, "EEG and MEG: Relevance to Neuroscience", Center of Neuroscience; http://dx.doi.org/10.1016/j.neuron.2013.10.017; 17 pages.
Elena Boto, et al., "A new generation of magnetoencephalography: Room temperature measurements using optically-pumped magnetometers", NeuroImage 149 (2017) 404-414; 11 pages.
Stanislas Dehaene, et al., "Imaging unconscious semantic priming", Nature; vol. 395; Oct. 8, 1998; 4 pages.
John D. E. Gabrieli, et al., "The role of left prefrontal cortex in language and memory", Proc. Natl. Acad. Sci. USA, vol. 95, pp. 906-913, Feb. 1998; 8 pages.
Yang Jiang, et al., "Turning Up the Old Brain with New Tricks: Attention Training via Neurofeedback", Frontiers in Aging Neuroscience; Mar. 2017; vol. 9; Article 52; 9 pages.
Peter Lintelle, Sensory Marketing Aspects: Priming, Expectations, Crossmodal Correspondences & More; CreateSpace Independent Publishing Platform, Jul. 23, 2014, ISBN-10: 1500616400, ISBN-13: 978-1500616403; 3 pages.
Samat Moldakarimova, et al., "Perceptual priming leads to reduction of gamma frequency oscillations", PNAS, Mar. 23, 2010, vol. 107, No. 12; 6 pages.
M. Teplan, "Fundamentals of EEG Measurement", Measurement Science Review, vol. 2, Section 2, 2002; 11 pages.
Judith Amores, et al., "Promoting Relaxation Using Virtual Reality, Olfactory Interfaces and Wearable EEG," 2018 IEEE 15th International Conference on Waerable and Implantable Body Sensor Networks; Mar. 4, 2018, (4 pages).
PCT International Search Report and Written Opinion for International Appln. No. PCT/US2020/029031, Applicant HI LLC, forms PCT/ISA/210, 220 and 237 dated Sep. 2, 2020 (18 pages).
PCT International Search Report and Written Opinion for International Appln. No. PCT/US2020/025971, Applicant HI LLC, forms PCT/ISA/210, 220 and 237 dated Sep. 15, 2020 (15 pages).
PCT International Search Report and Written Opinion for International Appln. No. PCT/US2020/034831, Applicant HI LLC, forms PCT/ISA/210 and 237 dated Feb. 8, 2021 (18 pages).
PCT International Search Report and Written Opinion for International Appln. No. PCT/US2021/020258, Applicant HI LLC, forms PCT/ISA/210 and 237 dated Jun. 7, 2021 (9 pages).
Jia-Lien Hsu, et al.,"Personalized Music Emotion Recognition using Electroencephalography (EEG)", 2014 IEEE International Symposium on Multimedia (ISM) IEEE Computer Society, Los Alamitos, CA; Jan. 1, 2014; pp. 277-278, (2 pages).

* cited by examiner

METHODS FOR TRAINING AND USING A NEUROME THAT EMULATES THE BRAIN OF A USER

RELATED APPLICATION DATA

The present application is a continuation of U.S. patent application Ser. No. 17/188,298, filed Mar. 1, 2021, which claims the benefit of U.S. Provisional Application Ser. No. 62/984,845, filed Mar. 4, 2020, U.S. Provisional Application Ser. No. 63/031,507, filed May 28, 2020, and U.S. Provisional Application Ser. No. 63/047,991, filed Jul. 3, 2020. The contents of the aforementioned patent applications are hereby expressly incorporated by reference in their entirety.

FIELD OF THE INVENTION

The present inventions relate to methods and systems for non-invasive measurements in the human body, and in particular, methods and systems related to learning and predicting the behavior of a human.

BACKGROUND OF THE INVENTION

There exist various environments in which it is desirable to learn the behavior of a person. For example, when a user visits certain locations on the Internet (e.g., web sites), the user enters information in the form of online activity, which may be recorded and analyzed to determine behavioral patterns and interests of the user. In turn, these behavioral patterns and interests may be used to target the user or other similar users to provide a more meaning and rich experience on the Internet, such as an Internet portal site (e.g., Yahoo! or Google).

In one specific example, merchants may offer products or services to users on the Internet. However, a user faces a profound number of possible choices when selecting most kinds of products or services, be it movies, music, books, travel, art, dining, employers, and so on, to the extent that the user must choose from well-publicized possibilities, such as through advertising, or rely on recommendations of others.

Merchants may employ a behavior targeting system that determines interests of a user in certain products or services based on the on-line activity of the user, which information can then be used to provide recommendations or serve advertisements pertaining to those products and services, to the user. A behavior targeting system is believed to benefit both the merchant, who provides their recommendations or advertisements to a target audience, and the user, who receives more relevant recommendations or advertisements in areas of interest of the user.

However, providing recommendations and advertisements to a particular user based on on-line activity of the user is limited to the amount of time that the user actively spends on the Internet, and thus, a behavior targeting system may only learn so much from a single sampling point, i.e., on-line activity of the user. Furthermore, on-line activity of the user may be misinterpreted by the behavior targeting system (e.g., an inadvertent click on a certain webpage may be misinterpreted as an interest by the user in the content of that webpage, a display of a webpage for an extended period of time may be misinterpreted as an interest by the user in that content of that webpage when, in fact, the user has walked away from the computer or has been otherwise distracted by real-life activity, etc.).

A behavior targeting system may sample multiple points, e.g., by monitoring on-line activity from a group of users that have user profiles that are similar to that of a particular user that a merchant desires to target with recommendations or advertisements. For example, a behavior targeting system may monitor the on-line activity of a group of users having the same demographic (e.g., ethnicity, age, gender, geographic location, etc.) as the targeted user. In this manner, a virtual infinite amount of on-line information is available to the behavior targeting system in an attempt to target a particular user for recommendations or advertisements. However, this technique does not attempt to predict the behavior of the targeted user, but instead relies on the assumption that the targeted user will have the same behavior as the collective behavior of the group of users from which on-line activity was sampled. As such, this type of behavior targeted system is limited in that it cannot specifically target a user.

A behavior targeting system may also perform a "shopping basket analysis" by making suggestions to a user based on products or services that have been purchased by other users at the same time as a product or service that has been selected by the targeted user. However, this technique relies on transactional dependency and does not allow prediction of preference of products or services that are not purchased, and is not specific to the targeted user, but rather to the transaction histories across all users that purchase that product or service.

In another related example, a merchant may be interested in determining how a particular user reacts to an on-line advertisement, so that the advertisement can be evaluated to determine the value of the advertisement. For example, many merchants purchase what are generally known in the industry as "banners," which are generally designed to invite and/or incite users to click on the banner, thereby revealing additional information regarding the products or services of the merchant. However, the impact that a banner has on user who has viewed the banner is often difficult to determine or otherwise evaluate. That is, merchants currently do not have mechanisms to evaluate the impact that, for example, a banner placed as an on-line advertisement has on a user who has viewed the banner and has not necessarily clicked on the banner. The reaction and determination of how users react to on-line marketing in advertising is generally limited. For example, information as to why a user did not click on a banner or to what extent that the advertisement had on a user (e.g., how a user feels about or reacts to an advertisement) that clicked on the banner, which may otherwise provide an indication of what will motivate the user to click on the advertisement and ultimately purchase the product or service associated with the advertisement, is not available to on-line marketing techniques that make conclusions merely on banner clicks alone.

As another example, on-line research that utilizes on-line surveys to capture information from users regarding a particular subject matter has overtaken traditional survey methods. One downfall of on-line surveys is that on-line surveys operate on a conscious level, and therefore, cannot capture a user's visceral reaction to the subject matter. For example, an on-line research study may involve presenting media (e.g., video or audio) to a user and request that the user complete a questionnaire at the completion of the media presentation to determine the user's impression of the media. Some users may not be truthful in their responses, and even if truthful, the on-line questionnaires will not be able to capture the subconscious mental states and reactions of the user to the media that the user just experienced in real-time.

There, thus, remains a better means of determining a user's behavior to a stimulus for a variety of purposes, including targeted advertising, assessing the effectiveness of on-line advertisements, and extracting more useful real-time information from users during an on-line research activity.

SUMMARY OF THE INVENTION

In accordance with one aspect of the present inventions, a system for training a neurome that emulates a brain of a user is provided. The system comprises a non-invasive brain interface assembly configured for detecting neural activity of the user in response to analog instances of a plurality of stimuli peripherally input into the brain of the user from at least one source of content. The system further comprises memory configured for storing a neurome, which is configured for outputting a plurality of determined brain states (e.g., physiological brain states and/or mental brain states) of an avatar in response to inputs of the digital instances of the plurality of stimuli. In one embodiment, the system may further comprise stimulus conditioning pre-processor configured for generating the digital instances of the plurality of stimuli.

For example, the source(s) of content may be at least one real-world source of content, in which case, the stimulus conditioning pre-processor may be configured for acquiring the analog instances of the plurality of stimuli from the real-world source(s) of content, and generating the digital instances of the plurality of stimuli based on the acquired analog instances of the plurality of stimuli. The stimulus conditioning pre-processor may be configured for generating the digital instances of the plurality of stimuli by digitizing the acquired analog instances of the plurality of stimuli. In this case, the stimulus conditioning pre-processor may be further configured for modulating the analog instances of the plurality of stimuli, such that the modulated analog instances of the plurality of stimuli are peripherally input into the brain of the user.

As another example, the stimulus conditioning pre-processor may be configured for identifying the acquired analog instances of the plurality of stimuli, acquiring at least one virtual source of content, and generating the digital instances of the plurality of stimuli from the acquired virtual source(s) of content that characterizes the acquired analog instances of the plurality of stimuli.

As still another example, the stimulus conditioning pre-processor may be configured for acquiring at least one virtual source of content, generating the digital instances of the plurality of stimuli from the acquired virtual source(s) of content, and generating the analog instances of the plurality of stimuli from the generated digital instances of the plurality of stimuli.

The system further comprises a neurome training processor configured for determining a plurality of brain states (e.g., physiological brain states and/or mental brain states) of the user based on the detected neural activity of the user, and modifying the neurome based on the plurality of determined brain states of the user and the plurality of determined brain states of the avatar. In one embodiment, the neurome is configured for extracting content features from the digital instances of the plurality of stimuli characterizing the source(s) of content, and determining the plurality of determined brain states of the avatar based on the extracted content features. In another embodiment, at least some of the plurality of different brain states of the user are different from each other, and at least some of the plurality of determined brain states of the avatar are different from each other.

In one embodiment, the neurome training processor is configured for modifying the neurome, such that the plurality of determined brain states of the avatar substantially matches the plurality of determined brain states of the user. For example, the neurome training processor may comprise a comparator configured for comparing the plurality of determined brain states of the avatar and the plurality of determined brain states of the user and respectively generating a plurality of error signals, and a controller configured for modifying the neurome in a manner that is predicted to minimize the plurality of error signals.

In another embodiment, the neurome comprises a feature extraction component configured for extracting single-dimensional vectors of content features from the digital instances of the plurality of stimuli characterizing the source(s) of content, and neurome training processor is configured for modifying the neurome by inputting the single-dimensional vectors of content features into a first input of the brain state regression model (e.g., a deep neural network), and single-dimensional vectors of brain state features characterizing the determined brain states of the user into a second input of the brain state regression model, such that the brain state regression model outputs single-dimensional vectors of brain state features of the avatar that substantially match the single-dimensional vectors of brain state features of the user.

In yet another embodiment, the stimulus conditioning pre-processor may be configured for generating meta data characterizing the plurality of stimuli, the neurome may comprise a plurality of brain state models, and the neurome training processor may be configured for selecting one of the brain state models based on the generated meta data, and modifying the neurome by modifying the selected brain state model based on the plurality of determined brain states of the user and the plurality of determined brain states of the avatar.

The system may optionally further comprise one or more peripheral sensors configured for detecting peripheral physiological activity of the user in response to the analog instances of the plurality of stimuli peripherally input into the brain of the user from the source(s) of content, in which case, the neurome training processor may be configured for modifying the neurome further based on the detected peripheral physiological activity. The neurome training processor may be further optionally configured for acquiring a personal profile of the user (e.g., one or more of an internet browsing history of the user, a reading history of the user, and autobiographical information of the user), and for modifying the neurome further based on the acquired personal profile.

In one embodiment, the plurality of determined brain states of the user may comprise a plurality of physiological brain states of the user, and the plurality of brain state of the avatar may comprise a plurality of physiological brain states of the avatar. In this case, the detected neural activity of the user may comprise multi-dimensional time series of neural data, and the brain state training processor (e.g., a deep convolutional neural network) is configured for extracting brain state features from the time series of neural data characterizing the plurality of determined brain states of the user, and modifying the neurome based on the plurality of determined brain states of the avatar and the extracted brain state features characterizing the plurality of determined brain states of the user.

In this embodiment, the neurome training processor may be further configured for acquiring a plurality of mental brain states of the user in response to the analog instances of the plurality of stimuli peripherally input into the brain of the user from the source(s) of content, and modifying the neurome based on the plurality of determined mental brain states of the user. In this case, neurome training processor may be configured for correlating the plurality of acquired mental brain states of the user respectively to the plurality of determined physiological brain states of the user, and modifying the neurome based on the plurality of acquired mental brain states by storing the correlated plurality of acquired mental brain states of the user respectively and plurality of determined physiological brain states of the user in the neurome. The system may further comprise a user interface configured for receiving conscious input from the user indicating the plurality of mental brain states of the user in response to the plurality of analog stimulus instances, in which case, the neurome training processor may be further configured for acquiring the plurality of mental brain states of the user from the user interface.

In another embodiment, the plurality of determined brain states of the user may comprise a plurality of mental brain states of the user, and the plurality of brain states of the avatar may comprise a plurality of mental brain states of the avatar. In this case, the neurome training processor may be configured for determining a plurality of physiological brain states of the user based on the detected neural activity of the user, and determining the plurality of mental states of the user based on the plurality of determined physiological brain states of the user.

In one optional embodiment, the neurome training processor is configured for instructing the stimulus conditioning pre-processor to select or modify the virtual source(s) of content based on the plurality of determined brain states of the user. For example, the stimulus conditioning pre-processor may be configured for generating meta data characterizing the plurality of stimuli, and the neurome training processor may be configured for logging the determined brain states of the user and the acquired meta data, and instructing the stimulus conditioning pre-processor to select or modify the virtual source(s) of content based on the logged determined brain states of the user and the acquired meta data.

In one embodiment, the plurality of stimuli comprises a first plurality of different stimuli, and the plurality of determined brain states of the avatar comprises a plurality of different determined brain states of the avatar. The source(s) of content may comprise a first plurality of different sources of content. For example, the first plurality of different sources of content may all be in the same genre (e.g., a genre of movies, a genre of songs, a genre of books, a genre of household appliances, a genre of automobiles, a genre of foods, a genre of drinks, a genre of artwork, or sources of consumable chemical substances).

In this embodiment, the system may further comprise a brain state prediction processor (which may be the same as the neurome training processor) configured for inputting at least one digital instance of at least one stimulus from at least one source of content different than any of the first plurality of different sources of content into the neurome, such that the neurome outputs at least one determined brain state of the avatar predictive of at least one brain state of the user if at least one analog instance of the stimulus or stimuli had been peripherally input into the brain of the user. The different source(s) of content may be in the same genre as the first plurality of different sources of content.

In this embodiment, the system may further comprise one or more switches configured for switching the system between a training state and a run-time state. In the training state, the brain state determination processor is configured for determining the first plurality of brain states of the user at least partially based on the neural activity detected by the non-invasive brain interface assembly in response to the analog instances of the first plurality of different stimuli, inputting the digital instances of the plurality of different stimuli into the neurome, such that the neurome outputs the plurality of determined brain states of the avatar, and modifying the neurome based on the plurality of determined brain states of the avatar and the plurality of determined brain states of the user. In the run-time state, the brain state prediction processor is configured for inputting the digital instance(s) of the stimulus or stimuli into the neurome, such that the neurome outputs the determined brain state(s) of the avatar predictive of the brain state(s) of the user if at least one analog instance of the stimulus or stimuli from the source(s) of content had been peripherally input into the brain of the user.

In this embodiment, the system may further comprise an application post-processor configured for processing the determined brain state(s) of the avatar, generating a practical result based on the processed brain state of the avatar, and outputting the practical result to the user. The source(s) of content may comprise a second plurality of different sources of content, at least some of which are different from the first plurality of different sources of content, and the digital instance(s) of the stimulus or stimuli input into the neurome may comprise digital instances of a second plurality of different stimuli, such that the neurome outputs a second plurality of brain states of the avatar predictive of a plurality of brain states of the user if an analog instance of each of the second plurality of different stimuli had been peripherally input into the brain of the user. Generating the practical result may comprise down-selecting the second plurality of different sources of content. The application post-processor may be configured for instructing the stimulus conditioning pre-processor to select or modify the second plurality of different sources of content based on the practical result. The first plurality of different sources of content and the second plurality of different sources of content may be associated with a plurality of different products or services.

In accordance with a second aspect of the present inventions, a method of training a neurome that emulates a brain of a user is provided. The method comprises storing a neurome, peripherally inputting analog instances of a plurality of stimuli into the brain of the user from at least one source of content, detecting neural activity of the user in response to the analog instances of the plurality of stimuli peripherally input into the brain of the user, and determining a plurality of brain states (e.g., physiological brain states and/or mental brain states) of the user based on the detected neural activity of the user. The method further comprises inputting digital instances of the plurality of stimuli into the neurome, such that the neurome outputs a plurality of determined brain states (e.g., physiological brain states and/or mental brain states) of an avatar. One method further comprises generating the digital instances of the plurality of stimuli.

For example, the source(s) of content may be at least one real-world source of content, in which case, the method may further comprise acquiring the analog instances of the plurality of stimuli from the real-world source(s) of content, and generating the digital instances of the plurality of stimuli based on the acquired analog instances of the plurality of stimuli. The digital instances of the plurality of stimuli may be generated by digitizing the acquired analog instances of the plurality of stimuli. In this case, the method may further comprise modulating the analog instances of the plurality of stimuli, such that the modulated analog instances of the plurality of stimuli are peripherally input into the brain of the user.

As another example, the method may further comprise identifying the acquired analog instances of the plurality of stimuli, acquiring at least one virtual source of content, and generating the digital instances of the plurality of stimuli from the acquired virtual source(s) of content that characterizes the acquired analog instances of the plurality of stimuli.

As still another example, the method may further comprise acquiring at least one virtual source of content, generating the digital instances of the plurality of stimuli from the acquired virtual source(s) of content, and generating the analog instances of the plurality of stimuli from the generated digital instances of the plurality of stimuli.

The method further comprises modifying the neurome based on the plurality of determined brain states of the avatar and the plurality of determined brain states of the user. One method further comprises extracting content features from the digital instances of the plurality of stimuli characterizing the source(s) of content, and determining the plurality of determined brain states of the avatar based on the extracted content features. In another method, at least some of the plurality of different brain states of the user are different from each other, and at least some of the plurality of determined brain states of the avatar are different from each other.

In one method, the neurome is modified, such that the plurality of determined brain states of the avatar substantially matches the plurality of determined brain states of the user. For example, modifying the neurome may comprise comparing the plurality of determined brain states of the avatar and the plurality of determined brain states of the user, generating a plurality of error signals, and modifying the neurome in a manner that is predicted to minimize the plurality of error signals.

In another method, the neurome comprises a brain state regression model (e.g., a brain state regression model), and the modifying the neurome comprises extracting single-dimensional vectors of content features from the digital instances of the plurality of stimuli characterizing the source(s) of content, inputting the single-dimensional vectors of content features into a first input of the brain state regression model, and inputting single-dimensional vectors of brain state features characterizing the determined brain states of the user into a second input of the brain state regression model, such that the brain state regression model outputs single-dimensional vectors of brain state features of the avatar that substantially match the single-dimensional vectors of brain state features of the user.

Yet another method further comprises generating meta data characterizing the plurality of stimuli, wherein the neurome comprises a plurality of brain state models, selecting one of the brain state models based on the generated meta data, and modifying the neurome by modifying the selected brain state model based on the plurality of determined brain states of the user and the plurality of determined brain states of the avatar.

An optional method further comprises detecting peripheral physiological activity of the user in response to the analog instances of the plurality of stimuli peripherally input into the brain of the user from the source(s) of content, in which case, the neurome may be modified further based on the detected peripheral physiological activity. Another optional method may further comprise acquiring a personal profile of the user (e.g., one or more of an internet browsing history of the user, a reading history of the user, and autobiographical information of the user), in which case, the neurome may be modified further based on the acquired personal profile.

In one method, the plurality of determined brain states of the user may comprise a plurality of physiological brain states of the user, and the plurality of brain state of the avatar may comprise a plurality of physiological brain states of the avatar. In this case, the detected neural activity of the user may comprise multi-dimensional time series of neural data, and the method may further comprise extracting brain state features from the time series of neural data characterizing the plurality of determined brain states of the user. The neurome may then be modified based on the plurality of determined brain states of the avatar and the extracted brain state features characterizing the plurality of determined brain states of the user.

This method may further comprise acquiring a plurality of mental brain states of the user in response to the analog instances of the plurality of stimuli peripherally input into the brain of the user from the source(s) of content, and modifying the neurome based on the plurality of determined mental brain states of the user. In this case, the method may further comprise correlating the plurality of acquired mental brain states of the user respectively to the plurality of determined physiological mental brain states of the user. The neurome may then be modified based on the plurality of acquired mental brain states by storing the correlated plurality of acquired mental brain states of the user respectively and plurality of determined physiological mental brain states of the user in the neurome. This method may further comprise acquiring conscious input from the user indicating the plurality of mental brain states of the user in response to the plurality of analog stimulus instances. In this case, the plurality of mental brain states of the user may be acquired from the acquired conscious input of the user.

In another method, the plurality of determined brain states of the user may comprise a plurality of mental brain states of the user, and the plurality of brain states of the avatar may comprise a plurality of mental brain states of the avatar. In this case, the method may further comprise determining a plurality of physiological brain states of the user based on the detected neural activity of the user, and determining the plurality of mental states of the user based on the plurality of determined physiological brain states of the user.

One optional method further comprises selecting or modifying the virtual source(s) of content based on the plurality of determined brain states of the user. In this case, the method may further comprise generating meta data characterizing the plurality of stimuli, logging the determined brain states of the user and the acquired meta data, and selecting or modifying the virtual source(s) of content is selected or modified based on the logged determined brain states of the user and the acquired meta data In one method, the plurality of stimuli comprises a first plurality of different stimuli, and the plurality of determined brain states of the avatar comprises a plurality of different determined brain states of the avatar. The source(s) of content may comprise a first plurality of different sources of content. For example, the first plurality of different sources of content may all be in the same genre (e.g., a genre of movies, a genre of songs, a genre of books, a genre of household appliances, a genre of automobiles, a genre of foods, a genre of drinks, a genre of artwork, or sources of consumable chemical substances).

This method may further comprise generating at least one digital instance of at least one stimulus from at least one source of content different than any of the first plurality of different sources of content, inputting the digital instance(s) of the stimulus or stimuli into the neurome, such that the neurome outputs at least one determined brain state of the avatar predictive of at least one brain state of the user if at least one analog instance of the stimulus or stimuli had been peripherally input into the brain of the user. The different source(s) of content may be in the same genre as the first plurality of different sources of content.

One optional method may further comprise processing determined brain state(s) of the avatar, generating a practical result based on the processed brain state(s) of the avatar, and outputting the practical result to the user. Generating the digital instance(s) of the stimulus or stimuli may comprise generating digital instances of a second plurality of different stimuli from a second plurality of different sources of content, at least some of which are different from the first plurality of different sources of content. Inputting the digital instance(s) of the stimulus or stimuli into the neurome may comprise inputting the digital instances of the second plurality of different stimuli into the neurome, such that the neurome outputs a plurality of determined brain states of the avatar predictive of a plurality of brain states of the user if an analog instance of the each of the plurality of different stimuli had been peripherally input into the brain of the user. Generating the practical result may comprise down-selecting the second plurality of different sources of content. The method may further comprise selecting or modifying the second plurality of different sources of content based on the practical result. The first plurality of different sources of content and the second plurality of different sources of content may be associated with a plurality of different products or services.

In accordance with a third aspect of the present inventions, a system for using a neurome of an avatar is provided. The system comprises memory configured for storing the neurome, and a brain state prediction processor configured for acquiring at least one digital instance of at least one stimulus from at least one source of content and inputting the digital instance(s) of the stimulus or stimuli into the neurome, such that the neurome outputs at least one determined brain state of the avatar. The brain state prediction processor is further configured for predicting at least one mental brain state of the user as if at least one analog instance of the stimulus or stimuli had been peripherally input into the brain of the user.

In one embodiment, the source(s) of content comprises a plurality of different sources of content, such that the digital instance(s) of the stimulus or stimuli input into the neurome comprises digital instances of a plurality of different stimuli. In this case, the brain state prediction processor may be further configured for acquiring the digital instances of the plurality of different stimuli from the plurality of different sources of content, inputting the digital instances of the plurality of different stimuli into the neurome, such that the neurome outputs a plurality of determined brain states of the avatar, and predicting a plurality of mental brain states of the user as if analog instances of the plurality of different stimuli had been peripherally input into the brain of the user. At least some of the plurality of determined brain states of the avatar are different from each other. For example, the plurality of different sources of content are all in the same genre (e.g., genre of movies, a genre of songs, a genre of books, a genre of household appliances, a genre of automobiles, a genre of foods, a genre of drinks, a genre of artwork, or sources of consumable chemical substances).

In still another embodiment, the brain state(s) of the avatar output by the neurome comprises at least one physiological brain state of the avatar, in which case, the brain state prediction processor may be configured for predicting the mental brain state of the user based on the physiological brain state(s) of the avatar. In yet another embodiment, the brain state(s) of the avatar output by the neurome comprises at least one mental brain state of the avatar, and the brain state prediction processor is configured for outputting the mental brain state(s) of the avatar as the predicted mental state(s) of the user.

An optional embodiment of the system further comprises an application post-processor configured for processing the predicted mental state(s) of the user, generating a practical result based on the processed predicted mental brain state(s), and outputting the practical result to the user. If the predicted mental state(s) of the user comprises a plurality of predicted mental states of the user, the practical result may comprise down-selecting the plurality of different sources of content. The application post-processor may be configured for instructing the stimulus conditioning pre-processor to select or modify the plurality of different sources of content based on the practical result. The plurality of different sources of content may be associated with a plurality of different products or services.

Another optional embodiment of the system may further comprise a non-invasive brain interface assembly configured for detecting neural activity of the user in response to analog instances of the plurality of different stimuli peripherally input into the brain of the user from the plurality of different sources of content, and a neurome training processor configured for determining a plurality of brain states of the user at least partially based on the neural activity detected by the non-invasive brain interface assembly, and modifying the neurome based on the plurality of determined brain states of the avatar and the plurality of determined brain states of the user.

In accordance with a fourth aspect of the present inventions, a method for using a neurome of an avatar comprises generating at least one digital instance of at least one stimulus from at least one source of content, inputting the digital instance of the stimulus or stimuli into the neurome, such that the neurome outputs at least one determined brain state of the avatar, and predicting at least one mental brain state of the user as if at least one analog instance of the stimulus or stimuli had been peripherally input into the brain of the user.

In one method, the source(s) of content comprises a plurality of different sources of content, such that the digital instance(s) of the stimulus or stimuli comprises digital instances of a plurality of different stimuli. In this case, inputting the digital instance(s) of the stimulus or stimuli into the neurome comprises inputting the digital instances of the plurality of different stimuli into the neurome, such that the neurome outputs a plurality of determined brain states of the avatar, and predicting the mental brain state(s) of the user comprises predicting a plurality of mental brain states of the user as if analog instances of the plurality of different stimuli had been peripherally input into the brain of the user. At least some of the plurality of determined brain states of the avatar are different from each other. For example, the plurality of different sources of content are all in the same genre (e.g., genre of movies, a genre of songs, a genre of books, a genre of household appliances, a genre of automobiles, a genre of foods, a genre of drinks, a genre of artwork, or sources of consumable chemical substances).

In another method, the brain state(s) of the avatar output by the neurome comprises at least one physiological brain state of the avatar, in which case, the mental brain state(s) of the user may be predicted based on the physiological brain state(s) of the avatar. In still another method, the brain state(s) of the avatar output by the neurome comprises at least one mental brain state of the avatar, and the mental brain state(s) of the avatar is output as the predicted mental state(s) of the user. Yet another method further comprises processing the predicted mental state(s) of the user, and generating a practical result based on the processed predicted mental brain state(s), and outputting the practical result to the user.

An optional method further comprises processing the plurality of predicted mental brain state of the user, generating a practical result based on plurality of processed predicted mental brain states of the user, and outputting the practical result to the user. If the predicted mental state(s) of the user comprises a plurality of predicted mental states of the user, the practical result may comprise down-selecting the plurality of different sources of content. The method may further comprise instructing the stimulus conditioning preprocessor to select or modify the plurality of different sources of content based on the practical result. The plurality of different sources of content may be associated with a plurality of different products or services.

Another optional method further comprises detecting neural activity of the user in response to analog instances of the plurality of different stimuli peripherally input into the brain of the user from the plurality of different sources of content, determining a plurality of brain states of the user at least partially based on the neural activity detected by the non-invasive brain interface assembly, and modifying the neurome based on the plurality of determined brain states of the avatar and the plurality of determined brain states of the user.

In accordance with a fifth aspect of the present inventions, a neurome of an avatar that emulates a brain of a user is provided. The neurome comprises a feature extraction component configured for receiving at least one digital instance of at least one stimulus from at least one source of content, extracting content features from the digital instance(s) of the stimulus or stimuli characterizing the source(s) of content, and outputting the extracted content features. In one embodiment, the feature extraction component is configured for outputting the extracted content features as a single-dimensional vector of content features.

The neurome further comprises a brain state model (e.g., a brain state regression model, such as a deep neural network) configured for receiving the extracted content features from the feature extraction component, and outputting at least one brain state of the avatar that predicts at least one brain state (e.g., a mental brain state) of the user as if at least one analog instance of the stimulus or stimuli were to be peripherally input into the brain of the user. In one embodiment, the brain state model is configured for outputting the brain state of the avatar as brain state features characterizing the brain state of the avatar. The brain state model may be configured for outputting the brain state features as a single-dimensional vector of content features.

In one embodiment, the source(s) of content comprises a plurality of different sources of content, such that the digital instance(s) of the stimulus or stimuli input into the neurome comprises digital instances of a plurality of different stimuli. At least some of the plurality of determined brain states of the avatar are different from each other. For example, the plurality of different sources of content are all in the same genre (e.g., genre of movies, a genre of songs, a genre of books, a genre of household appliances, a genre of automobiles, a genre of foods, a genre of drinks, a genre of artwork, or sources of consumable chemical substances).

In another embodiment, the brain state(s) of the avatar output by the brain state model comprises at least one physiological brain state of the avatar that predicts at least one physiological state of the user as if at least one analog instance of the stimulus or stimuli were to be peripherally input into the brain of the user. The neurome may further comprise a look-up table containing a plurality of reference physiological brain states to which a plurality of reference mental brain states are respectively associated, and mental brain state determination component configured for receiving the physiological brain state(s) from the brain state model, accessing the look-up table, matching each of the physiological brain state(s) of the avatar output by the brain state model to a reference physiological brain state in the look-up table, and outputting the reference mental brain state(s) associated with the matched reference physiological brain state(s).

In still another embodiment, the neurome further comprises a plurality of feature extraction components, each of which is configured for receiving at least one digital instance of at least one stimulus from at least one source of content, extracting content features from the digital instance(s) of the stimulus or stimuli characterizing the source(s) of content, and outputting the extracted content features. The neurome further comprises a plurality of brain state models, each of which is configured for receiving the extracted content features from a respective one of the plurality of feature extraction components, and outputting at least one brain state of the avatar that predicts at least one brain state of the user as if at least one analog instance of the at stimulus or stimuli were to be peripherally input into the brain of the user.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
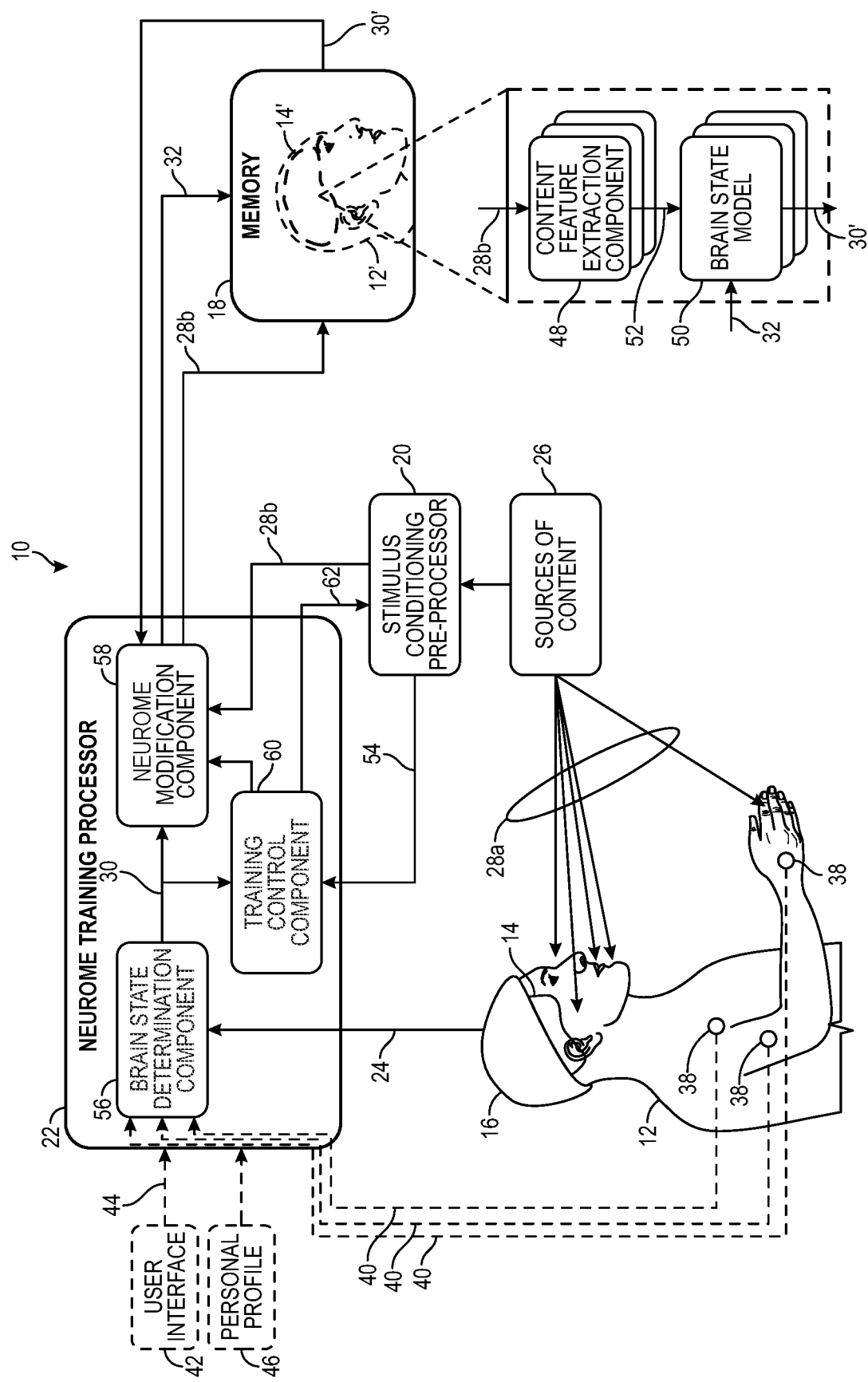
FIG. 1 is a block diagram of one embodiment of a neurome training system constructed in accordance with the present inventions.

The present disclosure is directed to the training and usage of a "neurome," which is a component in which stimuli (e.g., video, audio, text, etc.) from one or more sources of content (e.g., a movie, a book, a song, a household appliance, an automobile, food, artwork, or sources of consumable chemical substances (where the chemical substances can include, e.g., caffeinated drinks, soft drinks, energy drinks, tobacco products, drugs (pharmaceutical or recreational), etc.) can be input and from which a brain state, predictive of the brain state of the user or from which a predicted brain state, behavior, preferences, or attitude of the user, can be derived, is output as if the user received the same stimuli. In this regard, it can be said that the neurome outputs a brain state of an "avatar" of the user, which can be defined as a virtual manifestation of the user.

The neurome may be trained on different stimuli and the resulting brain states acquired from the user in response to that stimuli. In the illustrated embodiments described herein, the neurome is trained by inputting digital instances of the stimuli into the neurome and detecting neural activity from the brain of the user in response to analog instances of the stimuli that are peripherally input into the brain of the user (e.g., via one or more of the senses of the user), and modifying the neurome in such a manner that the brain states output by the neurome (i.e., the brain states of the avatar) in response to digital instances of the stimuli input into the neurome substantially match the brain states acquired from the user in response to the analog instances of the same stimuli peripherally input into the brain of the user via the senses of the user. A neurome of an avatar of the user may be trained on stimuli from one or more genres of sources of content (e.g., books) or one or more sub-genres of sources of content (e.g., adventure books), and once fully trained, may emulate the brain of the user in that the neurome may predict the brain state of the user or output information from which the brain state of the user may be predicted in response to stimuli that, although acquired from the same genre or sub-genre of sources of content on which the neurome has been trained, may be from sources of content that are different from those on which the neurome has been trained. In this regard, the neurome of the avatar emulates the brain of the user in that it allows the brain state of the user to be predicted in response to new stimuli that that the avatar has not previously experienced.

Although the embodiments and methods for training and using a neurome are described in an advertising or marketing context, it should be appreciated that a neurome can be trained and used outside of an advertising or marketing context. Furthermore, although a brain state is described herein as being predicted from the output of the neurome, it should be appreciated that behavior, preferences, or attitude of the user can similarly be predicted from the output of the neurome.

Referring now to FIG. 1, one embodiment of a neurome training system 10 for training a neurome 14' of an avatar 12' that emulates the brain 14 of a user 12 will be described. The neurome training system 10 generally comprises non-invasive brain interface assembly 16, a memory 18, a stimulus conditioning pre-processor 20, and a neurome training processor 22. The non-invasive brain interface assembly 16 is configured for detecting neural activity 24 in the brain 14 of the user 12 in response to analog instances 28a of a plurality of stimuli 28 peripherally input into the brain 14 of the user 12 from different sources of content 26. The memory 18 is configured for storing the neurome 14'. The stimulus conditioning pre-processor 20 is configured for generating digital instances 28b of the stimuli 28. The neurome training processor 22 is configured for determining a plurality of brain states 30 of the user 12 at least partially based on the detected neural activity 24 in the brain 14 of the user 12, and modifying the neurome 14' via control signals 32 based on determined brain states 30 of the user 12 and a plurality of determined brain states 30' output by the neurome 14' in response to digital instances 28b of the stimuli 28 that have been input into the neurome 14'.

The neurome training system 10 may optionally comprise one or more peripheral sensors 38 configured for, in response to analog instances 28a of stimuli 28 peripherally input into the brain 14 of the user 12 from the sources of content 26, detecting peripheral physiological functions of the user 12, e.g., heart rate, respiratory rate, blood pressure, skin conductivity, etc., and generating peripheral physiological signals 40 that are correlated to the brain state 30 of the user 12 in response to such measurements. The neurome training processor 22 may then use the peripheral physiological signals 40 to facilitate training of the neurome 14', as discussed in further detail below. It should be appreciated that, while certain physiological functions of the user 12 may be correlated to the brain state 30 of the user 12, and therefore used to facilitate training of the neurome 14', the detected neural activity 24 in the brain 14 of the user 12 is much more informative of the brain state 30 of the user 12, and therefore, it is paramount that the neurome training processor 22 utilize at least the detected neural activity 24 when training the neurome 14'.

The neurome training system 10 may also optionally comprise a user interface 42 (e.g., a keyboard, microphone, button, remote control, etc.) configured for receiving conscious input 44 from the user 12 indicating a mental brain state of the user 12 in response to peripherally receiving the analog stimulus instances 28a. For example, as the user 12 peripherally receives the analog stimulus instances 28a, the user 12 can be queried to provide the conscious input 44 via the user interface 42 indicating the mental brain state perceived by the user 12. The query can either be opened ended, multiple choice, or binary (i.e., yes or no). The neurome training processor 22 may then acquire the conscious input 44 of the user 12 from the user interface 42 to facilitate training the neurome 14', as discussed in further detail below.

The neurome training system 10 may also optionally comprise an on-line personal profile 46 (e.g., one or more of an internet browsing history of the user 12, a reading history of the user 12, and autobiographical information of the user 12). The neurome training processor 22 may then acquire the personal profile 46 to facilitate training the neurome 14', as discussed in further detail below.

Each source of content 26 may be, e.g., a movie, a book, a song, a household appliance, an automobile, food, artwork, or sources of consumable chemical substances (e.g., caffeinated drinks, soft drinks, energy drinks, tobacco products, drugs (pharmaceutical or recreational)), etc., and each of the analog stimuli 28a may be peripherally input into the brain 14 of the user 12 via any one or more of senses of the user 12 (e.g., the five traditionally recognized sensory modalities of somatosensation (touch), vision (sight), audition (hearing), olfaction (smell), and gustation (taste), as well as other sensory modalities, such as thermoception (temperature), proprioception (kinesthetic sense), nociception (pain), equilibrioception (balance), mechanoreception (vibration), etc.).

For example, if a source of content 26 is a movie, the analog stimulus 28a may comprise sights/sounds of the movie in the form of video that is peripherally input into the brain 14 of the user 12 via sight and the sounds of the movie in the form of audio that is peripherally input into the brain 14 of the user 12 via hearing. If a source of content 26 is a book, the analog stimulus 28a may comprise words of the book peripherally input into the brain 14 of the user 12 via sight or hearing. If a source of content 26 is a song, the analog stimulus 28a may comprise sounds of the song peripherally input into the brain 14 of the user 12 via hearing. If a source of content 26 is a household appliance, the analog stimulus 28a may comprise the look of the household appliance peripherally input into the brain 14 of the user 12 via sight or may comprise the feel of the household appliance peripherally input into the brain 14 of the user 12 via touch. If a source of content 26 is an automobile, the analog stimulus 28a may comprise the look of the automobile peripherally input into the brain 14 of the user 12 via sight or may comprise the driving feel of the automobile peripherally input into the brain 14 of the user 12 via balance. If a source of content 26 is food, the analog stimulus 28a may comprise the flavor of the food input into the brain 14 of the user 12 via taste or a look of the food input into the brain 14 of the user 12 via sight or the flavor of the food via smell or the temperature of the food via touch. If a source of content 26 is artwork, the analog stimulus 28a may comprise the color, texture, and lines of the artwork peripherally input into the brain 14 of the user via sight. If the source of content 26 is a consumable chemical substance, e.g., caffeinated drink or other types of drinks, the analog stimulus 28a may comprise the flavor of the drink input into the brain 12 of the user 12 via taste and/or smell or the temperature of the drink via touch. Alternatively, if the source of content 26 is another type of consumable chemical substance, e.g., drugs (pharmaceutical or recreational), the analog stimulus 28a may comprise the type of drug, dosage of the drug, and/or reaction time for the dosage to take its prescribed effect and/or its known side effect input into the brain 14 of the user 12. The known prescribed effect may comprise, e.g., reduction of sensitivity to pain, happiness, general well-being, relaxation, etc. The known side effect may comprise, e.g., drowsiness, hallucinations, paranoia, aggression, anxiety, depression, memory loss, compulsive behaviors, suicidality, etc. Thus, it can be appreciated that an analog stimulus 28a can peripherally input into the brain 14 of the user 12 in any suitable manner that allows the user 12 to experience the source of content 26 to evoke a response in the form of detectable neural activity 24 in the brain 14 of the user 12.

It should be appreciated that each of the analog stimuli 28a may correspond to one of a plurality of segments of the source of content 26 or the entirety of the source of content 26. For example, if the source of content 26 is the type to evoke several brain states from the user 12, the analog stimuli 28a may correspond to different segments of the sources of content 26 (e.g., different paragraphs or different chapters of a book, or a scene of a movie), and if the source of content 22 is the type to evoke a singular brain state from the user 12, the analog stimuli 28a may correspond to different sources of content 26 (e.g., different songs, different household appliance, different automobiles, different foods, different drinks, different artwork, or different consumable chemical substances, etc.).

Referring still to FIG. 1, the exemplary embodiment of the neurome 14' generally comprises a content feature extraction component 48 configured for receiving digital instances 28*b* of the stimuli 28 from the sources of content 26, extracting content features 52 from the digital instances 28*b* of the stimuli 28 characterizing the sources of content 26, and a brain state model 50 configured for receiving the extracted content features 52 and outputting determined brain states 30' of the avatar 12'. The digital stimulus instances 28*b* will typically be a time-series of multi-dimensional information, and as such, the feature extraction component 48 may extract the most important or useful features 52 from the sources of content 26 and output them as a single-dimensional vector of features 52.

For example, if the sources of content 26 are books, each digital stimulus instance 28*b* may take the form of written language (text) or verbal language, and the feature extraction component 48 may examine key words from the text or verbal language and generate descriptors; e.g., romance, comedy, mystery, adventure, factual, etc., which can be subdivided into types to form the vector of features 52. If the sources of content 26 are movies, each digital stimulus instance 28*b* may take the form of video and audio, and the feature extraction component 48 may examine key words from the audio and objects within the video and generate descriptors, e.g., documentaries, adventure, romance, mystery, etc., which can be further subdivided into types to form the vector of features 52. If the sources of content 26 are songs, each digital stimulus instance 28*b* may take the form of lyrics and music, and the feature extraction component 48 may examine key words in the lyrics and melodies of the music and generate descriptors, e.g., rock, blues, pop, rap, etc., which can be further divided to form the vector of features 52. If the sources of content 26 are physical objects, e.g., house appliances, furniture, clothing, or automobiles, each digital stimulus instance 28*b* may take the form of a photograph, and the feature extraction component 48 may examine the photograph and generate descriptors, e.g., type, model, color, etc., to form the vector of features 52. If the sources of content 26 are food items, each digital stimulus instance 28*b* may take the form of a photograph, and the feature extraction component 48 may examine the photograph and generate descriptors, e.g., type of food item, salty, sweet, savory, sour, bitter, etc., to form the vector of features 52. If the sources of content 26 are pieces of art, each digital stimulus instance 28*b* may take the form of a photograph, and the feature extraction component 48 may examine the photograph and generate descriptors, e.g., artist, type of artwork, type of scenery, etc., to form the vector of features 52.

The brain state model 50 may take the form of any suitable machine learning algorithm, which may provide a regression output and may contain various components and layers that can include but are not limited to: classical machine learning models such as support vector machines, random forests, or logistic regression, as well as modern deep learning models such as deep convolutional neural networks, attention-based networks, recurrent neural networks, or fully connected neural networks. The goal is for the brain state model 50 to accurately predict future data, i.e., by virtue of the brain states 30' output by the brain state model 50 in response to subsequent digital instances 28*b* of stimuli 28. The brain state model 50, once fully trained, will be capable of predicting the brain states 30 of the user 12 as if analog instances 28*a* of the same stimuli 28 were to be peripherally input into the brain 14 of the user 12. As will be described in further detail below, the neurome training processor 22 trains the neurome 14', such that the determined brain states 30' of the avatar 12' output by the brain state model 50 in response to the digital instances 28*b* of the stimuli 28 substantially match the determined brain states 30 of the user 12 in response to the analog instances 28*a* of the same stimuli 28 peripherally received by the user 12.

The non-invasive brain interface assembly 16 may be any device capable of non-invasively acquiring hi-fidelity signals representing neural activity 24 in the brain 14 of the user 12. In the preferred embodiment, the non-invasive brain interface assembly 16 is portable and wearable, such that the user 12 may operate the non-invasive brain interface assembly 16 in a normal life and working environment. Several embodiments of brain interface assemblies 16 that may be used in the neurome training system 10 as will be described in further detail below.

For purposes of this specification, a "normal life and work environment" is an environment that is usual and ordinary, and thus, necessitates that the user 12 be able to freely ambulate without any physical hindrance by the neurome training system 10 or other system to which the neurome training system 10 is coupled or otherwise is an adjunct. Thus, a normal life and work environment excludes settings in which the user is unable to freely move (e.g., any clinical setting in which a conventional magnetic resonance imaging (MRI) machine or computed tomography (CT) could potentially be used to detect neural activity from the user and hinder the user's movement). In alternative embodiments, the non-invasive brain interface assembly 16 may be non-portable and/or non-wearable in cases where it is suitable for the non-invasive brain interface assembly 14 to be operated outside of a normal life and working environment, e.g., in a clinical environment.

As illustrated in FIG. 1, the neurome 14' may optionally comprise multiple brain state models 50 and associated content feature extraction components 48. For example, each brain state model 50 and associated content feature extraction component 48 may be trained for a particular genre of sources of content 26. For example, one brain state model 50 and associated content feature extraction component 48 can be trained on sources of content 26 associated within one genre (e.g., books); another brain state model 50 and associated content feature extraction component 48 can be trained on sources of content 26 associated with another genre (e.g., movies); still another brain state model 50 and associated content feature extraction component 48 can be trained on sources of content 26 associated with still another genre (e.g., songs); and so forth.

The stimulus conditioning pre-processor 20 is configured for generating the digital instances 28*b* of the stimuli 28, the analog instances 28*a* of which are to be or have been peripherally input into the brain 14 of the user 12 from the sources of content 26. The stimulus conditioning pre-processor 20 is also configured for generating meta data 54 characterizing the stimuli 28. For example, if the source of content 26 is a book, the meta data 54 may be include a title, author, fiction, factual, etc. If the source of content 26 is a movie, the meta data 54 may include a title, name of director, name of main actors, type of movie (e.g., adventure, mystery, comedy, drama, etc.), etc. If the source of content 26 is a song, the meta data 54 may include a title of the song, singer, musical group, type of song (e.g., rock, rhythm and blues, pop, soul, etc.). If the source of content 26 is a household appliance, the meta data 54 may include the type of household appliance, the color of the household appliance, the model of the household appliance, etc.). If the source of content 26 is an automobile, the meta data 54 may include the type of automobile (e.g., sports car, truck, luxury, economical, etc.), the color of the automobile, the model of the automobile, etc.). If the source of content 26 is a food item, the meta data 54 may include the type of food (hamburger, pizza, ice cream, steak, etc.), the taste profile of the food (e.g., sour, sweet, bitter, savory, salty, etc.). The stimulus conditioning pre-processor 20 is configured for inputting the digital instances 28*b* of the stimuli 28 and the meta data 54 characterizing the stimuli 28 into the neurome training processor 22 for usage in training the neurome 14', as will be described in further detail below. The configuration of the stimulus conditioning pre-processor 20 will depend on the nature of the source of content 26, as will be described in further detail below. The stimulus conditioning pre-processor 20 may generate the meta data 54 based on an analysis of the stimuli 28, or if the source of content 26 has already associated meta data 54 with the stimuli 28, the stimulus conditioning pre-processor 20 may simply acquire this meta data 54 without an analysis of the stimuli 28.

The neurome training processor 22 is configured for training the neurome 14' (which may start as a generic model of a typical brain) on the stimuli 28 (e.g., from the same genre of sources of content 26), such that the fully trained neurome 14' emulates the brain 14 of the user 12, at least with respect to stimuli 28 from the same genre of sources of content 26 on which the neurome 14' has been trained. Thus, in response to digital instances of stimuli from sources of content that are different from the stimuli 28 on which the neurome 14' has been trained, the fully trained neurome 14' may output brain states 30' of the avatar 12' that are respectively predictive of brain states 30 of the user 12 if analog instances of the same stimuli 28 from these different sources of content had been peripherally received by the user 12, as will described below with respect to FIG. 11. Each of the brain states 30' may not only include the existence of the brain state 30', itself, but also the extent of the brain state 30' (e.g., how much and for how long does the avatar 14' have that brain state 30'). The neurome 14' may be trained, such that the neurome 14' outputs the same brain state 30', but preferably, the neurome 14' should be trained, such that at least some of the brain states 30' output from the neurome 14' are different from each other to increase the robustness of the neurome 14', e.g., by training the neurome 14' on different types of stimuli 28.

In one embodiment, the different sources of content 26 from which the stimuli 28 are acquired to train the neurome 14' have the same genre. For example, the same genre of the different sources of content 26 may be one of a genre of movies, a genre of songs, a genre of books, a genre of household appliances, a genre of automobiles, a genre of foods, a genre of artwork, or sources of consumable chemical substances. In this case, neurome 14' trained by the neurome training processor 22, in response to digital instances of stimuli from sources of content 26 that are different from the stimuli 28 on which the neurome 14' has been trained, may output brain states 30' of the avatar 12' that are respectively predictive of brain states 30 of the user 12 if analog instances 28*a* of the same stimuli 28 from these different sources of content had been peripherally received by the user 12, as described below with respect to FIG. 10. Thus, in this case, the neurome 14' will more effectively emulate the brain 14 of the user 12 in that neurome 14' will be capable of predicting brain states 30 of the user 12 for stimuli 28 for which digital stimulus instances 28*b* have not been previously input into the neurome 14' during training of the neurome 14'.

The neurome training processor 22 generally comprises: (1) a brain state determination component 56 configured for determining brain states 30 of the user 12 based on the neural activity 24 of the brain 14 of the user 12 that has been detected by the brain interface assembly 16 in response to the analog stimulus instances 28*a* peripherally input into the brain 14 of the user 12 from different sources of content 26; (2) a neurome modification component 58 configured for modifying the neurome 14' based on the determined brain states 30' of the avatar 12' and the determined brain states 30 of the user 12; and (3) an optional training control component 60 configured for controlling the stimulus pre-processor 20 based on the neural activity 24 of the brain 14 of the user 12 that has been detected by the brain interface assembly 16 and the meta data 54 received from the stimulus conditioning pre-processor 20.

As described in further detail below, the brain state 30 of the user 12 that is determined by the brain state determination component 56 of the neurome training processor 22 may be a physiological brain state (or low-level brain state), which is the state of physiological activity in the brain 12, a mental brain state (or high-level brain state), which is an interpretation made by the brain 14 in response to physiological activity in the brain 12, or both a physiological brain state and a mental brain state.

The neurome modification component 58 of the neurome training processor 22 is configured for training the neurome 14' on the digital stimuli 28*b* acquired from the sources of content 26. That is, the neurome modification component 58 acquires the digital instances 28*b* of the stimuli 28 from the stimulus conditioning pre-processor 20 and inputs these digital stimulus instances 28*b*, as a set of stimulus training data, into the content feature extraction component 48 of the neurome 14', and furthermore, acquires the brain states 30, as a set of brain state training data, output by the brain state determination component 56 in response to analog instances 28*a* of the same stimuli 28 peripherally input into the brain 14 of the user 12 as training data for the neurome 14'. Since the stimulus training data and the brain state training data may be assumed to represent ground truths, the neurome modification component 58 may confidently use this training data to modify the neurome 14' via control signals 32 in a manner, such that the brain states 30' output by the neurome 14' in response to digital stimulus instances 28*b* match the brain states 30 of the user 12 in response to the peripheral input of the analog stimulus instances 28*a* into the brain 14 of the user 12, as determined by the brain state determination processor 22. Further details discussing the neurome modification component 58 will be described below.

The training control component 60 is configured for steering the training of the neurome 14' by generating and outputting control signals 62 to the stimulus conditioning pre-processor 20, and instructing the stimulus conditioning pre-processor 20 to select or modify the sources of content 26 (if possible) based on the determined brain states 30 of the user 12. In this manner, the neurome training processor 22 may control the training of the neurome 14'. For example, if the determined brain states 30 of the user 12 are consistently different from a desired brain state of the user 12, the training control component 60 may instruct the stimulus conditioning pre-processor 20 to select different sources of content 26 from which analog instances 28*a* will be peripherally input into the brain 14 of the user 12 in order to evoke brain states 30 that are more consistent with the desired brain state. Or, if the determined brain states 30 of the user 12 are consistently the same as each other, the training control component 60 may instruct the stimulus conditioning pre-processor 20 to select different sources of content 26 from which analog stimulus instances 28a will be presented to the user 12 in order to evoke brain states 30 that are more varied relative to each other.

To facilitate steering of the training of the neurome 14', the training control component 60 may log the brain states 30 determined by the brain state determination component 56, along with the meta data 54 received from the stimulus conditioning pre-processor 20 characterizing the stimuli 28, the analog instances 28a of which have been peripherally input into the brain 14 of the user 12 to yield the determined brain states 30 of the user 12, and the digital instances 28b of which have been input into the neurome 14' to yield the determined brain states 30' of the avatar 12'. The training control component 60 can, therefore, be better informed in controlling the training of the neurome 14'. For example, if the avatar 12' yields inconsistent brain states 30' in response to a particular set of similar stimuli 28 (e.g., a set of stimuli 28 acquired from adventure books), based on the meta data 54 indicating that the set of stimuli 28 correspond to adventure books, the training control component 60 may be opt to control the stimulus pre-processor 20 via the control signals 62 to continue to select stimuli 28 from sources of content 26 related to adventure books, so that nuances between adventure books can be captured when training the neurome 14'.

In the case where the neurome 14' comprises multiple brain models 50 and associated content feature extraction components 48, the training control component 60 may select which of the brain models 50 to train based on meta data 54 acquired from the stimulus conditioning pre-processor 20. In particular, the training control component 60 may inform the neurome modification component 58 to input the digital stimulus instances into the content feature extraction component 48 associated with a selected one of the brain state models 50, and to modify that selected brain state model 50 based on the determined brain states 30' of the avatar 12' output by that brain state model 50 of the neurome 14' in response to the input of the digital stimulus instances 28b into the content feature extraction component 48 associated with that selected brain state model 50, and the determined brain states 30 of the user 12 output by the brain state determination component 56 in response to the analog stimulus instances 28a peripherally input into the brain 14 of the user 12.

For example, if the stimulus conditioning pre-processor 20 acquires digital stimulus instances 28b from sources of content 26 pertaining to books, the stimulus conditioning pre-processor 20 may generate meta data 54 indicating that the digital stimulus instances 28b are from books, which meta data 54 is communicated to the training control component 60. The training control component 60 may then inform the neurome modification component 58 to input the digital stimulus instances 28b into the content feature extraction component 48 associated with the brain state model 50 corresponding to books, and further inform the neurome modification component 58 to modify the brain state model 50 corresponding to books based on the determined brain states 30' of the avatar 12' output by that brain state model 50 of the neurome 14' in response to the input of the digital stimulus instances 28b into the content feature extraction component 48 associated with that brain state model 50, and the determined brain states 30 of the user 12 output by the brain state determination component 56 in response to the analog stimulus instances 28a (which also are from the sources of content 26 pertaining to books) peripherally input into the brain 14 of the user 12.

Figure 2:
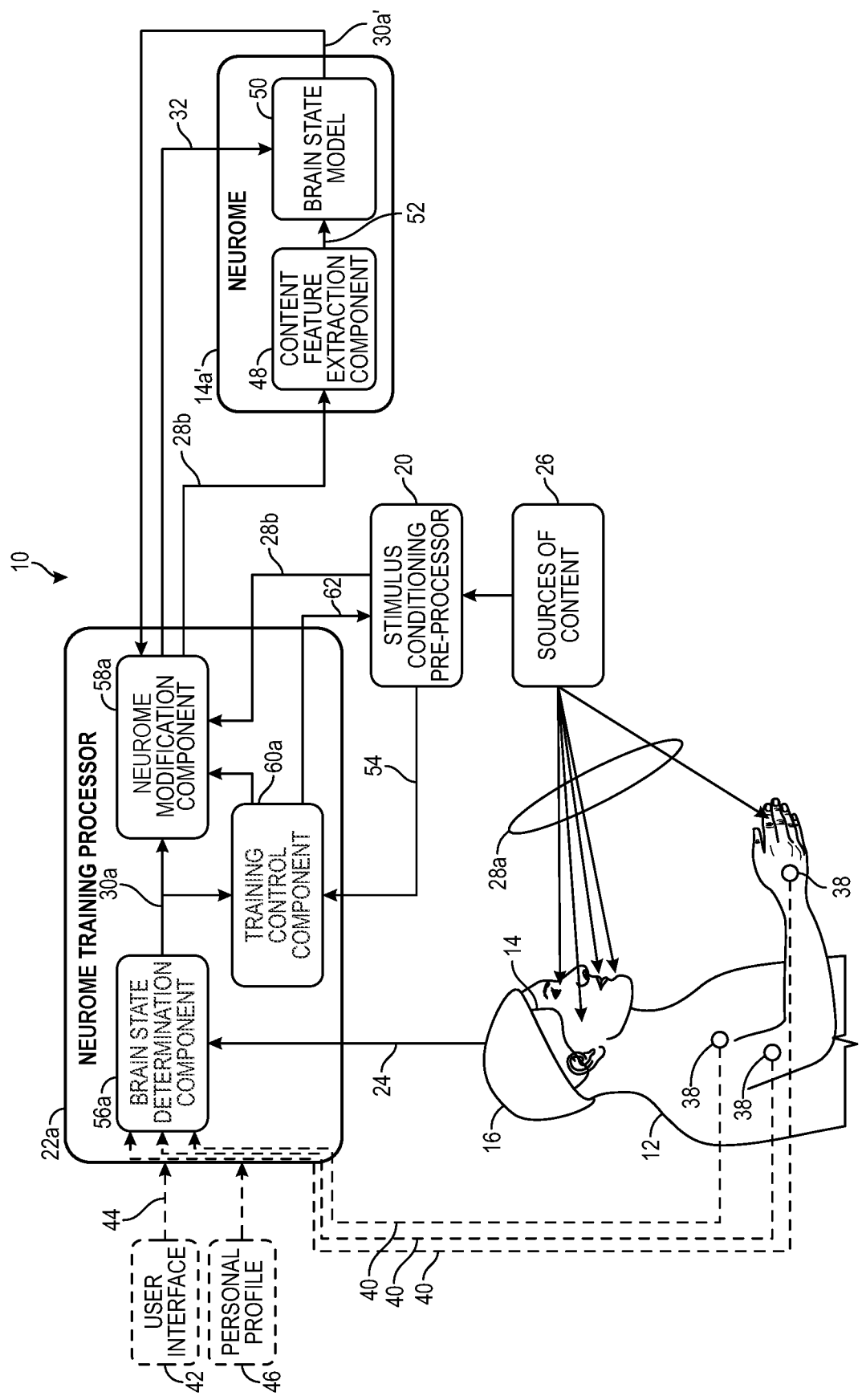
FIG. 2 is a block diagram of one specific implementation of the neurome training system of FIG. 1.

Referring now to FIG. 2, one embodiment of a neurome training processor 22a that can be used in the neurome training system 10 of FIG. 1 for training a neurome 14a' will be described. In this embodiment, the neurome 14a' is configured for determining and outputting determined physiological (low-level) brain states 30a' of the avatar 12' in response to digital instances 28b of stimuli 28 input into the neurome 14a', and the neurome training processor 22a is configured for modifying the neurome 14a' based on the determined physiological brain states 30a' of the avatar 12' output by the neurome 14a' and the neural activity 24 of the brain 14 of the user 12 detected by the brain interface assembly 16.

A physiological brain state 30a of the user 12 is defined by characteristics of the spatiotemporal brain activity that is captured, and can include, e.g., location or spatial pattern of neural activity, fine grained pattern within or across locations, amplitude of signal, timing of response to behavior, magnitude of frequency bands (Gamma, Beta, Alpha, Theta, and Delta) of the signal (taking the Fourier transform of the time series), ratio of magnitude of frequency bands, cross-correlation between time series of signal between two or more locations captured simultaneously, spectral coherence between two or more locations captured simultaneously, components that maximize variance, components that maximize non-gaussian similarity, etc. The characteristics of the brain activity can be extracted from preprocessed raw data, which typically involves filtering the raw detected data (either in the time domain or the frequency domain) to smooth, remove noise, and separate different components of signal.

To this end, the neurome training processor 22a comprises a brain state determination component 56a configured for determining physiological brain states 30a of the user 12 based on the detected neural activity 24 of the brain 14 output by the brain interface assembly 16 in response to the analog stimulus instances 28a peripherally input into the brain 14 of the user 12 from the sources of content 26. In the illustrated embodiment, the brain state determination component 56a is configured for extracting brain state features from a time series of the neural data characterizing the determined brain states 30a of the user 12.

The brain state determination component 56a may optionally be configured for determining the physiological brain states 30a of the user 12 further based on peripheral physiological signals 40 received from the peripheral sensors 38 in response to analog stimulus instances 28a peripherally input into the brain 14 of the user 12 from the sources of content 26. That is, the peripheral physiological functions of the user 12, e.g., heart rate, respiratory rate, blood pressure, skin conductivity, etc., may inform the physiological brain states 30a of the user 12 that have been determined in response to the analog stimulus instances 28a based on the detected neural activity 24 of the brain 14.

The neurome training processor 22a further comprises a neurome modification component 58a configured for modifying the brain state model 50 of the neurome 14a' based on the determined physiological brain states 30a' of the avatar 12' output by the brain state model 50 of the neurome 14a' and the determined physiological brain states 30a of the user 12 (and in particular, the extracted brain features characterizing the determined physiological brain states 30a) output by the brain state determination component 56a. In the illustrated embodiment, the neurome modification component 58a modifies the brain state model 50 of the neurome 14a', such that the determined physiological brain states 30a' of the avatar 12' output by the brain state model 50 of the neurome 14', and the determined physiological brain states 30*a* of the user 12 output by the brain state determination component 56*a*, substantially match each other.

The neurome training processor 22*a* further comprises a training control component 60*a*, the functionality of which is similar to the training control component 60 described above with respect to FIG. 1, with the exception that certain control functions of the training control component 60*a* may be specifically based on the physiological brain states 30*a* determined by the brain state determination component 56*a*.

Figure 3:
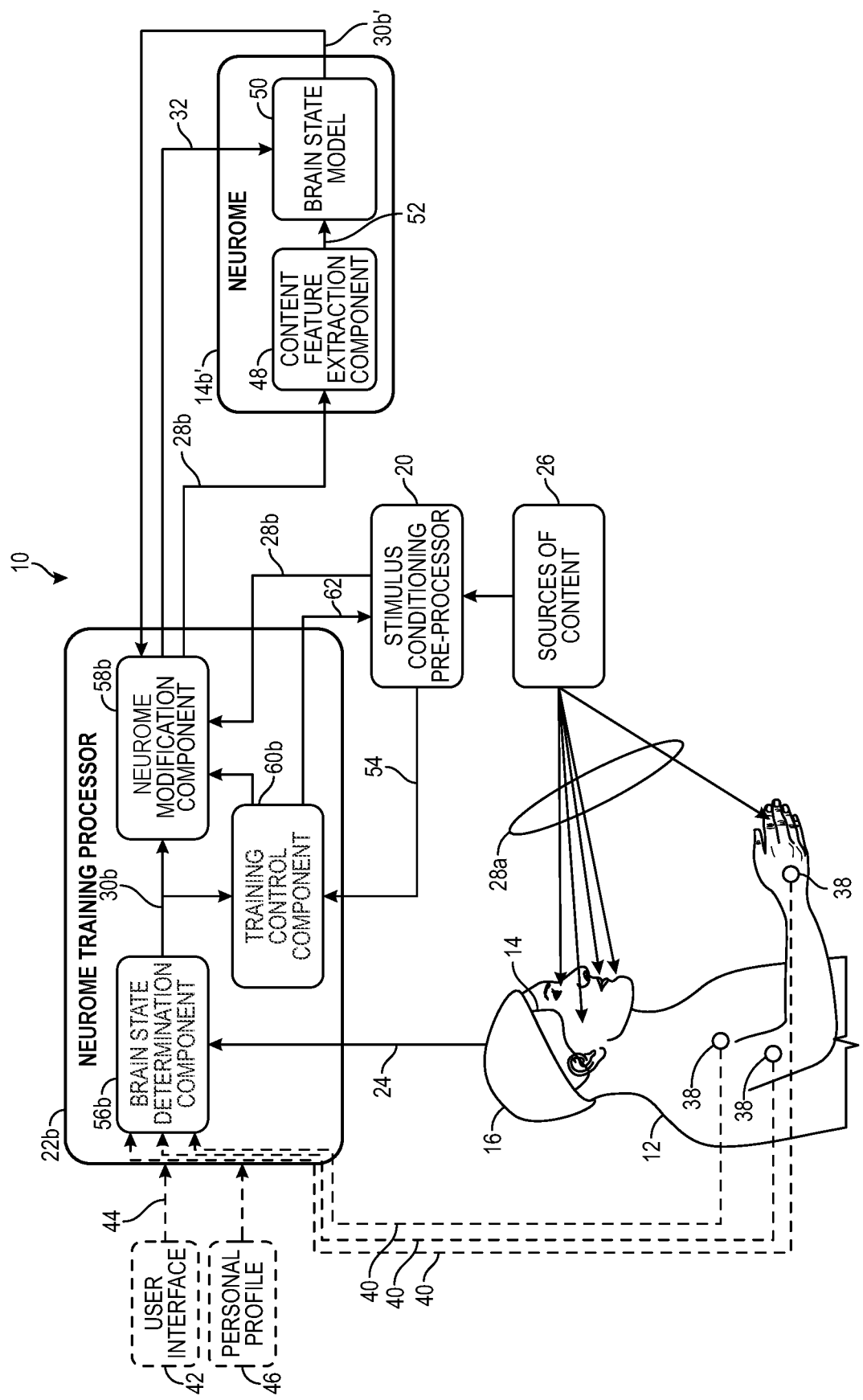
FIG. 3 is a block diagram of another specific implementation of the neurome training system of FIG. 1.

Referring now to FIG. 3, another embodiment of a neurome training processor 22*b* that can be used in the neurome training system 10 of FIG. 1 for training a neurome 14*b'* will be described. In this embodiment, the neurome 14*b'* is configured for determining and outputting mental (high-level) brain states 30*b'* of the avatar 12' in response to digital instances 28*b* of stimuli 28 input into the neurome 14*b'*, and the neurome training processor 22*b* is configured for modifying the neurome 14*b'* based on the determined mental brain states 30*b'* of the avatar 12' output by the neurome 14*b'* and the neural activity 24 of the brain 14 of the user 12 detected by the brain interface assembly 16.

A mental brain state 30*b* of the user 12 may include, e.g., an emotional state (e.g., joy, excitement, relaxation, surprise, anxiety, sadness, anger, disgust, contempt, fear, etc.), a cognitive state encompassing intellectual functions and processes (e.g., memory retrieval, focus, attention, creativity, reasoning, problem solving, decision making, comprehension and production of language, etc.), or a perceptive state (e.g., face perception, color perception, sound perception, visual perception, texture perception by touch etc.). As an adjunct to predicting the mental brain states 30*b* of the user 12 based on detected neural activity 24 of the brain 14 of the user 12, physiological functions, such as blushing, frowning, smiling, yawning, rolling shoulders, grimacing, swallowing, etc., may be additionally determined.

The neurome training processor 22*b* comprises a brain state determination component 56*b* configured for determining mental brain states 30*b* of the user 12 based on the detected neural activity 24 of the brain 14 output by the brain interface assembly 16 in response to the analog stimulus instances 28*a* peripherally input into the brain 14 of the user 12 from the sources of content 26. The brain state determination component 56*b* may determine a mental brain state 30*b* of the user 12 based on the detected brain activity (i.e., based on the physiological brain state in this case) in any one of a variety of manners.

In one embodiment, the brain state determination component 56*b* may perform a univariate approach in determining the mental brain state 30*b* of the user 12, i.e., the brain activity can be detected in a plurality (e.g., thousands) of separable cortical modules of the user 12, and the brain activity obtained from each cortical module can be analyzed separately and independently. In another embodiment, the brain state determination component 56*b* performs a multivariate approach in determining the brain state 30*b* of the user 12, i.e., the brain activity can be detected in a plurality (e.g., thousands) of separable cortical modules of the user 12, and the full spatial pattern of the brain activity obtained from the cortical modules can be assessed together.

The brain state determination component 56*b* may use any one of a variety of models to classify the brain state 30*b* of the user 12, which will highly depend on the characteristics of brain activity that are input onto the models. Selection of the characteristics of brain activity to be input into the models must be considered in reference to univariate and multivariate approaches, since the univariate approach, e.g., focuses on a single location, and therefore will not take advantage of features that correlate multiple locations. Selecting a model will be heavily dependent on whether the data is labeled or unlabeled (meaning is it known what the user 12 is doing at the time that the brain activity is detected), as well as many other factors (e.g., is the data assumed to be normally distributed, is the data assumed relationship linear, is the data assumed relationship non-linear, etc.) Models can include, e.g., support vector machines, expectation maximization techniques, naïve-Bayesian techniques, neural networks, simple statistics (e.g., correlations), deep learning models, pattern classifiers, etc.

These models are typically initialized with some training data (meaning that a calibration routine can be performed on the user 12 to determine what the user 12 is doing). If no training information can be acquired, such models can be heuristically initialized based on prior knowledge, and the models can be iteratively optimized with the expectation that optimization will settle to some optimal maximum or minimum solution. Once it is known what the user 12 is doing, the proper characteristics of the neural activity 24 and proper models can be queried. The models may be layered or staged, so that, e.g., a first model focuses on pre-processing data (e.g., filtering), the next model focuses on clustering the pre-processed data to separate certain features that may be recognized to correlate with a known activity performed by the user 12, and then the next model can query a separate model to determine the brain state 30*b* based on that user activity.

Training data or prior knowledge of the user 12 may be obtained by providing known life/work context to the user 12 (e.g., peripheral physiological functions of the user 12, e.g., heart rate, respiratory rate, blood pressure, skin conductivity, etc., acquired from the physiological signals 40 received from the peripheral sensors 38), the user's perception of his or her mental state acquired from the conscious input 44 from the user 12 indicating a mental brain state 30*b* of the user 12 received from the user interface 42, or background information specific to the user 12 acquired from the personal profile 46 of the user). Altogether, the models can be used to track the brain state 30*b* and perception under natural or quasi-natural (i.e., in response to providing known life/work context to the user 12) and dynamic conditions taking in the time-course of averaged activity and determining the brain state 30*b* of the user 12 based on constant or spontaneous fluctuations in the characteristics of the brain activity extracted from the data.

A set of data models that have already been proven, for example in a laboratory setting, can be initially uploaded to the neurome training system 10, which the brain state determination component 56*b* will then use to determine the mental brain state 30*b* of the user 12. Optionally, the neurome training system 10 may collect data during actual use with the user 12, which can then be downloaded and analyzed in a separate server, for example in a laboratory setting, to create new or updated models. Software upgrades, which may include the new or updated models, can be uploaded to the neurome training system 10 to provide new or updated data modelling and data collection.

Further details regarding determining the mental brain state of a person based on detected brain activity can be found in a variety of peer-reviewed publications. See, e.g., Lee, B. T., Seok, J. H., Lee., B. C, Cho, S. W., Chai, J. H., Choi, I. G., Ham, B. J., "Neural correlates of affective processing in response to sad and angry facial stimuli in patients with major depressive disorder," *Prog Neuropsychopharmacol Biol Psychiatry,* 32(3), 778-85 (2008); A. C.

Felix-Ortiz, A. C., Burgos-Robles, A., Bhagat, N. D., Leppla, C. A., Tye, K. M., "Bidirectional modulation of anxiety-related and social behaviors by amygdala projections to the medial prefrontal cortex," *Neuroscience* 321, 197-209 (2016); Beauregard, M., Levesque, J. & Bourgouin, P., "Neural correlates of conscious self-regulation of emotion," *J. Neurosci.* (2001): 21, RC165; Phan, K. L., Wager, T., Taylor, S. F. & Liberzon, I., "Functional neuroanatomy of emotion: a meta-analysis of emotion activation studies in PET and fMRI," *Neuroimage*, 16, 331-348 (2002); Canli, T. & Amin, Z., "Neuroimaging of emotion and personality: scientific evidence and ethical considerations," *Brain Cogn.*, 50, 414-431 (2002), McCloskey, M. S., Phan, K. L. & Coccaro, E. F., "Neuroimaging and personality disorders," *Curr. Psychiatry Rep.*, 7, 65-72 (2005); Heekeren, H. R., Marrett, S., Bandettini, P. A. & Ungerleider, L. G., "A general mechanism for perceptual decision-making in the human brain," *Nature*, 431, 859-862 (2004); Shin L M, Rauch S L, Pitman R K. Amygdala, Medial Prefrontal Cortex, and Hippocampal Function in PTSD, *Ann NY Acad Sci.*, 1071(1) (2006); Lis E, Greenfield B, Henry M, Guile J M, Dougherty G., "Neuroimaging and genetics of borderline personality disorder: a review," *J Psychiatry Neurosci.*, 32(3), 162-173 (2007); Etkin A, Wager T D, "Functional neuroimaging of anxiety: a meta-analysis of emotional processing in PTSD, social anxiety disorder, and specific phobia," *Am J Psychiatry*, 164(10), 1476-1488 (2007); Etkin A. Functional Neuroimaging of Major Depressive Disorder: A Meta-Analysis and New Integration of Baseline Activation and Neural Response Data, *Am J Psychiatry*, 169(7), 693-703 (2012); Sheline Y I, Price J L, Yan Z, Mintun M A, "Resting-state functional MRI in depression unmasks increased connectivity between networks via the dorsal nexus, *Proc Natl Acad Sci.*, 107(24), 11020-11025 (2010); Bari A, Robbins T W, "Inhibition and impulsivity: Behavioral and neural basis of response control," *Prog Neurobiol.*, 108:44-79 (2013); Kagias, Konstantinos et al. "Neuronal responses to physiological stress," Frontiers in genetics, 3:222 (2012).

The neurome training processor 22b further comprises a neurome modification component 58b configured for modifying the brain state model 50 of the neurome 14b' based on the determined mental brain states 30b' of the avatar 12' output by the brain state model 50 of the neurome 14b' and the determined mental brain states 30b of the user 12 output by the brain state determination component 56b. In the illustrated embodiment, the neurome modification component 58b modifies the brain state model 50 of the neurome 14b', such that the determined mental brain states 30b' of the avatar 12' output by the brain state model 50 of the neurome 14b', and the determined mental brain states 30b of the user 12 output by the brain state determination component 56b, substantially match each other.

The brain state determination component 56b may optionally be configured for determining the mental brain states 30b' of the user 12 further based on peripheral physiological signals 40 received from the peripheral sensors 38 in response to analog stimulus instances 28a peripherally input into the brain 14 of the user 12 from the sources of content 26; the conscious input 44 from the user 12 indicating a mental brain state 30b of the user 12 received from the user interface 42; and/or the personal profile 46 of the user 12. That is, the peripheral physiological functions of the user 12, e.g., heart rate, respiratory rate, blood pressure, skin conductivity, etc., the user's perception of his or her mental state, and background information specific to the user 12 may inform the mental brain states 30b of the user 12 that have been determined in response to the based on the detected neural activity 24 of the brain 14.

The neurome training processor 22b further comprises a training control component 60b, the functionality of which is similar to the training control component 60 described above with respect to FIG. 1, with the exception that certain control functions of the training control component 60b may be specifically based on the mental brain states 30b determined by the brain state determination component 56b.

Figure 4:
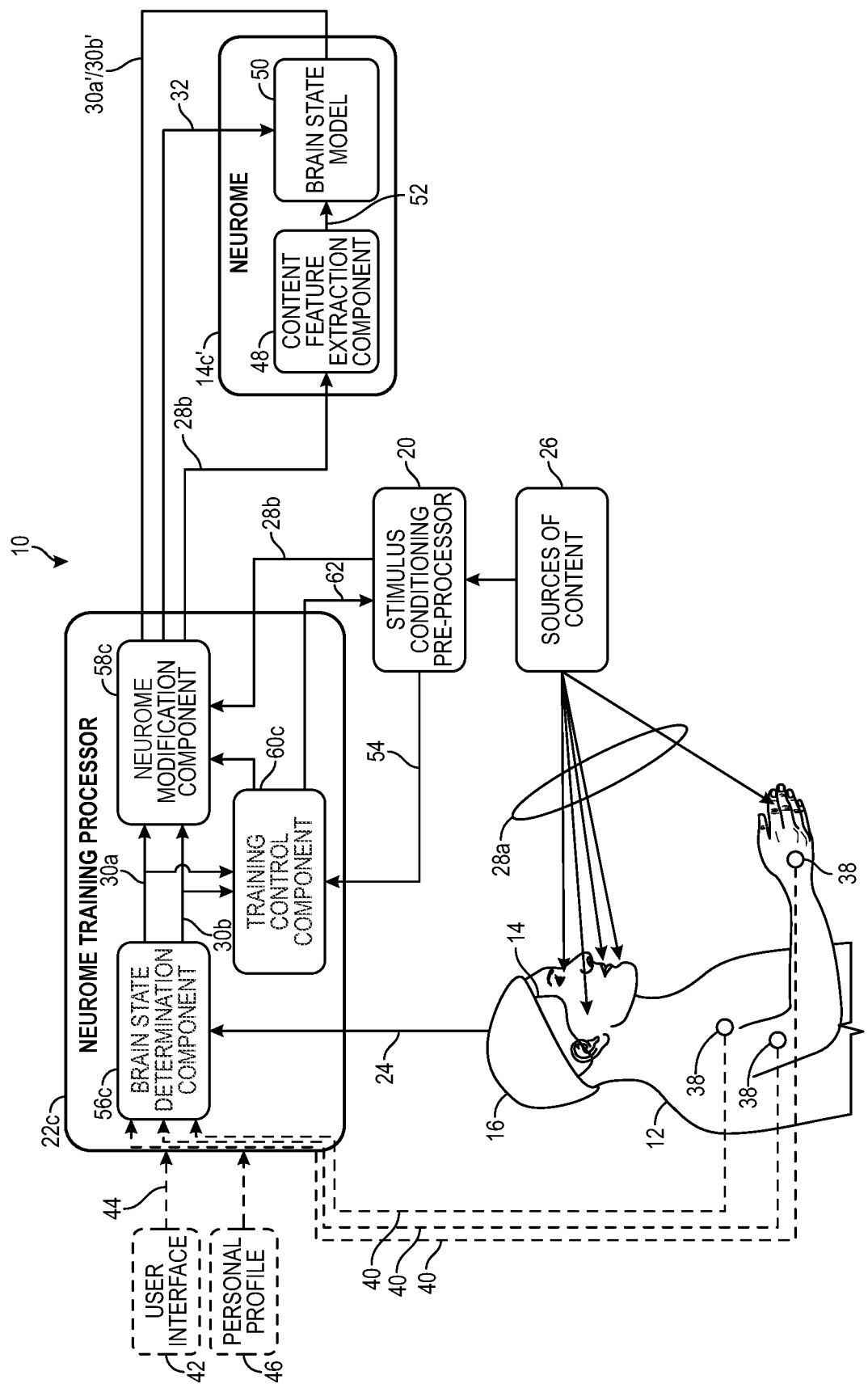
FIG. 4 is a block diagram of still another specific implementation of the neurome training system of FIG. 1.

Referring now to FIG. 4, still another embodiment of a neurome training processor 22c that can be used in the neurome training system 10 of FIG. 1 for training a neurome 14c' will be described. In this embodiment, the neurome 14c' is configured for determining and outputting both physiological (low-level) brain states 30a' and determined mental (high-level) brain states 30b' of the avatar 12' in response to digital instances 28b of stimuli 28 input into the neurome 14c', and the neurome training processor 22c is configured for modifying the neurome 14c' based on the determined physiological brain states 30a' and determined mental brain states 30b' of the avatar 12' output by the neurome 14c' and the neural activity 24 of the brain 14 of the user 12 detected by the brain interface assembly 16.

To this end, the neurome training processor 22c comprises a brain state determination component 56c configured for determining physiological brain states 30a and mental brain states 30b of the user 12 based on the detected neural activity 24 of the brain 14 output by the brain interface assembly 16 in response to the analog stimulus instances 28a peripherally input into the brain 14 of the user 12 from the sources of content 26. The neurome training processor 22c further comprises a neurome modification component 58c configured for modifying the brain state model 50 of the neurome 14b' based on the determined physiological brain states 30a' and mental brain states 30b' of the avatar 12' output by the brain state model 50 of the neurome 14' and the determined physiological brain states 30a and mental brain states 30b of the user 12 output by the brain state determination component 56c. In the illustrated embodiment, the neurome training processor 22c modifies the brain state model 50 of the neurome 14b', such that the determined physiological brain states 30a' and mental brain states 30b' of the avatar 12' output by the brain state model 50 of the neurome 14' and the determined physiological brain states 30a and mental brain states 30b of the user 12 output by the brain state determination component 56c substantially match each other.

The brain state determination component 56c may optionally be configured for determining the physiological brain states 30a and mental brain states 30b of the user 12 further based on peripheral physiological signals 40 received from the peripheral sensors 38 in response to the analog stimulus instances 28a peripherally input into the brain 14 of the user 12 from the sources of content 26; the conscious input 44 from the user 12 indicating a mental brain state 30b of the user 12 received from the user interface 42; and/or the personal profile 46 of the user 12. That is, the peripheral physiological functions of the user 12, e.g., heart rate, respiratory rate, blood pressure, skin conductivity, etc., the user's perception of his or her mental state, and background information specific to the user 12 may inform the mental brain states 30b of the user 12 that have been determined in response to the based on the detected neural activity 24 of the brain 14.

The neurome training processor 22c further comprises a training control component 60c, the functionality of which is similar to the training control component 60 described above with respect to FIG. 1, with the exception that certain control functions of the training control component 60c may be specifically based on both the physiological mental states 30a and the mental brain states 30b determined by the brain state determination component 56c.

Figure 5:
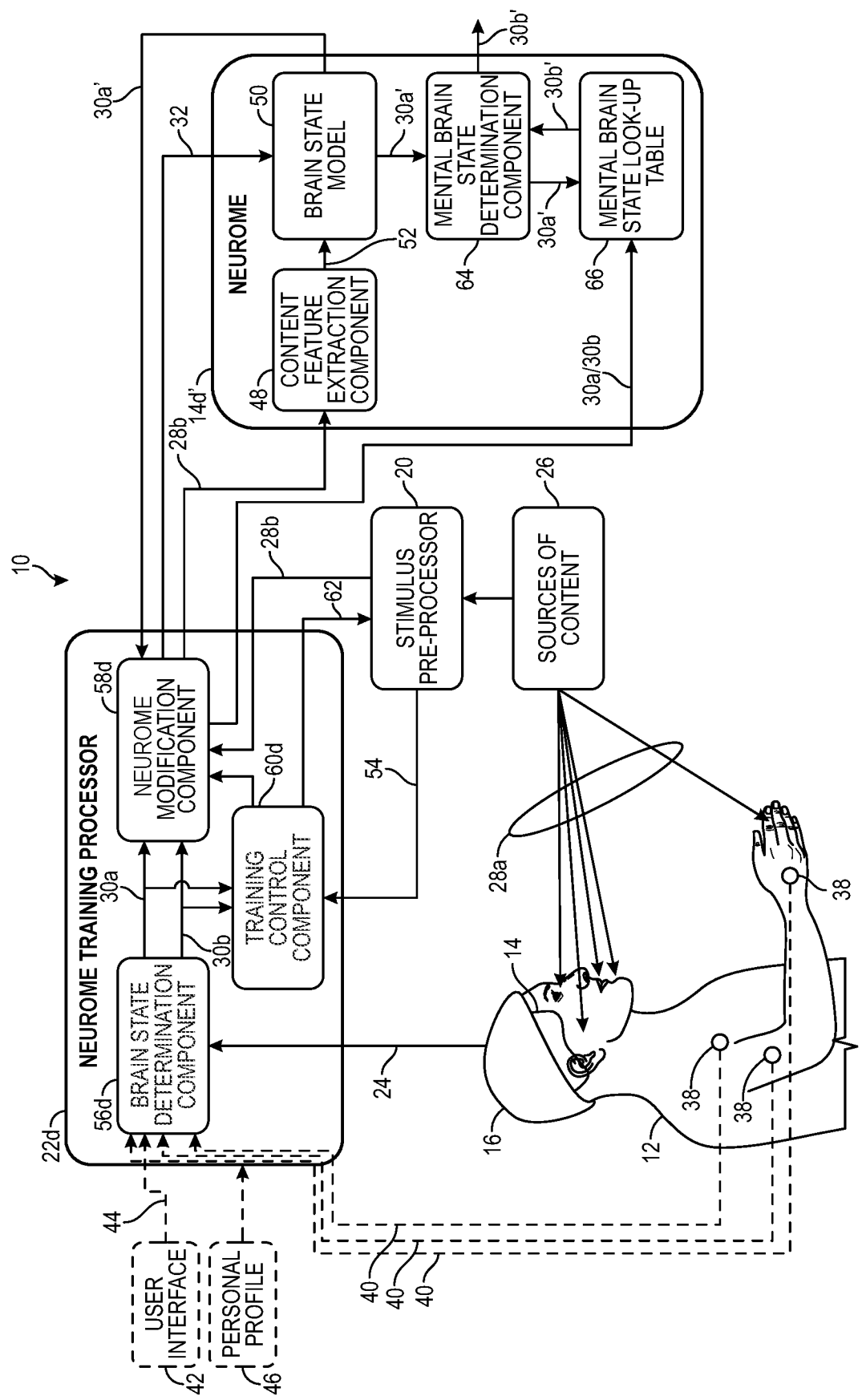
FIG. 5 is a block diagram of yet another specific implementation of the neurome training system of FIG. 1.

Referring now to FIG. 5, yet another embodiment of a neurome training processor 22d that can be used in the neurome training system 10 of FIG. 1 for training a neurome 14d' will be described. In this embodiment, the neurome 14d' is configured for outputting both determined physiological (low-level) brain states 30a' and determined mental (high-level) brain states 30b' in response to digital instances 28b of stimuli 28 input into the neurome 14d', and the neurome training processor 22d is configured for modifying the neurome 14d' based on the determined physiological brain states 30a' and determined mental brain states 30b' output by the neurome 14b' and the neural activity 24 of the brain 14 of the user 12 detected by the brain interface assembly 16.

The neurome 14d' is similar to the neurome 14c' in FIG. 3 in that it is configured for outputting determined physiological (low-level) brain states 30a' and determined mental (high-level) brain states 30b' in response to digital instances 28b of stimuli 28 input into the neurome 14d'. However, the neurome 14d' differs from the neurome 14b' in FIG. 3 in that, in addition to the content feature extraction component 48 and the brain state model 50, which outputs only determined physiological brain states 30a', the neurome 14d' further comprises a mental brain state determination component 64 configured for determining a mental brain state 30b' from each physiological brain state 30a' output by the brain state model 50 in response to digital instances 28b of stimuli 28 input into the neurome 14d', and outputting the determined mental brain states 30b'. In the exemplary embodiment, the mental brain state determination component 54 accesses a look-up table 66 containing a plurality of reference physiological brain states to which reference mental brain states are respectively associated, matches each physiological brain state 30a' output by the brain state model 50 to a reference physiological brain state in the look-up table 66, and outputs the reference mental brain state associated with the matched reference physiological brain state, as the mental brain state 30b' of the avatar 12' along with the physiological brain state 30a' of the avatar 12' output by the brain state model 50. Although only mental brain state determination component 64 and one look-up table 66 are illustrated in FIG. 5, in the case where the neurome 14' includes multiple brain state models 50 and associated content feature extraction components 48, multiple mental brain state determination components 64 and one look-up tables 66 can be provided for the respective multiple brain state models 50 and associated content feature extraction components 48 in a dedicated manner.

Similar to the neurome training processor 22c illustrated in FIG. 4, the neurome training processor 22d comprises a brain state determination component 56d configured for determining both the physiological brain states 30a and the mental brain states 30b of the user 12. However, while brain state determination component 56d determines the physiological brain states 30a based on the detected neural activity 24 of the brain 14 output by the brain interface assembly 16 in response to the analog stimulus instances 28a peripherally input into the brain 14 of the user 12 from the sources of content 26, the brain state determination component 56d determines the mental brain states 30b, not based on the physiological brain states 30a, but rather independently based on known life/work context to the user 12.

In the exemplary embodiment, the brain state determination component 56d determines the mental brain states 30b of the user 12 from the conscious input 44 from the user 12 via the user interface 42 indicating the mental brain states 30b of the user 12. The mental brain state 30b determination may be informed by peripheral physiological functions of the user 12, e.g., heart rate, respiratory rate, blood pressure, skin conductivity, etc., indicated by physiological signals 40 received from the peripheral sensors 38 in response to the analog stimulus instances 28a peripherally input into the brain 14 of the user 12 from the sources of content 26, and background information specific to the user 12 obtained from the personal profile 46 of the user 12.

Unlike the neurome modification component 58c illustrated in FIG. 4, the neurome modification component 58d is configured for modifying the brain state model 50 of the neurome 14a' based only on the determined physiological brain states 30a' of the avatar 12' output by the brain state model 50 of the neurome 14' and the determined physiological brain states 30a of the user 12 output by the brain state determination component 56d, such that the determined physiological brain states 30a' of the avatar 12' output by the brain state model 50 of the neurome 14' and the determined physiological brain states 30a of the user 12 output by the brain state determination component 56a substantially match each other.

The neurome modification component 58d is further configured for respectively correlating the physiological brain states 30a and the mental brain states 30b of the user 12 determined by the brain state determination component 56d, and modifying the look-up table 66 of the neurome 14' by storing the correlated physiological brain states 30a and mental brain states 30b as correlated reference physiological brain states and mental brain states described above in the look-up table 66.

The neurome training processor 22d further comprises a training control component 60d, the functionality of which is similar to the training control component 60 described above with respect to FIG. 1, with the exception that certain control functions of the training control component 60d may be specifically based on both the physiological mental states 30a and the mental brain states 30b determined by the brain state determination component 56d.

As briefly discussed and shown on the embodiments described above, the neurome modification component 58 of the neurome training processor 22 trains the neurome 14' on two sets of known or true data: the digital instances 28b of stimuli 28 acquired from the sources of content 26, and the determined brain states 30 (physiological brain states 30a and/or mental brain states 30b) of the user 12 acquired from the brain state determination component 56 in response to the analog instances 28a of the same stimuli 28 peripherally input into the brain 14 of the user 12. The neurome modification component 58 may be configured for training the neurome 14' using machine-learning either on-line, meaning that the neurome 14' is serially and continually updated or modified as the training data becomes available, or off-line, meaning that an entire set of training data is accumulated or batched over a period of time, and then concurrently used to modify the neurome 14'. The advantage of using an on-line machine learning technique to train the neurome 14' is that it can be used when it is computationally infeasible to train over an entire set of training data, and furthermore, can dynamically adapt to new patterns in the training data or training data that changes as a function of time. In contrast, the advantage of using an off-line machine learning technique to train the neurome 14' is that the neurome 14' may be trained in a more robust manner, such that the fully trained neurome 14' becomes a better of predictor of the brain states 30 (physiological brain states 30a and/or mental brain states 30b) of the user 12.

Figure 6:
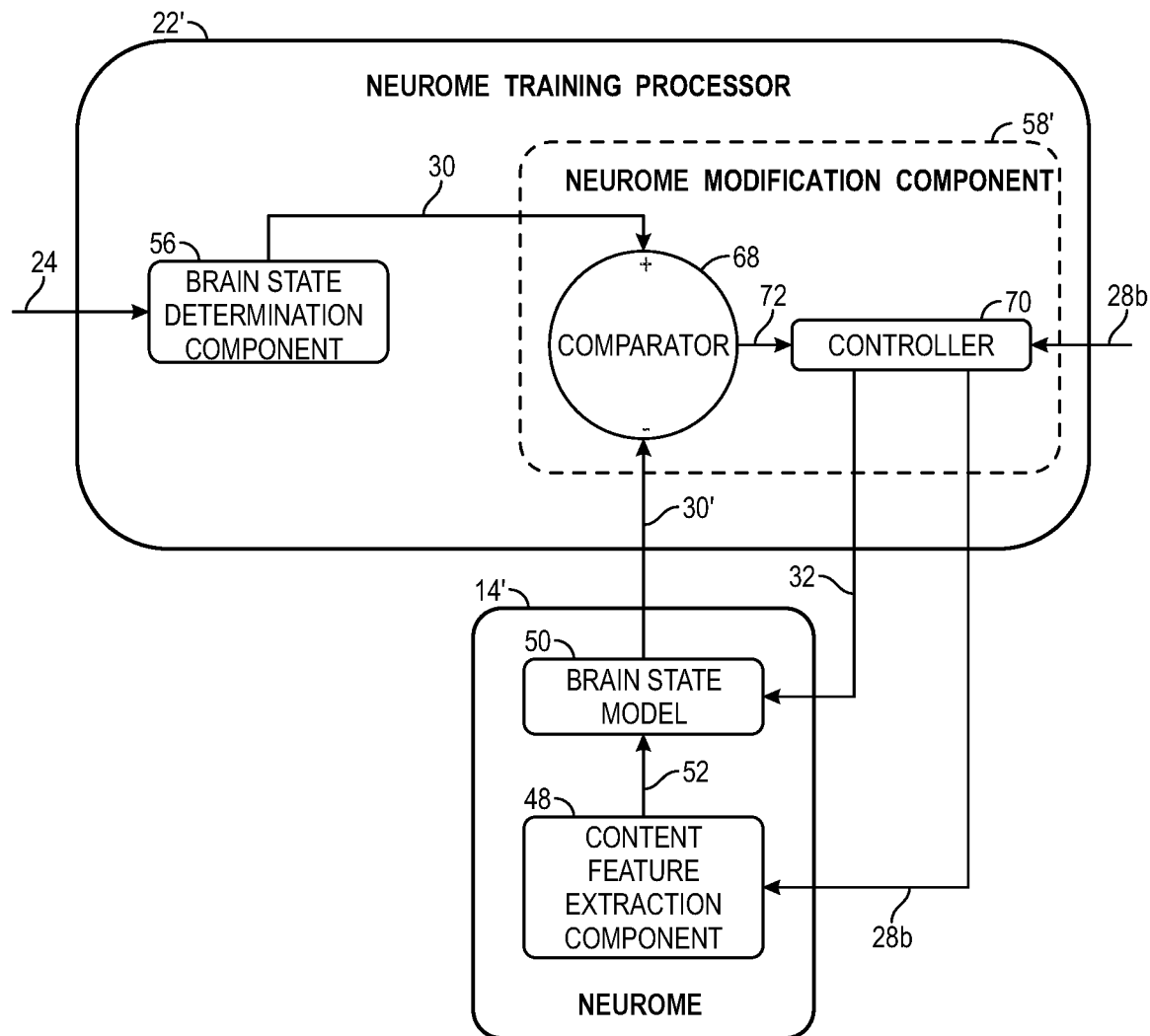
FIG. 6 is a block diagram of one specific implementation of a neurome training processor used in the neurome training system of FIG. 1.

Referring now to FIG. 6, one embodiment of a neurome modification component 58' that can be used in the neurome training processor 22 employs an on-line machine learning technique to train the neurome 14'. To this end, the neurome modification component 58' comprises a comparator 68 configured for sequentially comparing the brain states 30' (physiological brain states 30a' and/or mental brain states 30b') of the avatar 12' output by the neurome 14' and the brain states 30 (physiological brain states 30a and/or mental brain states 30b) of the user 12 determined by the brain state determination component 56, and outputting error signals 72. In the illustrated embodiment, the determined brain states 30 of the user 12 output by the brain state determination component 56 and the brain states 30' of the avatar 12' output by the neurome 14' are quantified, such that the error signals 72 sequentially output by the comparator 68 are representative of the respective differences between the determined brain states 30 of the user 12 output by the brain state determination component 56 and the brain states 30' of the avatar 12' output by the neurome 14'. The determined brain states 30 of the user 12 output by the brain state determination component 56 and the brain states 30' of the avatar 12' output by the neurome 14' may be physiological brain states, mental brain states, or both, and thus, the neurome modification component 58' can be used on any of the neurome modification components 58a-58d illustrated with reference to FIGS. 2-5. However, the type of determined brain states 30 of the user 12 output by the brain state determination component 56 and the type of brain states 30' of the avatar 12' output by the neurome 14' should match each other.

The neurome modification component 58' further comprises a controller 70 configured for sequentially inputting the digital stimulus instances 28b into the neurome 14', such that the neurome 14' sequentially outputs the brain states 30' of the avatar 12', and in particular, sequentially inputs the digital stimulus instances 28b into the content feature extraction component 48, which extracts and sequentially outputs vectors of content features 52 (one vector of content features 52 for each digital stimulus instance 28b) into the brain state model 50, which in turn outputs the brain states 30' of the avatar 12'. The comparator 68 then sequentially compares the brain states 30' of the avatar 12' to the brain states 30 of the user 12 determined by the brain state determination component 56, thereby yielding a series of error signals 72. For each comparison, the controller 70 is further configured for generating and outputting a control signal 32 that modifies the neurome 14' in a manner that is predicted to minimize the error signals 72, i.e., in a manner that determined brain state 30' output by the avatar 14' in response to a subsequent input of the digital instance stimulus 28b substantially matches the determined brain state 30 of the user 12 output by the brain state determination component 56.

Figure 7:
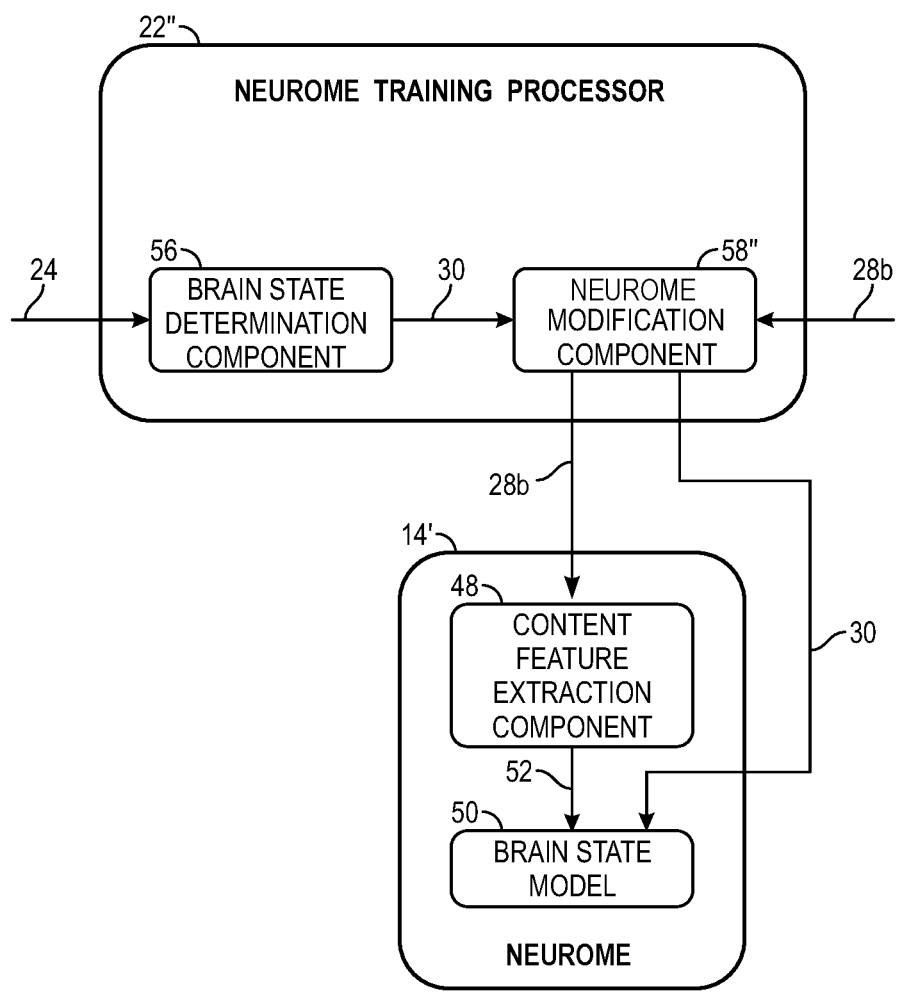
FIG. 7 is a block diagram of another specific implementation of a neurome training processor used in the neurome training system of FIG. 1.

Referring now to FIG. 7, another embodiment of a neurome modification component 58" that can be used in the neurome training processor 22 employs an off-line machine learning technique to train the neurome 14'. Conceptually, the neurome modification component 58" can be considered to be a specific embodiment of the neurome modification component 58' illustrated in FIG. 6, the difference being that, instead of the brain state comparison and error generation functions previously performed by the neurome modification component 58', these functions are illustrated as being performed by a machine learning algorithm associated with the brain state model 50. The brain state model 50 of the neurome 14' in this case comprises a regression model, such as, e.g., deep neural network, which has a first input for receiving vectors of content features 52 and a second input for receiving vectors of brain state features 30. Machine leaning algorithm can also include, e.g., Gradient Descent, where a group of a random subset of the whole training data (which consist of all of the inputs (e.g., the extracted content features 52 of the digital stimuli instances 28b and the determined brain states 30 of the user 12) and all of the outputs (e.g., the determined brain states 30' of the avatar 12')) are used to adjust the parameters, then another random subset is used to adjust the parameters, until the difference is less and less. The processing of the data in this fashion takes place inside the brain state model 50. Not all machine leaning methods use Gradient Descent, but known machine leaning algorithms adjust parameters with an optimizer, e.g., stochastic gradient descent, Newtonian methods, matrix inversion (such as in least squares fitting). The brain state model 50 can include an optimization component and the optimization component takes the whole input/output data and an optimization algorithm and it optimized the parameters of the brain state model 50.

The determined brain states 30 (physiological brain states 30a and/or mental brain states 30b) of the user 12 output by the brain state determination component 56 and the brain states 30' (physiological brain states 30a' and/or mental brain states 30b') of the avatar 12' output by the neurome 14' preferably at least include physiological brain states, each of which can yield a vector of brain state features 30, although the determined brain states 30 of the user 12 may also include mental brain states that may yield at least one feature that can be included in the vector of brain state features 30. Thus, the determined brain states 30 of the user 12 output by the brain state determination component 56 and the brain states 30' of the avatar 12' output by the neurome 14' may include physiological brain states 30a or a combination of physiological brain states 30a and mental brain states 30b, and thus, the neurome modification component 58" can be used on any of the neurome modification components 58b-58d illustrated with reference to FIGS. 2-5. However, the type or combination of types of determined brain states 30 of the user 12 output by the brain state determination component 56 and the type or combination of types of brain states 30' of the avatar 12' output by the neurome 14' should match each other.

For an entire set of training data (i.e., all of the digital instances 28b of the stimuli 28 output by the stimulus conditioning pre-processor 20 and all of the determined brain states 30a output by the brain state determination processor 56 in response to the analog instances 28a of the stimuli 28 peripherally input into the brain 14 of the user 12), the neurome modification component 58" is configured for inputting the digital stimulus instances 28b into the content feature extraction component 48 of the neurome 14', which extracts content features from the digital stimulus instances 28b and outputs the vectors of content features 52 into the first input of the brain state model 50, and inputting the vectors of brain states 30 into the second input of the brain state model 50.

As briefly discussed above, the configuration of the stimulus conditioning pre-processor 20 of the neurome training system 10 of FIG. 1 will depend on the nature of the source of content 26.

Figure 8:
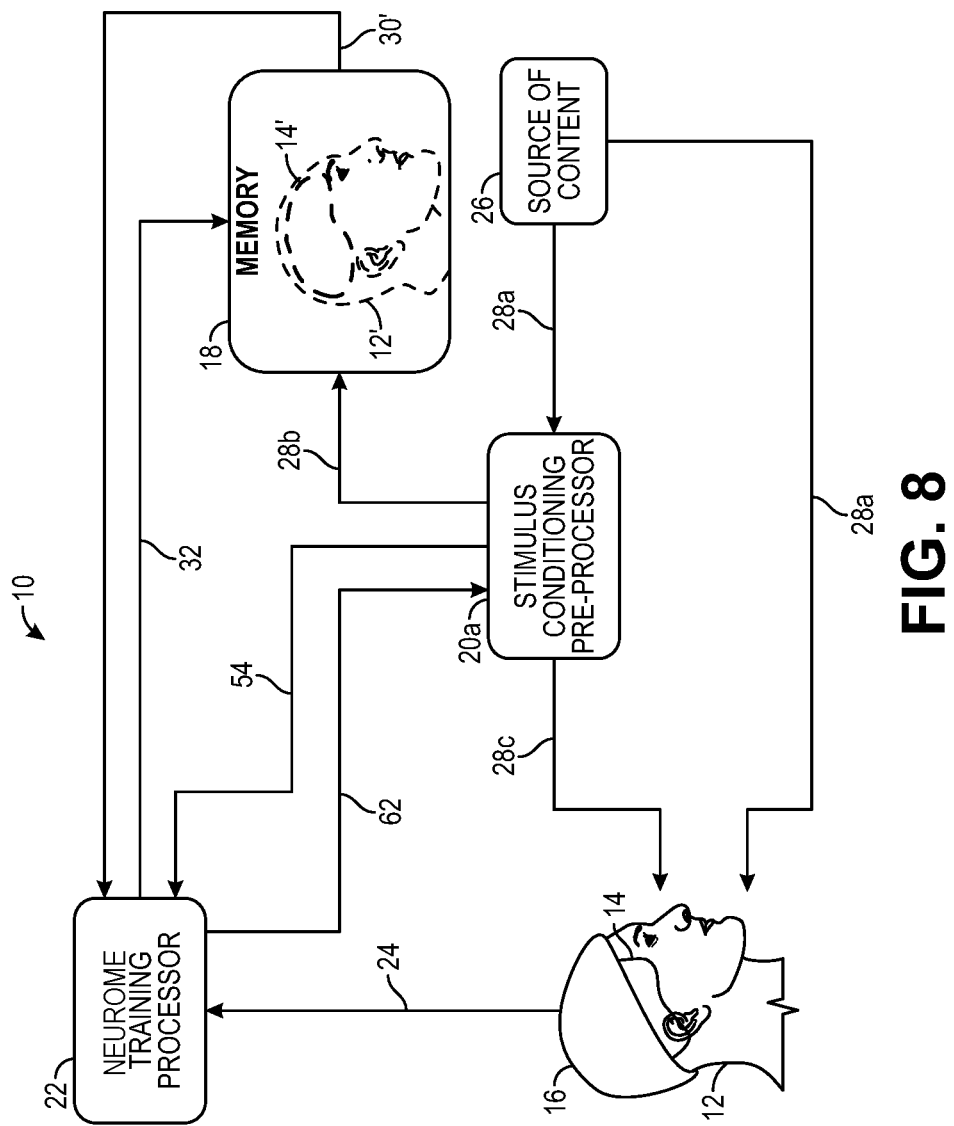
FIG. 8 is a block diagram of one specific implementation of a stimulus conditioning pre-processor used in the braining training system of FIG. 1.

In one embodiment illustrated in FIG. 8, sources of content 26 reside in the real-world (meaning that the source of content 26 can be experienced by the user 12 without any intervening processing). In this case, one embodiment of a stimulus conditioning pre-processor 20a may be configured for acquiring the analog stimulus instances 28a from the real-world sources of content 26 and generating digital stimulus instances 28b based on the acquired analog instances 28a. Thus, the stimulus conditioning pre-processor 20a operates directly on (e.g., digitizing) the analog stimulus instances 28a. In this case, the stimulus conditioning pre-processor 20 may, e.g., take the form of a video recorder, a camera, or an optical character recognition (OCR) device for digitizing analog stimulus instances 28a that are concurrently peripherally input into the brain 14 of the user 12 via sight, or an audio recorder for digitizing analog stimulus instances 28a that are concurrently peripherally input into the brain 14 of the user 12 via hearing.

Figure 9:
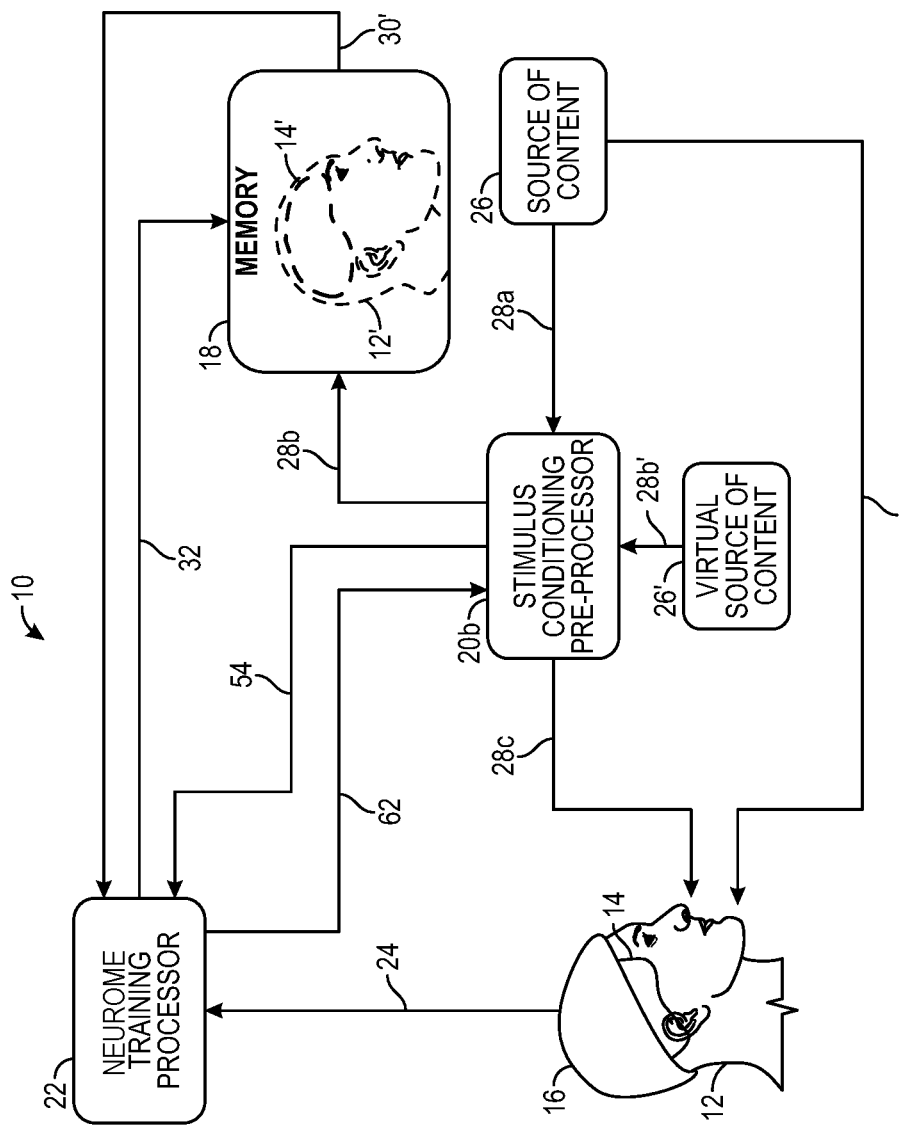
FIG. 9 is a block diagram of another specific implementation of a stimulus conditioning pre-processor used in the braining training system of FIG. 1.

Referring now to FIG. 9, another embodiment of a stimulus conditioning pre-processor 20b may be configured for acquiring analog stimulus instances 28a from the real-world source of content 26 and generating digital stimulus instances 28b based on the acquired analog stimulus instance 28a, but without operating directly on the analog stimulus instances 28a. In particular, the stimulus conditioning pre-processor 20b may be configured for identifying the real-world sources of content 26 and acquiring digital stimulus instances 28b' from separate sources of content 26'. For example, if the real-world source of content 26 is a food product, such as a hamburger, the stimulus conditioning pre-processor 20 may generate a digital stimulus instance 28b, or otherwise acquire a pre-existing digital stimulus instance 28b', from a corresponding virtual source of content 26' that characterizes a taste of the hamburger in the form of a taste or ingredient profile containing a combination of salty, savory, bitter, sour, and sweet characteristics. As another example, if the real-world source of content 26 is a type of automobile, such as a Ferrari, the stimulus conditioning pre-processor 20 may generate a digital stimulus instance 28b, or otherwise acquire a pre-existing digital stimulus instance 28b', from a corresponding virtual source of content 26' that characterizes a driving experience of the Ferrari in the form of a driving profile containing a combination of quick accelerations and high-speed turns, or other types of driver experiences.

For either of the embodiments illustrated in FIG. 8 or FIG. 9, the stimulus conditioning pre-processor 20a or 20b may optionally be configured for modulating (e.g., modifying, conditioning, or supplementing) the analog stimulus instance 28a acquired from the source of content 26 with additional an analog stimulus 28c, and then generating the digital stimulus instance 28b from the modified, conditioned, or supplemented analog stimulus instance 28a, 22c. For example, the stimulus conditioning pre-processor 20a or 20b may add programmed tones to analog stimulus instances 28a that include audio, modulating analog stimulus instances 28a that include video with ambient flashing, haptic sensations, digital or special effects (e.g., using an augmented reality (AR) system), etc.

Figure 10:
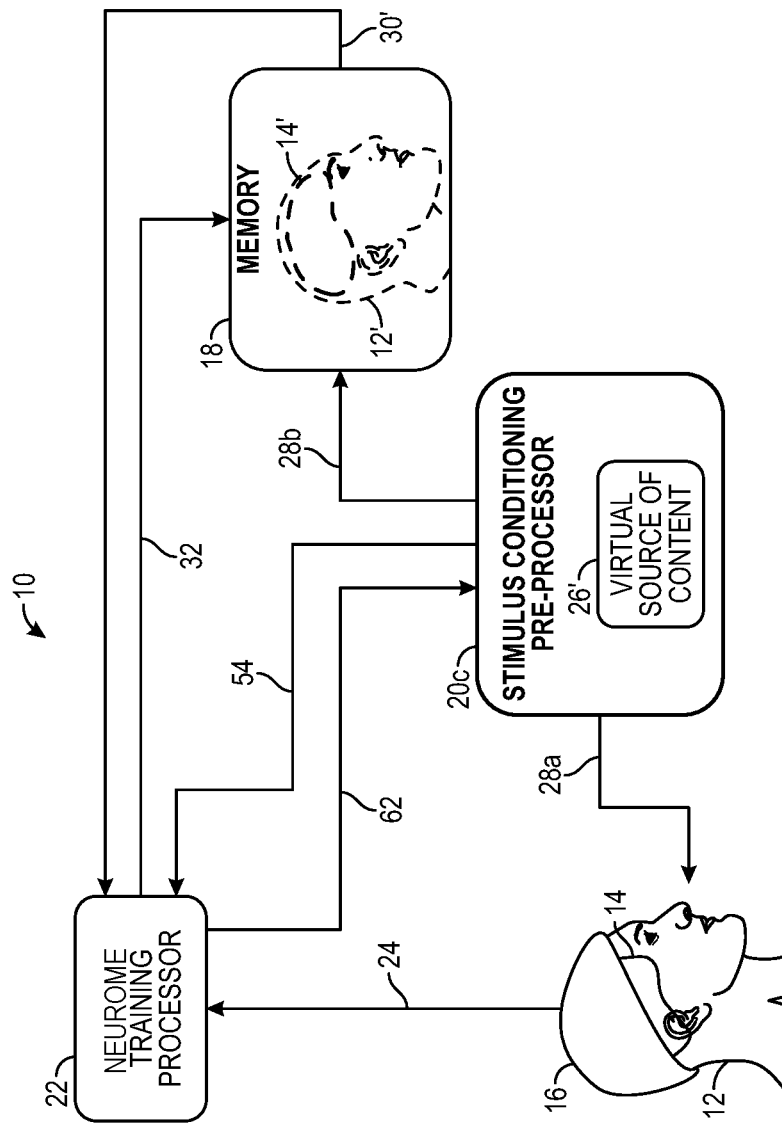
FIG. 10 is a block diagram of another specific implementation of a stimulus conditioning pre-processor used in the braining training system of FIG. 1.

Referring now to FIG. 10, virtual sources of content 26' may reside in or can be acquired by another embodiment of a stimulus conditioning pre-processor 20c, itself, in which case, the stimulus conditioning pre-processor 20c may be configured for generating digital stimulus instances 28b directly from the virtual sources of content 26', and transforming the digital stimulus instances 28b into analog stimulus instances 28a, which can then be peripherally input into the brain 14 of the user 12. For example, the stimulus conditioning pre-processor 20c may take the form of a video player, audio player, or any other device capable of storing a virtual source of content 26'. In this embodiment, the neurome training processor 22 may be configured for controlling the virtual source of content 26' within the stimulus conditioning pre-processor 20, such that the analog stimulus instances 28a peripherally input into the brain 14 of the user and the digital stimulus instances 28b input into the processor 22 can be selected or modified accordingly.

For all of the embodiments illustrated in FIGS. 8-10, the stimulus conditioning pre-processor 22a-22c, under control of the neurome training processor 22 via control signals 62, inputs the digital stimulus instances 28b of the stimuli 28 into the neurome 14' during training of the neurome 14'. Any of these stimulus conditioning pre-processors 22a-22c may optionally be configured for generating meta data 54 characterizing the real-world sources of content 26, and conveying the meta data 54 to the neurome training processor 22 to facilitate training of the neurome 14', as discussed above with respect to FIG. 1.

Although the digital instances 28b of the stimuli 28 input into the neurome 14' have been described as raw data or information, the digital instances 28b of the stimuli 28 input into the neurome 14' may be, or may comprise, meta data 54 characterizing the sources of content 26, in which case, the neurome 14' need not include a content feature extraction component 48, since the content features of the stimuli 28 have essentially been extracted by the stimulus conditioning processor 20 or otherwise already provided to the stimulus conditioning pre-processor 20 in the form of meta data 54.

It should be appreciated that although the stimulus conditioning pre-processor 20 and neurome training processor 22 are illustrated as separate and distinct processors for purposes of clarity, it should be appreciated that the functionality (or any portions thereof) of the stimulus conditioning pre-processor 20 and neurome training processor 22 may be merged into a single processor. Furthermore, although each of the stimulus conditioning pre-processor 20 and neurome training processor 22 is illustrated as a single processor, the functionality of each of the stimulus conditioning pre-processor 20 or the neurome training processor 22 may be distributed amongst several processors. It should also be appreciated that those skilled in the art are familiar with the term "processor," and that it may be implemented in software, firmware, hardware, or any suitable combination thereof.

Having described the structure and function of the neurome training system 10, one exemplary method 200 of operating the neurome training system 10 to train a neurome 14' of an avatar 12' will now be described with reference to FIG. 19.

The method 200 comprises storing (in the memory 30) a neurome 14' of an avatar 12' of the user 12, which may begin as a generic model of a typical brain (step 202). The method 200 further comprises selecting or modifying one of a plurality of different sources of content 26 (via the stimulus conditioning pre-processor 20 under control of the training control component 60 of the neurome training processor 22) (step 204). As examples, the different sources of content 26 may all be in the same genre, e.g., one of a genre of movies, a genre of songs, a genre of books, a genre of household appliances, a genre of automobiles, a genre of foods, a genre of drinks, a genre of artwork, or sources of consumable chemical substances etc., and the analog instance of each of the different stimuli 28 may be modulated by providing ambient flashing, haptic sensations, digital or special effects, etc. The method 200 further comprises optionally modulating (via the stimulus conditioning pre-processor 20) an analog instance 28a of a stimulus 28 from the selected or modified source of content 26 (step 206). In alternative methods, the analog stimulus instance 28a is not modulated.

The method 200 further comprises peripherally inputting the modulated (or unmodulated) an analog stimulus instance 28a into the brain 14 of the user 12 (step 208), and detecting neural activity 24 of the user 12 (via the brain interface assembly 16) in response to the modulated (or modulated) analog stimulus instances 28a peripherally input into the brain 14 of the user 12 (step 210). The method 200 optionally comprises acquiring peripheral physiological signals 40 (via the sensors 38) and conscious input 44 from the user 12 (via the user interface 42) in response to the peripheral input of the analog stimulus instances 28a into the brain 14 of the user 12, and/or the personal profile 46 of the user 12 (step 212).

The method 200 further comprises determining a brain state 30 of the user 12 (via the brain state determination component 56 of the neurome training processor 22) at least partially based on the neural activity 24 detected in response to the analog stimulus instance 28a, and optionally based on the acquired peripheral physiological signals 40, conscious input 44 from the user 12, and/or the personal profile 46 (step 214). The determined brain state 30 of the user 12 may, e.g., a physiological brain state 30a, a mental brain state 30b, or both.

For example, in the case of the neurome training processor 22a illustrated in FIG. 2, a physiological brain state 30a can be determined primarily based on the detected neural activity 24, optionally informed by the peripheral physiological functions of the user 12, e.g., heart rate, respiratory rate, blood pressure, skin conductivity, etc., extracted from the peripheral physiological signals 40. In the case of the neurome training processor 22b in FIG. 3, the determined brain state 30 may be a mental brain state 30b derived from the physiological brain state 30a, and optionally informed by peripheral physiological functions of the user 12, e.g., heart rate, respiratory rate, blood pressure, skin conductivity, etc., extracted from the peripheral physiological signals 40, the conscious input 44 from the user 12, and/or the personal profile 46 of the user 12. In the case of the neurome training processor 22c in FIG. 4 or the neurome training processor 22d in FIG. 5, the determine brain state 30 can include both a physiological brain state 30a and a mental brain state 30b. For example, a physiological brain state 30a can be determined primarily based on the detected neural activity 24, and the mental brain state 30b can be determined primarily on the conscious input 44 from the user 12, optionally informed by the peripheral physiological functions of the user 12, e.g., heart rate, respiratory rate, blood pressure, skin conductivity, etc., extracted from the peripheral physiological signals 40 and/or the personal profile 46 of the user 12.

The method 200 further comprises generating (via the stimulus conditioning pre-processor 20) a digital stimulus instance 28b from the selected or modified source of content 26 (step 216). In one embodiment, the selected or modified source of content 26 is real-world source of content, in which case, the analog stimulus instance 28a may be acquired from the real-world source of content 26, and the digital stimulus instance 28b may be generated based on the acquired analog stimulus instance 22, e.g., by digitizing the acquired analog instance 28a of each of the different stimuli 28 (see FIG. 7) or by identifying the acquired analog stimulus instance 28a, acquiring one of a different plurality of virtual sources of content 26', and generating the digital stimulus instance 28b from the selected or modified virtual source of content 26' that characterizes the acquired analog stimulus instance 28a (see FIG. 8). In another embodiment, the selected or modified source of content 26 is a virtual source of content 26', in which case, the digital stimulus instance 28b may be generated from the selected or modified virtual source of content 26', and the analog stimulus instance 26a may be generated from the generated digital stimulus instance 28b (see FIG. 9).

The method 200 further comprises generating meta data 54 characterizing the stimuli 28 (via the stimulus conditioning pre-preprocessor 20) (step 218), and in the case where the neurome 14' of the avatar 12 comprises multiple brain state models 50 and associated content feature extraction components 48, and logging the meta data 54 along with the determined brain state 30 (the physiological brain state 30a, the mental brain state 30b, or both) of the user 12 (via the training control component 60 of the neurome training processor 22) (step 220). The method 200 further comprises selecting one of the brain state models 50 based on the meta data 54 (via the training control component 60 of the neurome training processor 22) (step 222). For example, the multiple brain state models 50 are categories by different genres or even sub-genres (or species), the brain state model 50 having the genre or sub-genre that most closely matches the content characterized by the meta data 54 may be selected.

The method 200 further comprises inputting (via the neurome modification component 58 of the neurome training processor 22) the digital stimulus instance 28b (which may be raw data or meta data 54) into the neurome 14' (step 224), extracting content features 52 from the digital stimulus instance 28b characterizing the source of content 26 (via the content feature extraction component 48 of the neurome 14') (step 226) (if the digital stimulus instance 28b is raw data), and determining the brain state 30' (the physiological brain state 30a', the mental brain state 30b', or both) of the avatar 12' (via the selected brain state model 50 of the neurome 14') based on the extracted content features 52 (step 228).

The method 200 further comprising modifying (via the neurome training processor 22) the neurome 14', such that the determined brain state 30' (the physiological brain state 30a', the mental brain state 30b', or both) of the avatar 12' output by the neurome 14' in response to the same digital stimulus instance 28b substantially matches the determined brain state 30 (the physiological brain state 30a, the mental brain state 30b, or both) of the user 12 in response to the same analog stimulus instance 28a peripherally input into the brain 14 of the user 12 (step 230).

In the case of the neurome 14d' and the neurome training processor 22d illustrated in FIG. 5, the brain state model 50 of the neurome 14d' is modified, such that the determined physiological brain state 30a of the avatar 12' output by the brain state model 50 in response to the same digital stimulus instance 28b substantially matches the determined physiological brain state 30a of the user 12 in response to the same analog stimulus instance 28a peripherally input into the brain 14 of the user 12. Furthermore, the look-up table 66 of the neurome 14' is modified by correlating the physiological brain states 30a and the mental brain states 30b of the user 12 determined by the brain state determination component 56d (via the neurome modification component 58d of the neurome training processor 22d), and storing the correlated physiological brain states 30a and mental brain states 30b as correlated reference physiological brain states and mental brain states described above in the look-up table 66.

The method 200 comprises determining if the selected brain state model 50 of the neurome 14' has been fully trained (step 232). If the selected brain state model 50 of the neurome 14' has been fully trained, the selected brain state model 50 is deemed as such (step 234). It can be assumed that the fully trained neurome 14' can predict a brain state 30 of the user 12 in response to the user 12 peripherally receiving an analog instance 28a of a stimulus 28 that is different from, but in the same genre as, the stimuli 28 on which the neurome 14' has been trained. The method 200 then comprises selecting a new genre of sources of content on which another brain state model 50 of the neurome 14' will be trained (step 236), and returning to step 204 to train the neurome 14' of the avatar 12 on a source of content 26 in this selected genre of sources of content 26.

If the selected brain state model 50 of the neurome 14' has not been fully trained, the method 200 further comprises determining the source of content 26 to be modified or selected based on the logged meta data 54 and determined brain states 30 of the user 12 (via the training control component 60 of the neurome training processor 22) (step 238), and returning to step 204 to train the neurome 14' of the avatar 12 on the next source of content 26. Preferably, the newly modified or selected source of content 26 is in the same genre as the previously modified or selected source of content 26. Steps 204-234 are repeated until the selected brain state model of the neurome 14' has been fully trained on the different stimuli 28. The method 200 may be repeated for additional brain state models 50 of the neurome 14' to be trained.

Figure 20:
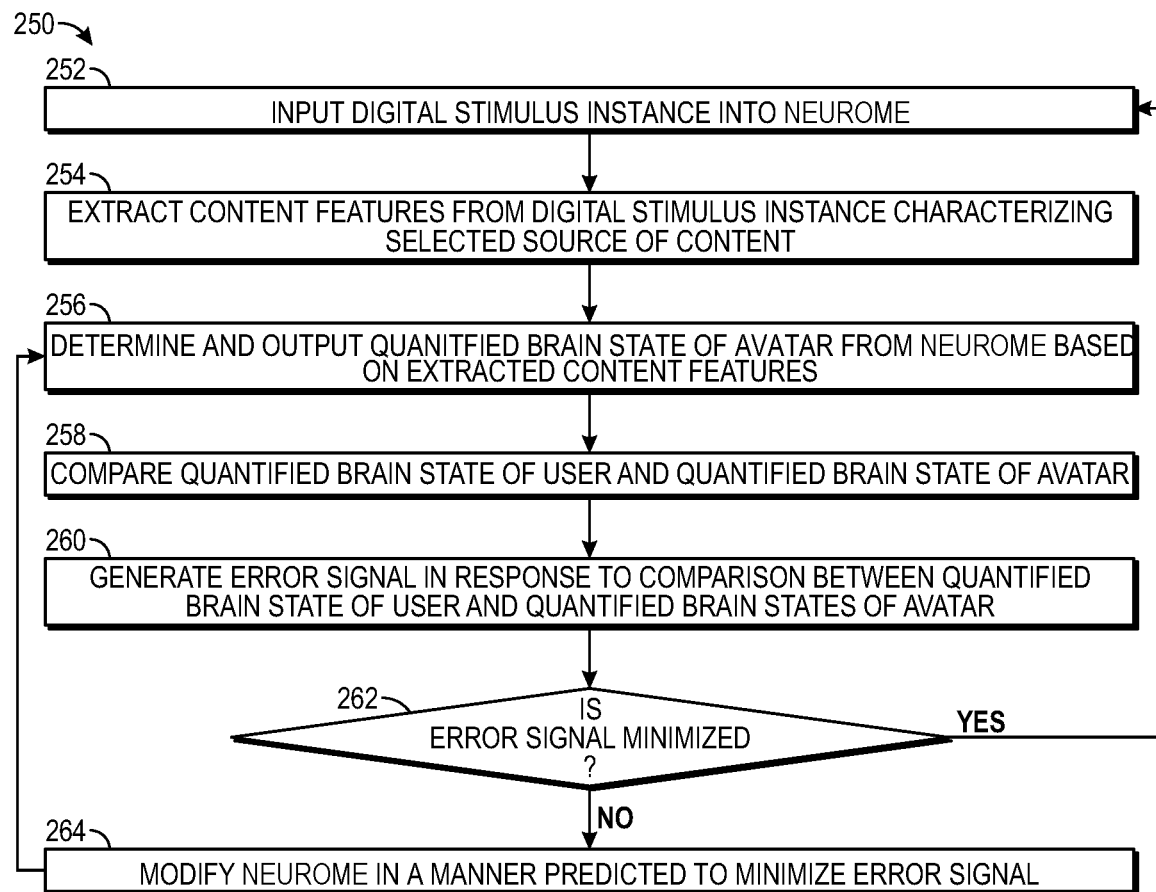
FIG. 20 is a flow diagram illustrating one method of operating the neurome training processor of FIG. 6 to train a neurome.

Referring to FIG. 20, one exemplary method 250 of using the neurome modification component 58' illustrated in FIG. 6 to modify the neurome 14' will now be described. The method 250 assumes that the brain state 30 of the user 12 has already been determined in response to the analog stimulus instance 28a peripherally input into the brain 14 of the user 12, and that the digital stimulus instance 28b has already been generated in accordance with the method 200.

The method 250 comprises inputting the digital stimulus instance 28b into the neurome 14' (via the neurome modification component 58' of the neurome training processor 22') (step 252), extracting content features 52 from the digital stimulus instance 28b characterizing the source of content 26 (via the content feature extraction component 48 of the neurome 14') (step 254), and determining the brain state 30' (the physiological brain state 30a', the mental brain state 30b', or both) of the avatar 12' (via the brain state model 50 of the neurome 14') based on the extracted content features 52 (step 256). It is assumed that, at this point, the determined brain state 30 of the user 12 and the determined brain state 30' of the avatar 12' are both quantifiable. For example, the determined brain state 30 of the user 12 and the determined brain state 30' of the avatar 12' may each be represented by a vector of quantifiable features.

The method 250 further comprises comparing the quantified brain states 30 of the user 12 and the quantified brain states 30' of the avatar 12' (step 258), generating an error signal 72 in response to the comparison between the quantified determined brain state 30 of the user 12 and the quantified determined brain state 30' of the avatar 12' (step 260), and determining if the error signal 72 has been minimized (step 262). If the error signal 72 has not been minimized, then the method 250 further comprises modifying the neurome 14' (i.e., the brain state model 50) in a manner that is predicted to minimize the error signal 72 (step 264), and returning to step 256, where the brain state 30' (the physiological brain state 30a', the mental brain state 30b', or both) of the avatar 12' (via the brain state model 50 of the neurome 14') is again determined based on the extracted content features 52. Steps 256-264 are then repeated to determine whether the error signal 72 has been minimized. This iterative process continues until the error signal 72 has been minimized, at which point, the quantified determined brain state 30' output by the neurome 14' substantially matches the quantified determined brain state 30 of the user 12. The method 250 can then be repeated to train the neurome 14' on additional stimuli 28.

Figure 21:
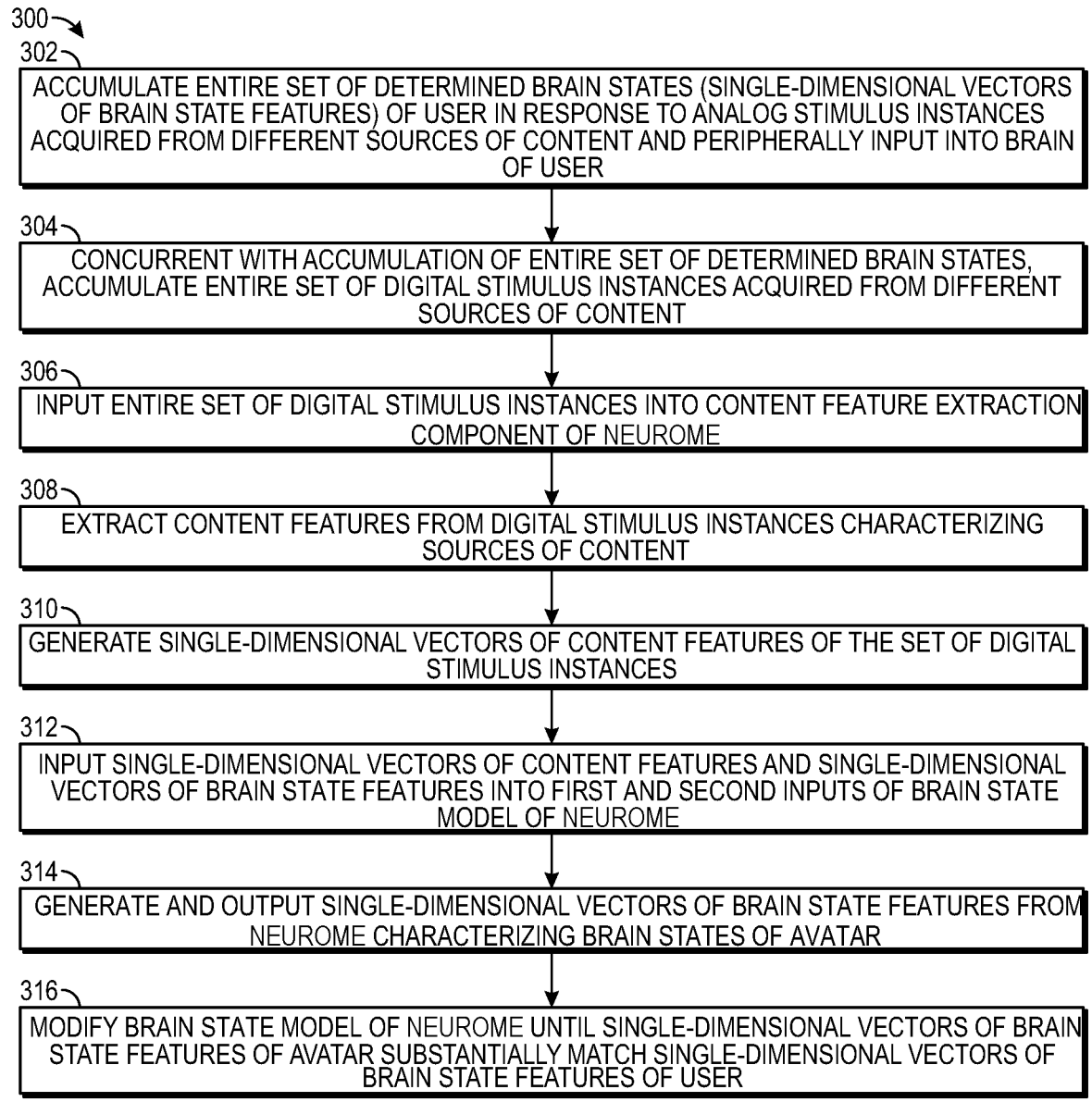
FIG. 21 is a flow diagram illustrating one method of operating the neurome training processor of FIG. 7 to train a neurome.

Referring to FIG. 21, one exemplary method 300 of using the neurome modification component 58" illustrated in FIG. 7 to modify the neurome 14' will now be described.

The method 300 comprises accumulating an entire set of determined brain states 30 of the user 12 (via the brain state determination component 56 of the neurome training processor 22") in response to analog stimulus instances 28a acquired from different sources of content 26 and peripherally input into the brain 14 of the user 12 (step 302). In the illustrated embodiment, the set of determined brain states 30 of the user 12 take the form of single-dimensional vectors of brain state features, each single-dimensional vector of which includes features of a physiological brain state 30a of the user 12 and optionally one or more features of a mental brain state 30b of the user 12). Concurrently with the accumulation of the vectors of brain state features 30, the method 300 further comprises accumulating an entire set of digital stimulus instances 28b (via the brain state determination component 56 of the neurome training processor 22") acquired from the sources of content 26 and from which the analog instances 28a have been peripherally input into the brain 14 of the user (step 304).

The method 300 further comprises inputting the entire set of digital stimulus instances 28b into the content feature extraction component 48 of neurome 14' (via the neurome modification component 58" of the neurome training processor 22") (step 306), extracting content features 52 from the entire set of digital stimulus instances 28b characterizing the sources of content 26 (step 308), and generating single-dimensional vectors of the extracted content features 52 of the set of digital stimulus instances 28b (via the content feature extraction component 48 of the neurome 14') (step 310). The method 300 further comprises concurrently inputting the single-dimensional vectors of content features 52 into the first input of the brain state model 50, and inputting the single-dimensional vectors of brain state features 30 into the second input of the brain state model 50 (step 312). The method 300 further comprises generating and outputting single-dimensional vectors of brain state features 30' from the brain state model 50 of the neurome 14' characterizing the brain states of the avatar 12' (step 314). The brain state model 50 is modified until the vectors of brain state features 30' of avatar 12' output by the brain state model 50 substantially match the vectors of brain states features 30 of the user 12 input into the brain state model 50 (step 316).

Figure 11:
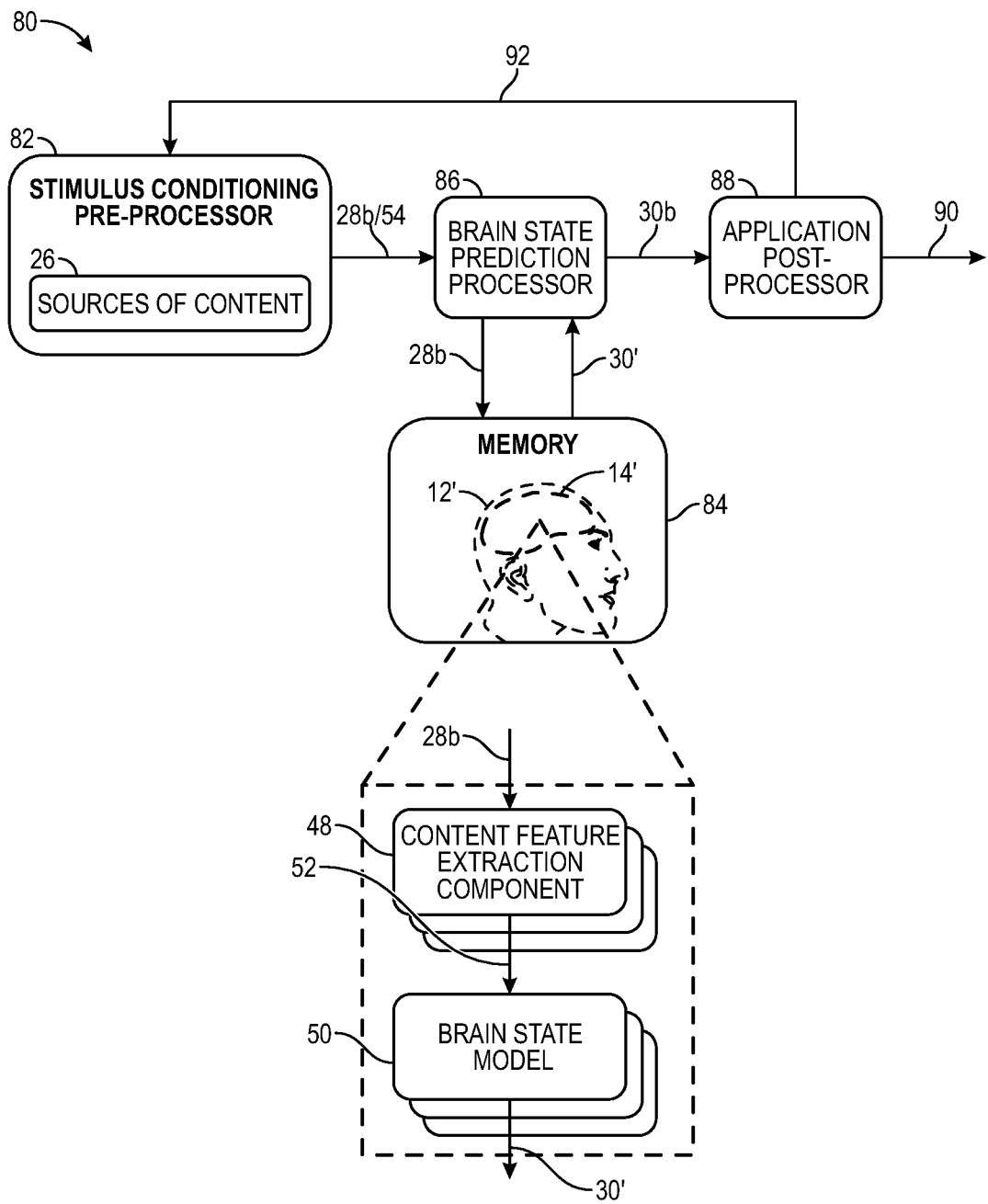
FIG. 11 is a block diagram of one embodiment of a brain emulation system constructed in accordance with the present inventions.

Referring now to FIG. 11, one embodiment of a brain emulation system 80 for using the neurome 14' to emulate the brain 14 of the user 12 will now be described.

The brain emulation system 80 comprises a stimulus conditioning pre-processor 82, a memory 84, a brain state prediction processor 86, and an application post-processor 88.

The stimulus conditioning pre-processor 82 is configured for storing or otherwise acquiring at least one genre of sources of content 26 (e.g., a multitude of digital books, or a multitude of movies, a multitude of automobile types, a multitude of foods, a multitude of drinks, etc.). The stimulus conditioning pre-processor 82 is configured for outputting digital stimulus instances 28*b* from the genre of sources of content 26, and optionally meta data 54 characterizing the sources of content 26.

The memory 84 is configured for storing the neurome 14' associated with the user 12. It is assumed that the neurome 14' has been fully trained on at least one genre of sources of content 26, such that the neurome 14' outputs brain states 30' in response digital instances 28*b* of the stimuli 28 input from the genre of sources of content 26 that fairly predicts the brain states 30 of the user 12 had the analog stimulus instances 28*a* been peripherally input into the brain 14 of the user 12.

In the case where the neurome 14' comprises a plurality of brain state models 50 and associated content feature extraction components 48, as illustrated in FIG. 1, the stimulus conditioning pre-processor 82 may be configured for generating and outputting meta data 54 based on an analysis of the stimuli 28, or if the source of content 26 has already associated meta data 54 with the stimuli 28, by simply acquiring the meta data 54 without an analysis of the stimuli 28.

The brain state prediction processor 86 is configured for inputting the digital stimulus instances 28*b* (which may be raw data or the metal data 54) received from the stimulus conditioning pre-processor 82 into the neurome 14', such that the neurome 14' outputs a brain state 30' (physiological brain state 30*a'*, mental brain state 30*b'*, or both) of the avatar 12'. In particular, the brain state prediction processor 86 is configured for inputting the digital stimulus instances 28*b* into the content feature extraction component 48 of the neurome 14', which extracts content features 52 from the digital instances 28*b* of the stimuli 28 characterizing the sources of content 26. The brain state model 50 then outputs the determined brain states 30' of the avatar 12' in response to an input of the extracted content features 52. In the case where the neurome 14' comprises a plurality of brain state models 50 and associated content feature extraction components 48, as illustrated in FIGS. 1 and 11, the brain state prediction processor 86 may be further configured for selecting which of the brain models 50 in which the digital stimulus instances 28*b* will be input based on meta data 54 acquired from the stimulus conditioning pre-processor 82.

The brain state prediction processor 86 is configured predicting mental brain states 30*b* of the user 12 had the analog instances 28*a* of the same stimuli 28 been peripherally input into the brain 14 of the user 12. It is preferred that the genre of the sources of content 26 from which the digital stimulus instances 28*b* are input by the brain state prediction processor 86 into the neurome 14' be the same genre of sources of content 26 from which the digital stimulus instances 28*b* were used to train the neurome 14', as described above with respect to FIGS. 8-10, although it is preferred that at least some of the digital stimulus instances 28*b* input by the brain state prediction processor 86 into the neurome 14' be different from the digital stimulus instances 28*b* used to train the neurome 14', so that the neurome 14' can properly emulate the brain 14 of the user 12.

If the neurome 14' takes the form of the neurome 14*a'* illustrated in FIG. 2, the determined brain states 30' output by the neurome 14*a'* will be physiological brain states 30*a'*, in which case, the brain state prediction processor 86 may be further configured for predicting mental brain states 30*b* of the user 12 based on the physiological brain states 30*a'* of the avatar 12' output by the neurome 14*a'*, and outputting these predicated mental brain states 30*b*. For example, the brain state prediction processor 86 may employ any of the techniques used by the brain state determination component 56*b* of the neurome training processor 22*a* in determining the mental brain states 30*b* of the user 12 from the physiological brain states 30*a*. The predication processor 86 can be calibrated for the user 12 in the same manner that the brain state determination component 56*b* was calibrated for the user 12 during the training of the neurome 14*a'*.

If the neurome 14' takes the form of the neurome 14*b'* illustrated in FIG. 3, the determined brain states 30' output by the neurome 14*b'* will be mental brain states 30*b'*, in which case, the brain state prediction processor 86 simply outputs the mental brain states 30*b'* from the neurome 14*b'* to the application post-processor 108 as the predicted mental states 30*b* of the user 12 without modification.

If the neurome 14' takes the form of the neurome 14*c'* illustrated in FIG. 4 or the neurome 14*d'* illustrated in FIG. 5, the determined brain states 30' output by the neurome 14*c'* or neurome 14*d'* will be physiological brain states 30*a'* and mental brain states 30*b'*, in which case, the brain state prediction processor 86 outputs the mental brain states 30*b'* from the neurome 14*c'* or neurome 14*d'* to the application post-processor 108 as the predicted mental states 30*b* of the user 12 without modification, and utilizes the physiological brain states 30*a'* output by the neurome 14*c'* or neurome 14*d'* for other purposes (e.g., correlate with clinical outcomes or predict future or current behavior, predict current or future preferences, predict future brain states (as opposed to current brain states), predict long-term impressions, or predict likelihood of actions of the user 12). With regard to the neurome 14*d'*, the mental brain state determination component 54 accesses the look-up table 66 containing the reference physiological brain states to which reference mental brain states are respectively associated, matches each physiological brain state 30*a'* output by the brain state model 50 to a reference mental brain state in the look-up table 66, and outputs the reference mental brain state associated with the matched reference physiological brain state, along with the physiological brain state 30*a'* output by the brain state model 50, as the physiological brain states 30*a'* and mental brain states 30*b'* of the avatar 12'.

The application post-processor 88 is configured for processing the predicted mental brain states 30*b* of the user 12 output by the brain state prediction processor 86, generating a practical result 90 based on the processed predicted mental brain states 30*b* of the user 12, and determining if the practical result 90 is desirable. If the practical result 90 desirable, the application post-processor 108 is configured for outputting the practical result 90 to the user 12. If the practical result 90 is not desirable, the application post-processor 88 is configured for outputting control signals 92 to the stimulus conditioning pre-processor 82 to select or modify the sources of content 26 from which the stimulus conditioning pre-processor 82 generates the digital instance 28*b* of each of the stimuli 28 in a manner that is predicted to achieve a desirable practical result 90.

As one example, the application post-processor 88 may be designed to market or present, i.e., using different types of website media, a particular set of goods (e.g., automobiles) to the user 12. In order to present the most relevant automobiles to the user 12, the application post-processor 88 may down select from all of the available automobile models (e.g., 1000 models) to a handful of automobile models (e.g., 5 models) that are more relevant to the user 12, and present the down-selected automobile models as the practical result 90 to the user 12.

To this end, the application post-processor 88 may instruct the stimulus conditioning pre-processor 82 to output digital instances 28*b* of, for example, 1000 different sources of content 26 in form of any combination of images, sounds, acceleration levels, etc. of automobiles. The brain state prediction processor 86 may then input the digital instances 28*b* of 1000 stimuli 28 into the neurome 14', such that the neurome 14' outputs 1000 brain states 30' of the avatar 12'. The brain state prediction processor 86 may then predict 1000 mental brain states 30*b* of the user 12 based on the 1000 brain states 30' output by the neurome 14'. The application post-processor 88 may then examine the predicted mental brain states 30*b* of the user 12 associated with the 1000 stimuli 28, and determine the stimuli 28 (i.e., images, sounds, acceleration levels, etc. of the automobiles) that the user 12 most likes. For example, the automobiles corresponding to stimuli 28 that evoke the brain states 30' of the avatar 12' from which the five happiest predicted mental brain states 30*b* of the user 12 are derived may be identified and subsequently presented to the user 12. Alternatively, the automobiles corresponding to stimuli 28 that evoke the brain states 30' of the avatar 12' from which the five most negative predicted mental brain states 30*b* of the user 12 are derived may be identified and subsequently presented to the user 12. As another example, the practical result 90 presented to the user 12 by the application post-processor 88 may be a suggestion of a source of content 26 that has not been previously presented to the user 12.

It should be appreciated that although the stimulus conditioning pre-processor 82, brain state prediction processor 86, and application post-processor 88 are illustrated as separate and distinct processors for purposes of clarity, the functionality (or any portions thereof) of the stimulus conditioning pre-processor 82, brain state prediction processor 86, and application post-processor 88 may be merged into less processors or even a single processor. Furthermore, although each of the stimulus conditioning pre-processor 82, brain state prediction processor 86, and application post-processor 88 may be configured as a single processor, the functionality of each of the stimulus conditioning pre-processor 82, brain state prediction processor 86, and application post-processor 88 may be distributed amongst several processors. It should also be appreciated that those skilled in the art are familiar with the term "processor," and that it may be implemented in software, firmware, hardware, or any suitable combination thereof.

Figure 22:
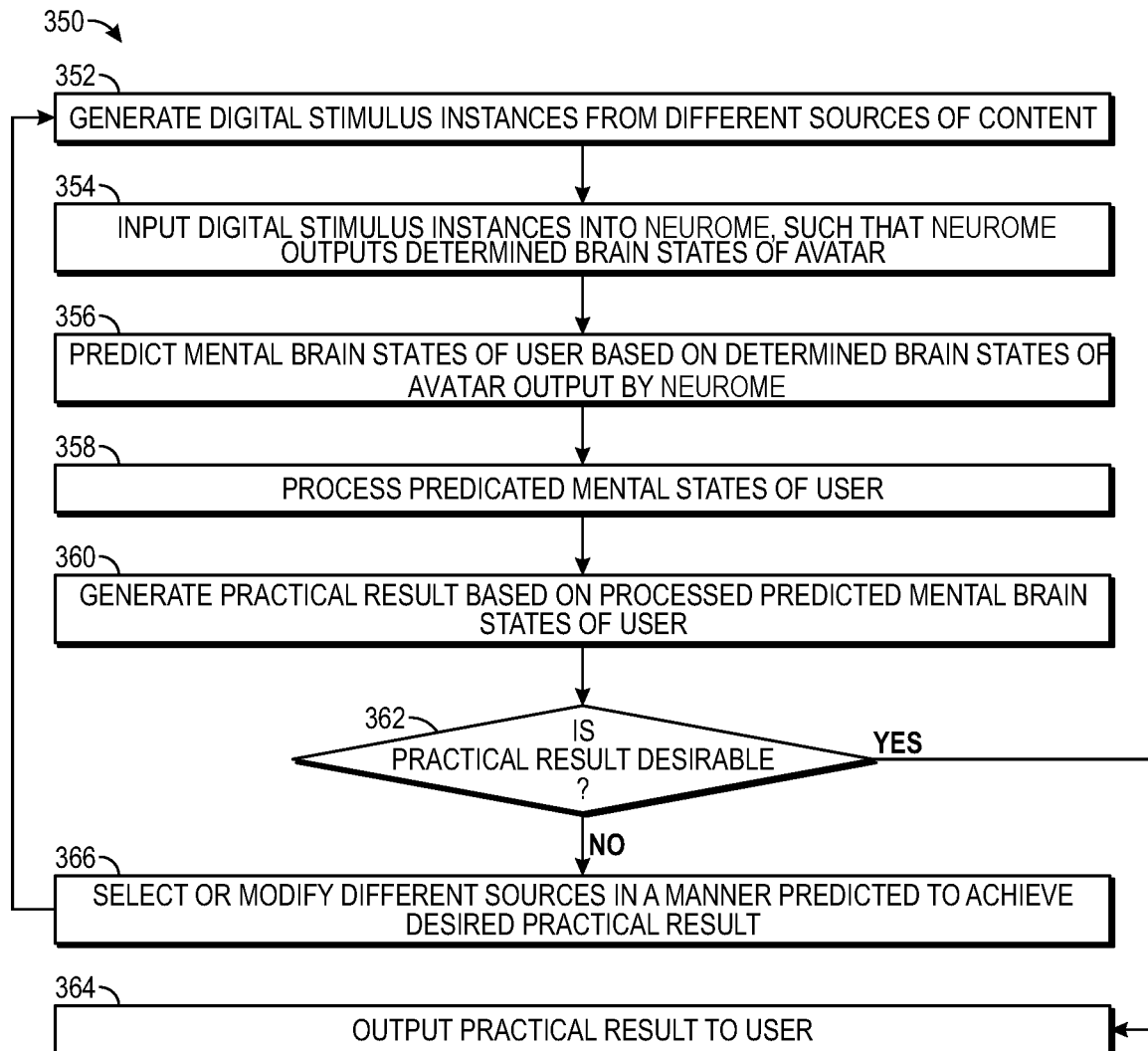
FIG. 22 is a flow diagram illustrating one method of operating the neurome emulation system of FIG. 11 to emulate the brain of a user.

Having described the structure and function of the brain emulation system 80, one exemplary method 350 of operating the brain emulation system 80 to emulate the brain 14 of the user 12 will now be described with reference to FIG. 22.

The method 350 comprises generating (via the stimulus conditioning pre-processor 82) a plurality of different stimulus instances 28*b* from a plurality of different sources of content 26 (step 352). Preferably, these different sources of content 26 are in the same genre as, but different from, the different sources of content 26 that the neurome 14' was trained on in the method 200 of FIG. 19. The method 350 further comprises inputting (via the brain state prediction processor 86) the digital stimulus instances 28*b* (raw data or meta data 54), such that the neurome 14' outputs a plurality of determined brain states 30' of the avatar 12' (step 354). The method 350 further comprises, based on the brain states 30' output by the neurome 14', predicting a plurality of mental brain states 30*b* of the user 12 (via the brain state prediction processor 86) as if analog instances 28*a* of the same stimuli 28 had been peripherally input into the brain 14 of the user 12 (step 356). If the brain states 30' of the avatar 12' output by the neurome 14' are physiological brain states 30*a'*, mental brain states 30*b'* may be derived from the physiological brain states 30*a'*, and output as the predicated brain states 30*b* of the user 12. If the brain states 30' of the avatar 12' output by the neurome 14' are mental brain states 30*b'*, the mental brain states 30*b'* can simply be output as the predicted mental brain states 30*b* of the user 12.

The method 350 further comprises (via the application post-processor 88) processing the determined brain states 30' of the avatar 12' (step 358), generating a practical result 90 (e.g., a down-selection of the different sources of content 26) based on the processed brain states 30' of the avatar 12' (step 360), and determining if the practical result 90 is desirable (step 362). If the practical result 90 is desirable, the method 300 comprises outputting (via the application post-processor 108) the practical result 90 to the user 12 (step 364). If the practical result 90 is not desirable, the method 300 comprises selecting or modifying (via sending control signals 92 from the application post-processor 88 to the stimulus conditioning pre-processor 82) the different sources of content 26 (step 366), and returning to step 352, such that the method 350 repeats for the newly selected or modified sources of content 26.

Figure 12A:
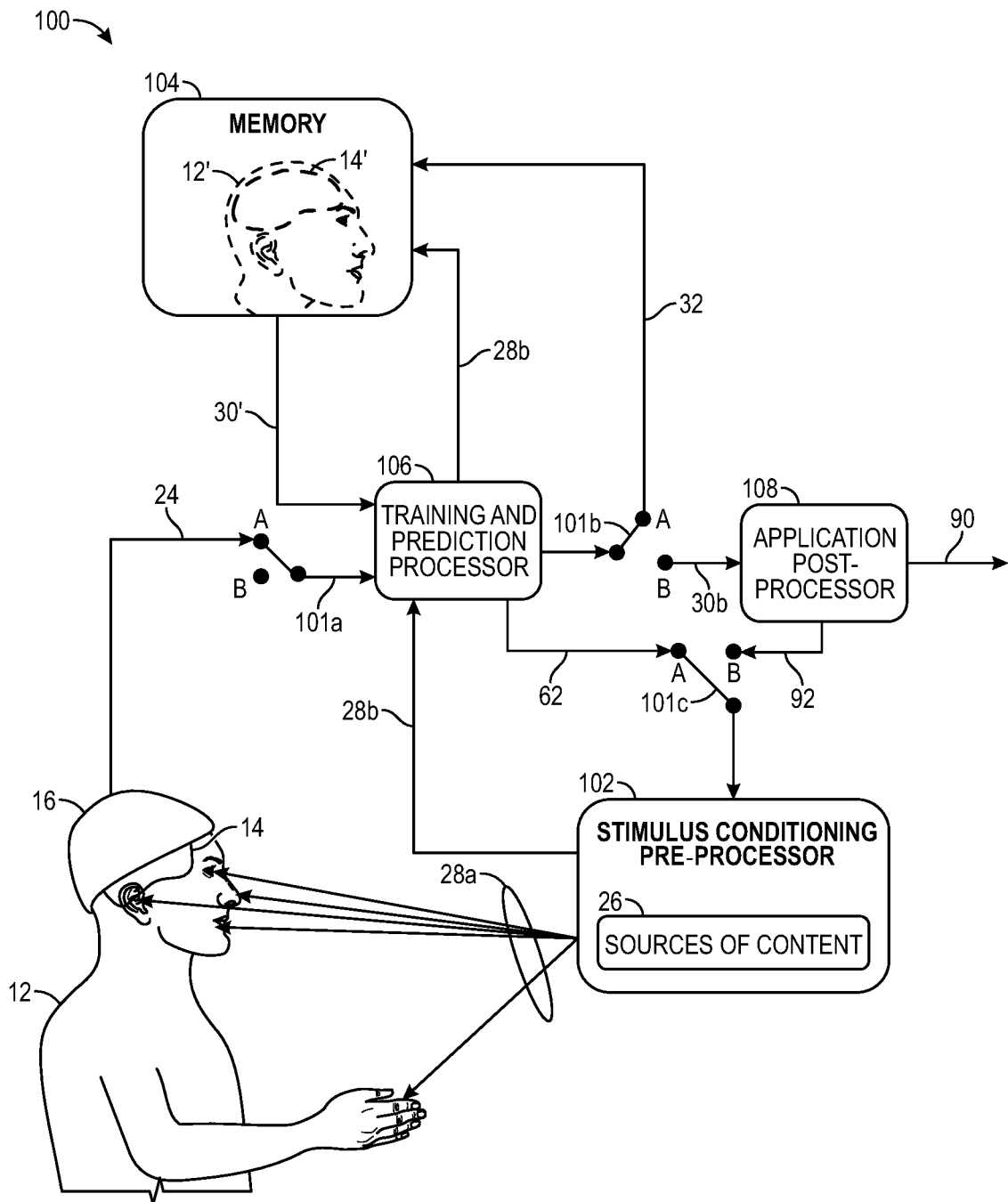
FIG. 12A is a block diagram of one embodiment of a neurome training/brain emulation system constructed in accordance with the present inventions, particularly showing the neurome training/brain emulation system in a neurome training mode.
Figure 12B:
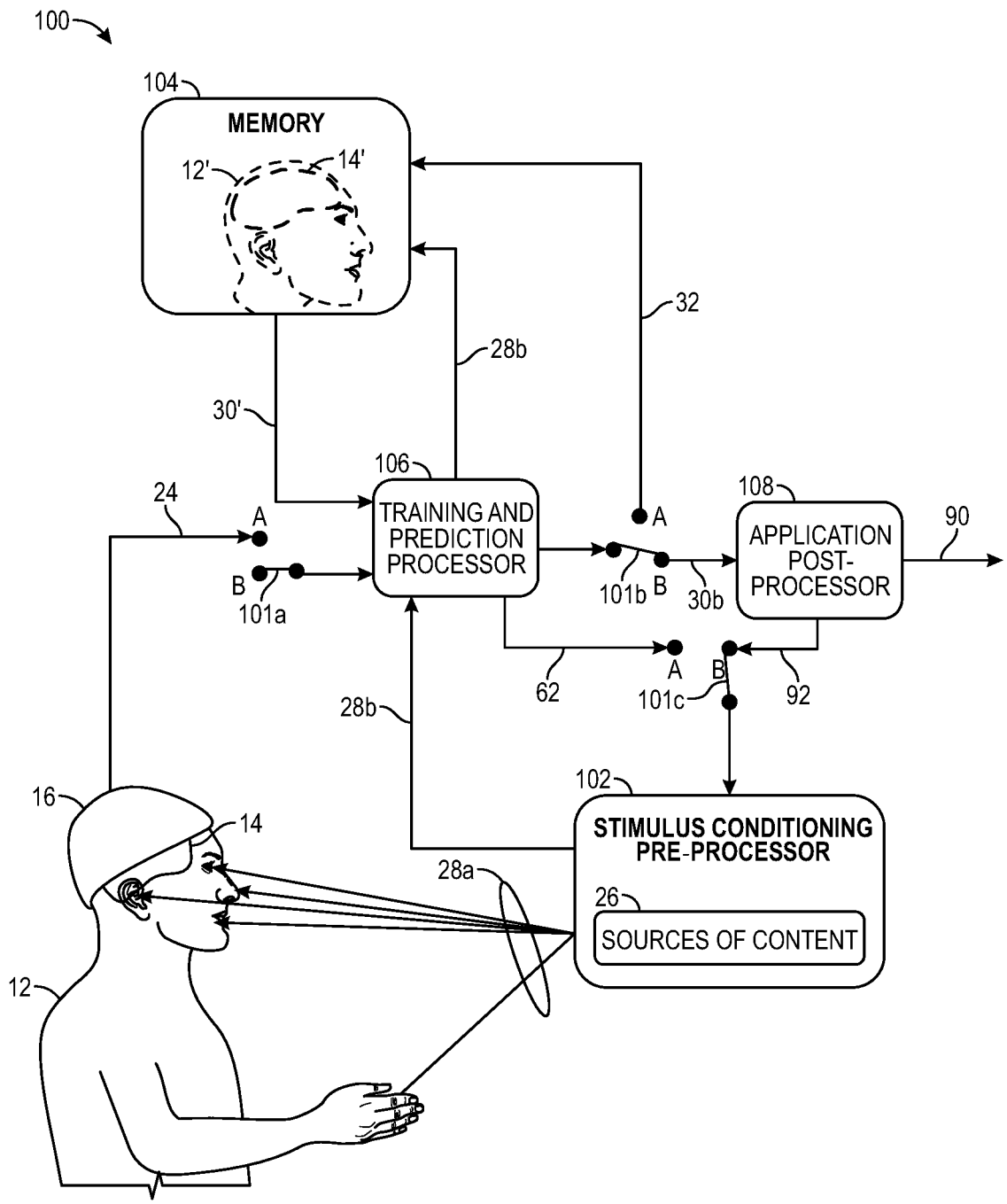
FIG. 12B is a block diagram of the neurome training/brain emulation system of FIG. 12A, particularly showing the neurome training/brain emulation system in a run-time mode.

Referring now to FIGS. 12A-12B, one embodiment of a neurome training/brain emulation system 100 is shown for both creating a neurome 14' of an avatar 12' and for using the neurome 14' to emulate the brain 14 of the user 12. The neurome training/brain emulation system 100 is capable of being switched between a neurome training mode (FIG. 12A) and a run-state mode (FIG. 12B) via operation of switches 101*a*-101*c*. The switches 101*a*-101*c* are configured for being collectively switched between the neurome training mode (switch position "A") and the run-state mode (switch position "B"). Any of the switches 101*a*-101*c* may be hardware switches or they may be virtual switches that merely illustrate flow or lack of flow of information between the components. The neurome training/brain emulation system 100 comprises the afore-described brain interface assembly 16 (shown in FIG. 1), as well as a stimulus conditioning pre-processor 102, memory 104, training and prediction processor 106, and an application post-processor 108.

When the switches 101*a*-101*c* are in positions "A" (FIG. 12A), such that the neurome training/brain emulation system 100 is in the neurome training mode, brain states 30 of the user 12 are determined, as described and shown in FIG. 1. In the neurome training mode, analog instances 28*a* of stimuli 28 are peripherally input into the brain 14 of the user 12 from sources of content 26, and digital instances 28*b* of the same stimuli 28 are input into the training and prediction processor 106 from the sources of content 26. In the illustrated embodiment, the functionality of the stimulus conditioning pre-processor 102 is similar to that of the stimulus conditioning pre-processor 20*c* illustrated in FIG. 10, and thus, may be configured for generating or acquiring the digital stimulus instances 28*b* and generating the analog stimulus instances 28*a* from the digital stimulus instances 28*b* under control of the training and prediction processor 106 via control signals 62. Alternatively, the stimulus conditioning pre-processor 102 may be similar to the stimulus conditioning pre-processors 20*a*-20*b* illustrated in FIG. 8 or FIG. 9.

In the neurome training mode, the training and prediction processor 106 trains the neurome 14' in the memory 104. In the illustrated embodiment, the functionality of the training and prediction processor 106 is similar to that of the neurome training processor 22 in FIGS. 1-4, and thus, may be configured for training the neurome 14' of the avatar 12 by generating and outputting control signals 32 to the neurome 14' that modifies the neurome 14', such that the brain states 30' output by the neurome 14' in response to the input of the digital stimulus instances 28*b* into the neurome 14' respectively match the brain states 30 of the user 12 determined by the training and prediction processor 106 (in the same manner as the brain state determination component 56 of the neurome training processor 22) in response to the analog stimulus instances 28*a* peripherally input into the brain 14 of the user 12.

Figure 19:
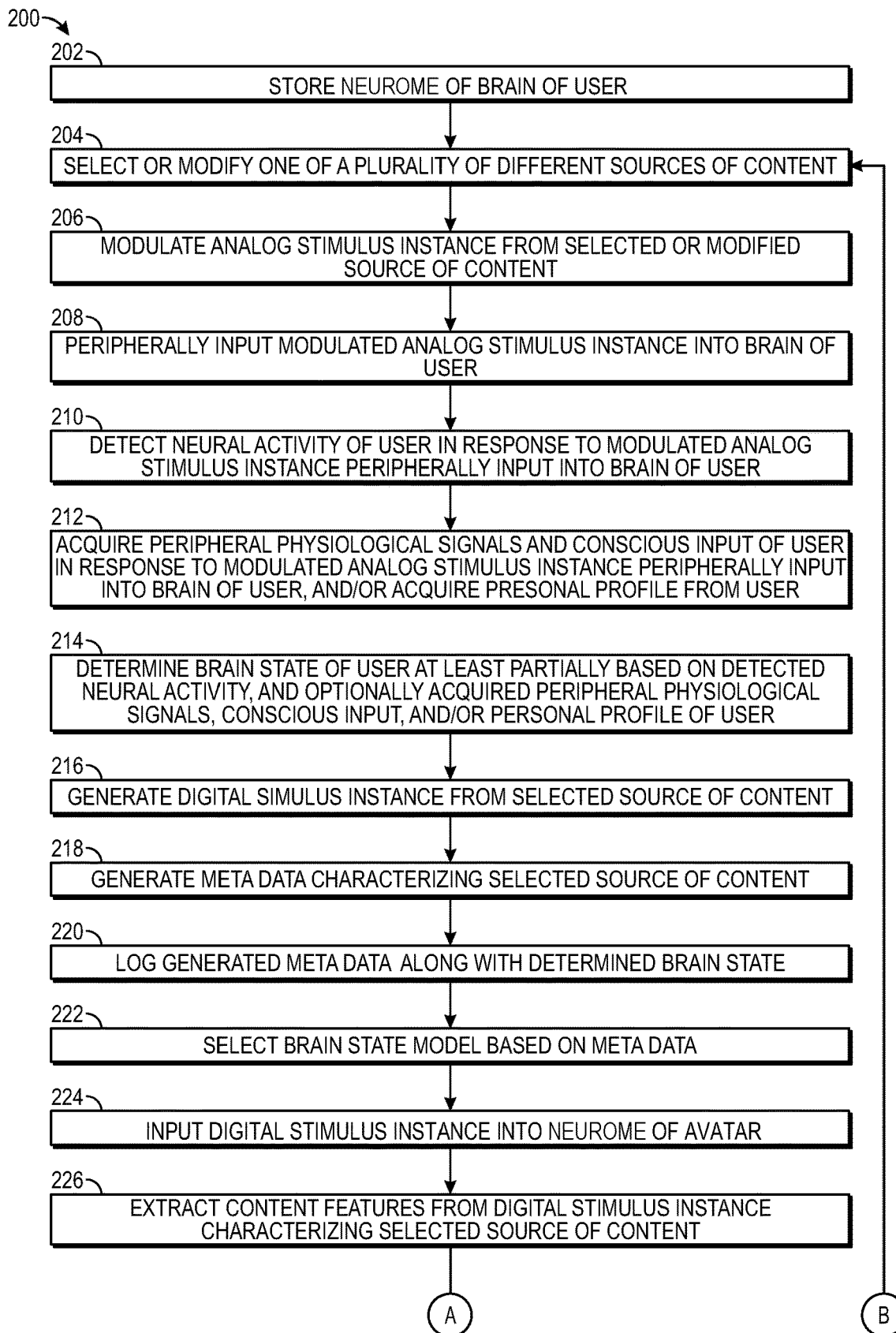
FIG. 19 is a flow diagram illustrating one method of operating the neurome training system of FIGS. 1-10 to train a neurome.
Figure 19:
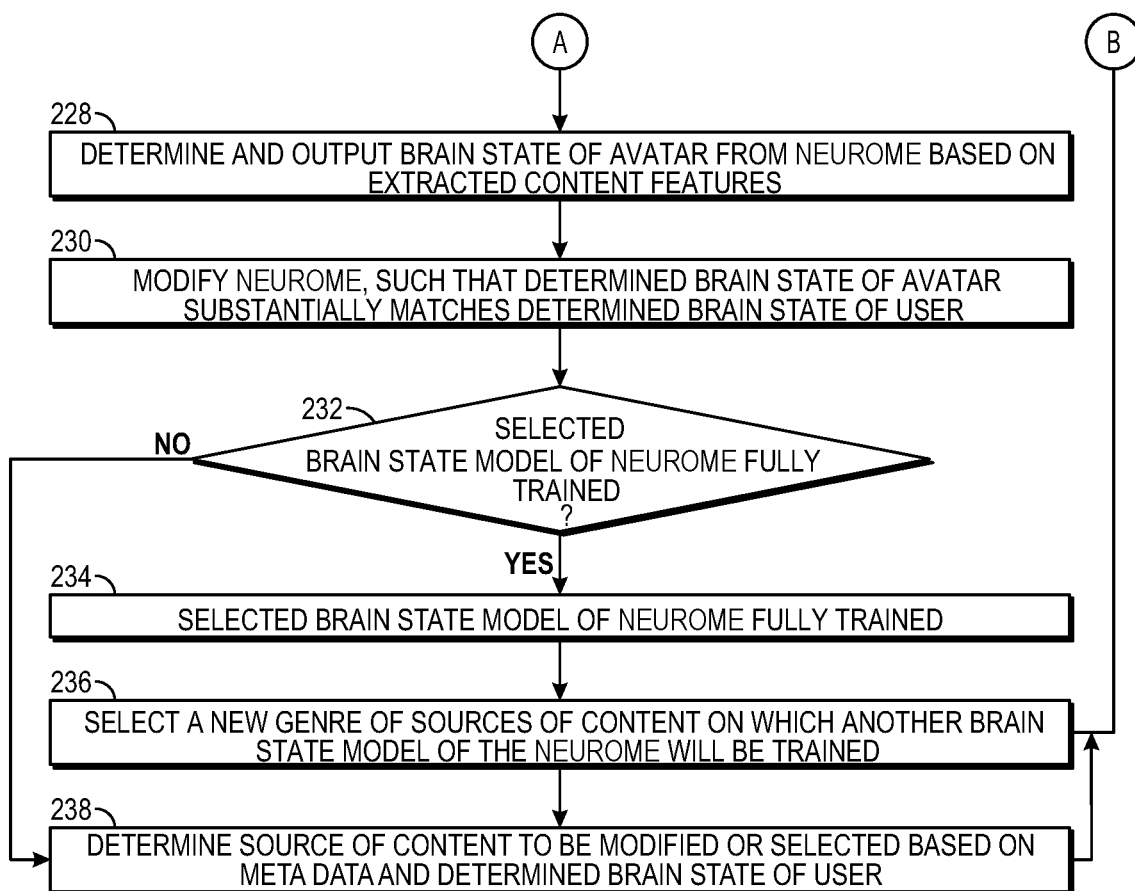

One method of operating the neurome training/brain emulation system 100 to train a neurome 14' of an avatar 12', when in the neurome training mode, may be performed in accordance with the method 200 illustrated in FIG. 19 and method 250 illustrated in FIG. 20.

When the switches 101*a*-101*c* are in positions "B" (FIG. 12B), such that the neurome training/brain emulation system 100 is in the run-state mode, brain states 30 of the user 12 are determined as described and shown in FIG. 11. In the run-state mode, digital instances 28*b* of stimuli 28 are input into the training and prediction processor 106 from the sources of content 26. In the illustrated embodiment, the functionality of the stimulus conditioning pre-processor 102 is similar to that of the stimulus conditioning pre-processor 82 illustrated in FIG. 11, and thus, may is configured for generating or acquiring the digital stimulus instances 28*b* under control of the application post-processor 108 via control signals 92 (similar to the application post-processor 108 in FIG. 11).

In the run-state mode, the functionality of the training and prediction processor 106 is similar to that of the brain state prediction processor 86 illustrated in FIG. 11, and thus, may be configured for inputting digital stimulus instances 28*b* output by the stimulus conditioning pre-processor 82 into the neurome 14', and, for each stimulus 28, predicting mental brain state 30*b* of the user 12 based on a brain state 30' of the avatar 12' output by the neurome 14'. The functionality of the application post-processor 108 is similar to the application post-processor 88 illustrated in FIG. 11, and thus, is configured for processing the predicted mental brain states 30*b* of the user 12 output by the training and prediction processor 106 and outputting a practical result 90 based on the predicted mental brain states 30*b*, and for controlling the stimulus conditioning pre-processor 102 via control signals 92, i.e., selects or modifies the digital stimulus instances 28*b* output by the stimulus conditioning pre-processor 102 to achieve a desired result.

One method of operating the neurome training/brain emulation system 10 to emulate the brain 14 of the user 12, when in the run-state mode, may be performed in accordance with the method 300 illustrated in FIG. 21.

Figure 13:
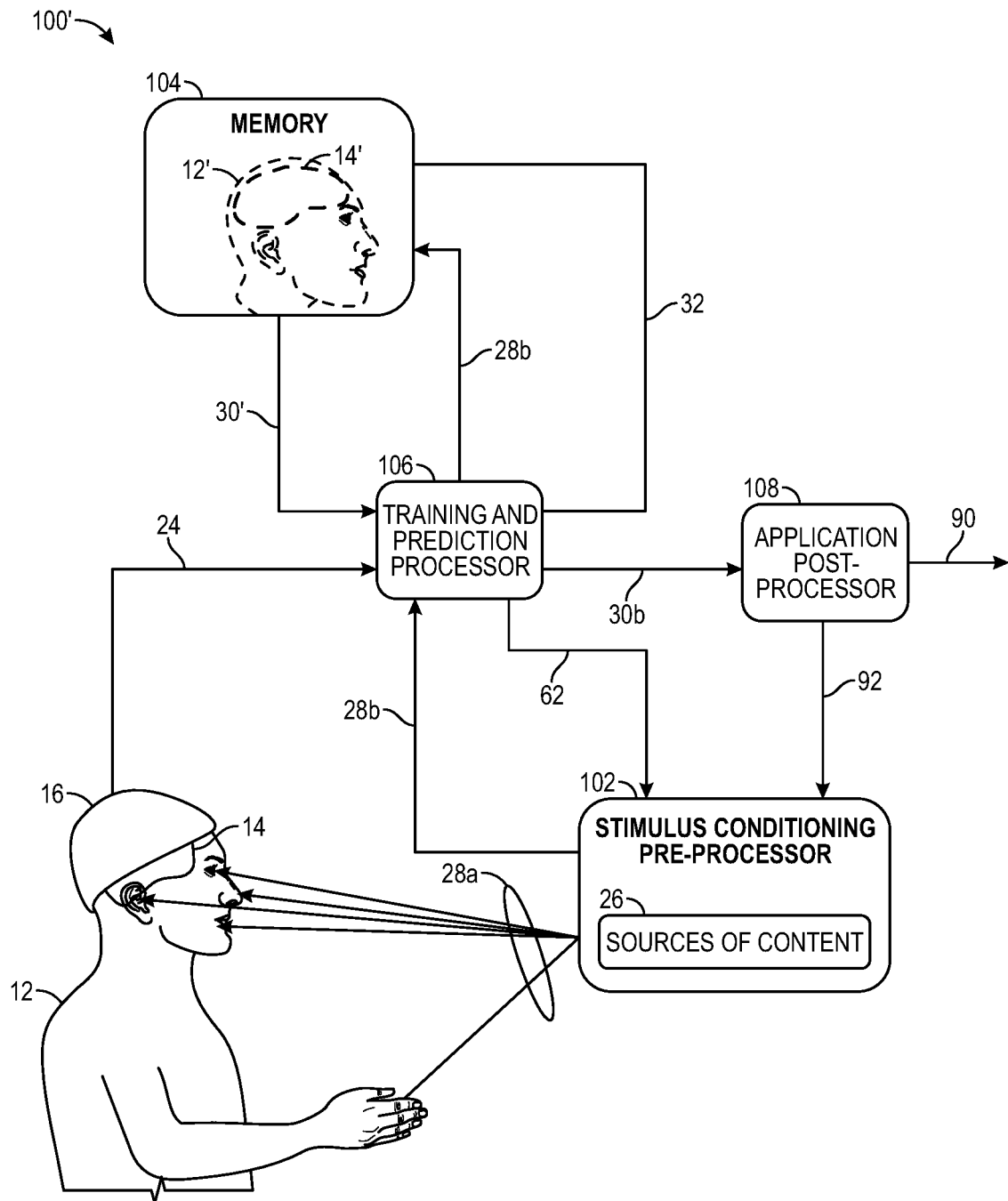
FIG. 13 is a block diagram of another embodiment of a neurome training/brain emulation system constructed in accordance with the present inventions.

Referring to FIG. 13, another embodiment of a neurome training/brain emulation system 100' is shown for both creating a neurome 14' of an avatar 12' and for using the neurome 14' to emulate the brain 14 of the user 12. The neurome training/brain emulation system 100' is similar to the neurome training/brain emulation system 100 described above with respect to FIGS. 12A-12B, with the exception that the neurome training/brain emulation system 100' is not switched between a neurome training mode and a run-state mode, but rather is configured for concurrently training the neurome 14' of the user and using the neurome 14' to emulate the brain 14 of the user.

Thus, in the same manner described above with respect to FIG. 12A, analog instances 28*a* of stimuli 28 are peripherally input into the brain 14 of the user 12 from sources of content 26, digital instances 28*b* of the same stimuli 28 are input into the training and prediction processor 106 from the sources of content 26, and the training and prediction processor 106 trains the neurome 14' of the avatar 12 by generating and outputting control signals 32 to the neurome 14', such that the brain states 30' output by the neurome 14' in response to the input of the digital stimulus instances 28*b* into the neurome 14' matches the brain states 30 of the user 12 determined by the training and prediction processor 106 in response to the analog stimulus instances 28*a* peripherally input into the brain 14 of the user 12.

Concurrently, the training and prediction processor 106 inputs digital stimulus instances 28*b* output by the stimulus conditioning pre-processor 102 into the neurome 14', and, for each stimulus 28, predicts the mental brain state 30*b* of the user 12 based on a brain state 30' of the avatar 12' output by the neurome 14'. The application post-processor 108 processes the predicted mental brain states 30*b* of the user 12 output by the training and prediction processor 106, outputs a practical result 90 based on the predicted mental brain states 30*b* of the user 12, and controls the stimulus conditioning pre-processor 102 via control signals 92, i.e., selects or modifies the digital stimulus instances 28*b* output by the stimulus conditioning pre-processor 102 to achieve a desired result.

Thus, it can be appreciated that the neurome training/brain emulation system 100' trains the neurome 14' while using the neurome 14' to emulate the brain 14 of the user 12.

It should be appreciated that although the stimulus conditioning pre-processor 102, training and prediction processor 106, and application post-processor 108 are illustrated as separate and distinct processors for purposes of clarity, it should be appreciated that the functionality (or any portions thereof) of the stimulus conditioning pre-processor 102, training and prediction processor 106, and application post-processor 108 may be merged into less processors or even a single processor. Furthermore, although each of the stimulus conditioning pre-processor 102, training and prediction processor 106, and application post-processor 108 are illustrated each as a single processor, the functionality of each of the stimulus conditioning pre-processor 102, training and prediction processor 106, and application post-processor 108 may be distributed amongst several processors. It should also be appreciated that those skilled in the art are familiar with the term "processor," and that it may be implemented in software, firmware, hardware, or any suitable combination thereof.

Figure 23:
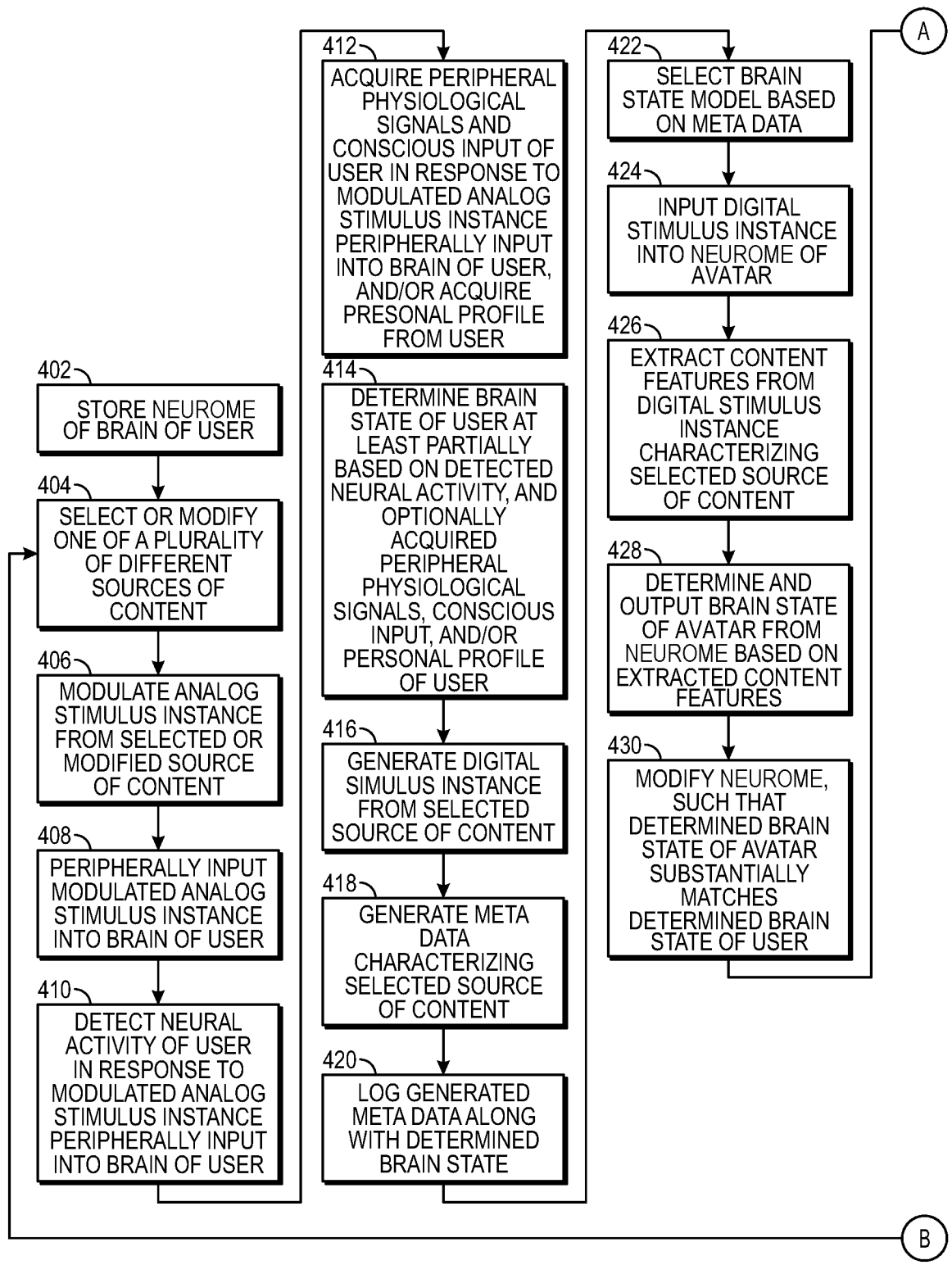
FIG. 23 is a flow diagram illustrating one method of operating the neurome training/brain emulation system of FIG. 13 to simultaneously training a neurome and use emulate the brain of a user.
Figure 23:
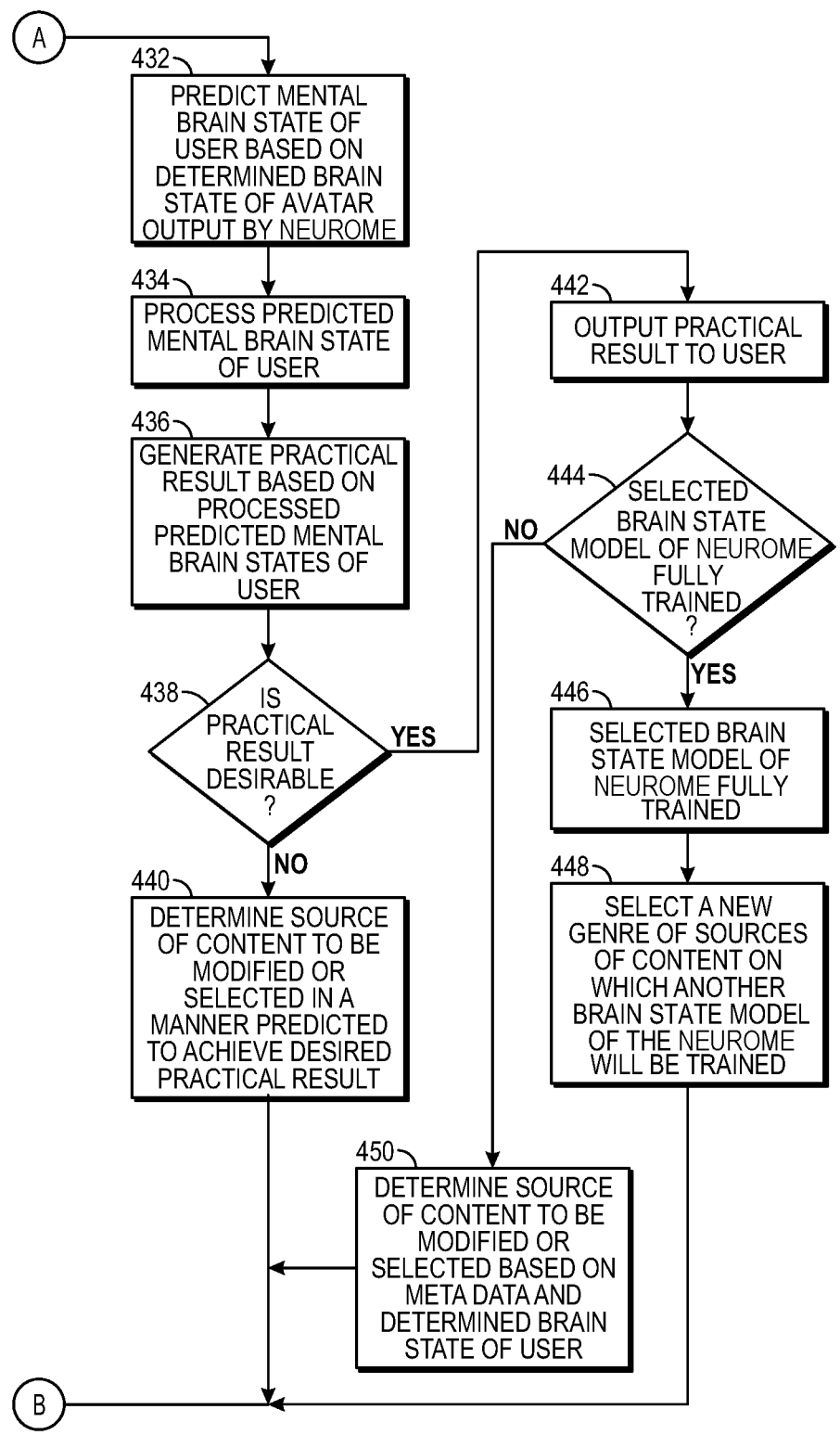

Having described the structure and function of the neurome training/brain emulation system 100', one exemplary method 400 of operating the neurome training/brain emulation system 100' to both train a neurome 14' and use the neurome 14' to emulate the brain 14 of the user 12 will now be described with reference to FIG. 23. The method 400 combines the method 200 illustrated in FIG. 19 and the method 350 illustrated in FIG. 22 to operate on the same stimulus 28 to both train the neurome 14' and emulate the brain 14 of the user 12.

In particular, in the same manner described above with respect to the method 200 illustrated in FIG. 19, the method 400 comprises storing (in the memory 104) a neurome 14' of an avatar 12' of the user 12 (step 402); selecting or modifying one of a plurality of different sources of content 26 (via the stimulus conditioning pre-processor 102 under control of the training and prediction processor 106 via control signals 62 or the application post-processor 108 via control signals 92) (step 404); optionally modulating (via the stimulus conditioning pre-processor 102) an analog stimulus instance 28*a* from the selected or modified source of content 26 (step 406); peripherally inputting the modulated (or unmodulated) analog stimulus instances 28a into the brain 14 of the user 12 (step 408); detecting neural activity 24 of the user 12 (via the brain interface assembly 16) in response to the modulated (or unmodulated) analog stimulus instances 28a peripherally input into the brain 14 of the user 12 (step 410); optionally comprises acquiring peripheral physiological signals 40 (via the sensors 38) and conscious input 44 from the user 12 (via the user interface 42) in response to the peripheral input of the analog stimulus instances 28a into the brain 14 of the user 12, and/or the personal profile 46 of the user 12 (step 412); determining a brain state 30 of the user 12 (via the training and prediction processor 106) at least partially based on the neural activity 24 detected in response to the analog stimulus instance 28a, and optionally based on the acquired peripheral physiological signals 40, conscious input 44 from the user 12, and/or the personal profile 46 (step 414), generating (via the stimulus conditioning pre-processor 102) a digital stimulus instance 28b from the selected or modified source of content 26 (step 416); generating meta data 54 characterizing the stimuli 28 (via the stimulus conditioning pre-preprocessor 104) (step 418), and in the case where the neurome 14' of the avatar 12 comprises multiple brain state models 50 and associated content feature extraction components 48, logging the meta data 54 along with the determined brain state 30 of the user 12 (via the training and prediction processor 106) (step 420), selecting one of the brain state models 50 based on the meta data 54 (via the training and prediction processor 106) (step 422); inputting (via the training and prediction processor 106) the digital stimulus instance 28b (raw data or meta data 54) into the neurome 14' (step 424); extracting content features 52 from the digital stimulus instance 28b characterizing the source of content 26 (via the content feature extraction component 48 of the neurome 14') (step 426)(if the digital stimulus instance 28b contains raw data); determining the brain state 30' of the avatar 12' (via the selected brain state model 50 of the neurome 14') based on the extracted content features 52 (step 428); modifying (via the training and prediction processor 106) the neurome 14', such that the determined brain state 30' of the avatar 12' output by the neurome 14' in response to the same digital stimulus instance 28b substantially matches the determined brain state 30 of the user 12 in response to the same analog stimulus instance 28a peripherally input into the brain 14 of the user 12 (step 430).

In the method 400, the same brain state 30' of the avatar 12' determined in response to the input of the digital stimulus instance 28b into the neurome 14', and used to train the neurome 14', is used to emulate the brain 14 of the user 12 in that it is predictive of the brain state 30 of the user 12 if the analog instance 28a of the stimulus 28 had been peripherally input into the brain 14 of the user 12. Thus, in the same manner described above with respect to the method 350 illustrated in FIG. 22, the method 400 further comprises, based on the brain state 30' output by the neurome 14', predicting a mental brain state 30b of the user 12 (via the training and prediction processor 106) as if the analog instances 28 of the same stimulus 28 had been peripherally input into the brain 14 of the user 12 (step 432); processing the determined brain states 30' of the avatar 12' (via the application post-processor 108) (step 434), generating a practical result 90 based on the processed predicted mental brain state 30b of the user 12 (step 436), and determining if the practical result 90 is desirable (step 438).

If the practical result 90 is not desirable (step 438), the method 400 comprises determining sources of content 26 to be selected or modified in a manner predicted to achieve the desired practical result (via the application post-processor 108) (step 440), and returning to step 404, where one of a plurality of different sources of content 26 is selected or modified (via the stimulus conditioning pre-processor 102 under control of the application post-processor 108 via control signals 92), such that the method 400 repeats for the selected or modified source of content 26. If the practical result 90 is desirable (step 438), the method 400 comprises outputting the practical result 90 to the user 12 (via the application post-processor 108) (step 442).

In the same manner described above with respect to the method 200 illustrated in FIG. 19, the method 400 comprises determining if the selected brain state model 50 of the neurome 14' has been fully trained (step 444). If the selected brain state model 50 of the neurome 14' has been fully trained, the selected brain state model 50 is deemed as such (step 446). The method 200 then comprises selecting a new genre of sources of content on which another brain state model 50 of the neurome 14' will be trained (step 448), and returning to step 404, where one of a plurality of different sources of content 26 is selected or modified (via the stimulus conditioning pre-processor 102 under control of the training and prediction processor 106 via control signals 62), such that the neurome 14' of the avatar 12 is trained on a source of content 26 in this selected genre of sources of content 26. If the selected brain state model 50 of the neurome 14' has not been fully trained (step 444), the method 400 further comprises determining the source of content 26 to be modified or selected based on the logged meta data 54 and determined brain states 30 of the user 12 (via the training and prediction processor 106) (step 450), and returning to step 404, where one of a plurality of different sources of content 26 is selected or modified (via the stimulus conditioning pre-processor 102 under control of the training and prediction processor 106 via control signals 62), such that the neurome 14' of the avatar 12 is trained on the next source of content 26.

Figure 14:
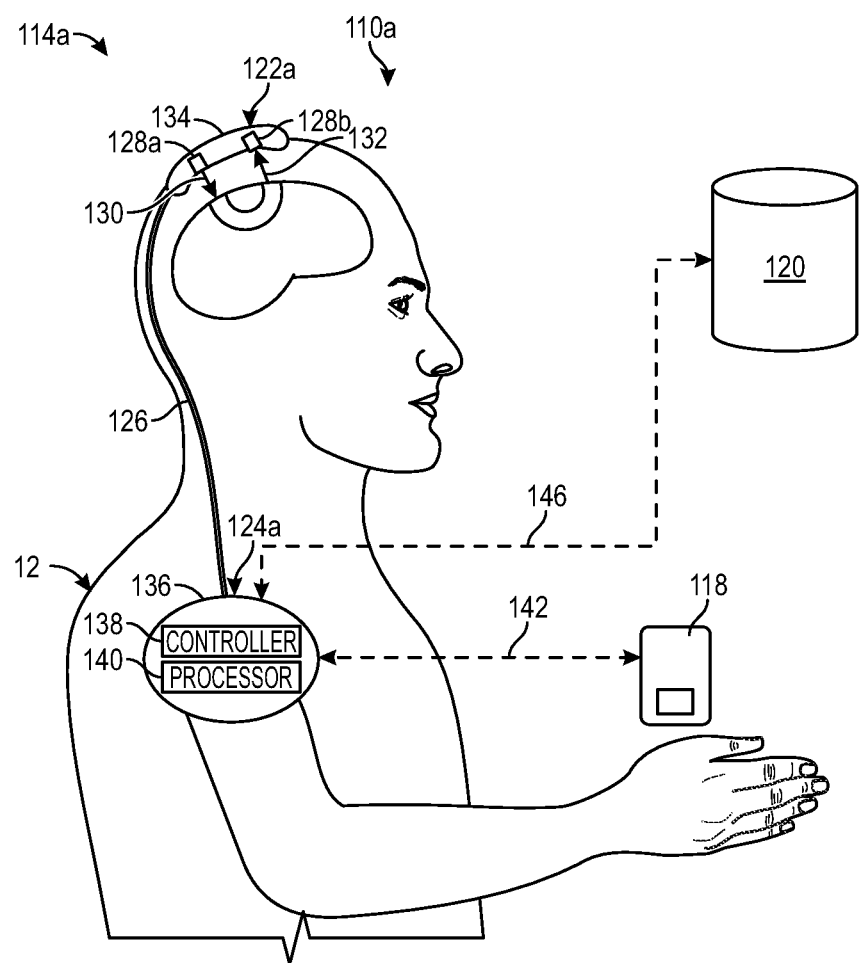
FIG. 14 is a view of one specific physical embodiment of the neurome training system of FIGS. 1-10, the neurome training/brain emulation system of FIG. 12A-12B, or the neurome training/brain emulation system of FIG. 13.

Referring to FIG. 14, a physical implementation of one embodiment of a system 110a that may embody the neurome training system 10 illustrated in FIGS. 1-10, the neurome training/brain emulation system 100 illustrated in FIGS. 12A-12B, or the neurome training/brain emulation system 100' illustrated in FIG. 13 will now be described.

The neurome training/brain emulation system 110a comprises an optically-based non-invasive brain interface assembly 114a configured for optically detecting neural activity in the brain 14 of the user 12.

The non-invasive brain interface assembly 114a may, e.g., incorporate any one or more of the neural activity detection technologies described in U.S. patent application Ser. No. 15/844,370, entitled "Pulsed Ultrasound Modulated Optical Tomography Using Lock-In Camera" (now U.S. Pat. No. 10,335,036), U.S. patent application Ser. No. 15/844,398, entitled "Pulsed Ultrasound Modulated Optical Tomography With Increased Optical/Ultrasound Pulse Ratio" (now U.S. Pat. No. 10,299,682), U.S. patent application Ser. No. 15/844,411, entitled "Optical Detection System For Determining Neural Activity in Brain Based on Water Concentration" (now U.S. Pat. No. 10,420,469), U.S. patent application Ser. No. 15/853,209, entitled "System and Method For Simultaneously Detecting Phase Modulated Optical Signals" (now U.S. Pat. No. 10,016,137), U.S. patent application Ser. No. 15/853,538, entitled "Systems and Methods For Quasi-Ballistic Photon Optical Coherence Tomography In Diffusive Scattering Media Using a Lock-In Camera" (now U.S. Pat. No. 10,219,700), U.S. patent application Ser.

No. 16/266,818, entitled "Ultrasound Modulating Optical Tomography Using Reduced Laser Pulse Duration," U.S. patent application Ser. No. 16/299,067, entitled "Non-Invasive Optical Detection Systems and Methods in Highly Scattering Medium," U.S. patent application Ser. No. 16/379,090, entitled "Non-Invasive Frequency Domain Optical Spectroscopy For Neural Decoding," U.S. patent application Ser. No. 16/382,461, entitled "Non-Invasive Optical Detection System and Method," U.S. patent application Ser. No. 16/392,963, entitled "Interferometric Frequency-Swept Source And Detector In A Photonic Integrated Circuit," U.S. patent application Ser. No. 16/392,973, entitled "Non-Invasive Measurement System and Method Using Single-Shot Spectral-Domain Interferometric Near-Infrared Spectroscopy Based On Orthogonal Dispersion, U.S. patent application Ser. No. 16/393,002, entitled "Non-Invasive Optical Detection System and Method Of Multiple-Scattered Light With Swept Source Illumination," U.S. patent application Ser. No. 16/385,265, entitled "Non-Invasive Optical Measurement System and Method for Neural Decoding," U.S. patent application Ser. No. 16/533,133, entitled "Time-Of-Flight Optical Measurement And Decoding Of Fast-Optical Signals," U.S. patent application Ser. No. 16/565,326, entitled "Detection Of Fast-Neural Signal Using Depth-Resolved Spectroscopy," U.S. patent application Ser. No. 16/226,625, entitled "Spatial and Temporal-Based Diffusive Correlation Spectroscopy Systems and Methods," U.S. Provisional Application Ser. No. 62/772,584, entitled "Diffuse Correlation Spectroscopy Measurement Systems and Methods," U.S. patent application Ser. No. 16/432,793, entitled "Non-Invasive Measurement Systems with Single-Photon Counting Camera," U.S. Provisional Application Ser. No. 62/855,360, entitled "Interferometric Parallel Detection Using Digital Rectification and Integration", U.S. Provisional Application Ser. No. 62/855,380, entitled "Interferometric Parallel Detection Using Analog Data Compression," U.S. Provisional Application Ser. No. 62/855,405, entitled "Partially Balanced Interferometric Parallel Detection," which are all expressly incorporated herein by reference.

The brain interface assembly 114a includes a wearable unit 122a configured for being applied to the user 12, and in this case, worn on the head of the user 12; and an auxiliary head-worn or non-head-worn unit 124a (e.g., worn on the neck, shoulders, chest, or arm). Alternatively, the functionality of the unit 124a may be incorporated into the head-worn unit 122a. The auxiliary non-head-worn unit 124a may be coupled to the head-worn unit 122a via a wired connection 126 (e.g., electrical wires). Alternatively, the brain interface assembly 114a may use a non-wired connection (e.g., wireless radio frequency (RF) signals (e.g., Bluetooth, Wifi, cellular, etc.) or optical links (e.g., fiber optic or infrared (IR)) for providing power to or communicating between the respective head-worn unit 122a and the auxiliary unit 124a.

The head-worn unit 122a comprises electronic or optical components, such as, e.g., one or more optical sources, an interferometer, one or more optical detector(s) (not shown), etc., an output port 128a for emitting sample light 130 generated by the brain interface assembly 114a into the head of the user 12, an input port 128b configured for receiving neural-encoded signal light 132 from the head of the user 12, which signal light is then detected, modulated and/or processed to determine brain activity of the user 12, and a support housing structure 134 containing the electronic or optical components, and ports 128a, 128b.

The support housing structure 134 may be shaped, e.g., have a banana, headband, cap, helmet, beanie, other hat shape, or other shape adjustable and conformable to the user's head, such that the ports 128a, 128b are in close contact with the outer skin of the head, and in this case, the scalp of the user 12. The support housing structure 134 may be made out of any suitable cloth, soft polymer, plastic, hard shell, and/or any other suitable material as may serve a particular implementation. In an alternative embodiment, optical fibers (not shown) may be respectively extended from the ports 128a, 128b, thereby freeing up the requirement that the ports 128a, 128b be disposed in close proximity to the surface of the head. In any event, an index matching fluid may be used to reduce reflection of the light generated by the head-worn unit 122a from the outer skin of the scalp. An adhesive, strap, or belt (not shown) can be used to secure the support housing structure 134 to the head of the user 12.

The auxiliary unit 124a comprises a housing 136 containing a controller 138 and a processor 140. The controller 138 is configured for controlling the operational functions of the head-worn unit 122a, whereas the processor 140 is configured for processing the neural-encoded signal light 132 acquired by the head-worn unit 122a to detect and localize the brain activity of the user 12. The auxiliary unit 124a may additionally include a power supply (which if head-worn, may take the form of a rechargeable or non-chargeable battery), a control panel with input/output functions, a display, and memory. Alternatively, power may be provided to the auxiliary unit 124a wirelessly (e.g., by induction).

The neurome training/brain emulation system 110a comprises a peripheral device 118 (e.g., a Smartphone, tablet computer, or the like) that contains the functionality of the memory 18, stimulus conditioning pre-processor 20, and neurome training processor 22 (if the system 110a embodies the neurome training system 10 illustrated in FIGS. 1-10), the functionality of the stimulus conditioning pre-processor 102, memory 104, training and prediction processor 106, and application post-processor 108 (if the system 110a embodies the neurome training/brain emulation system 100 of FIGS. 12A-12B) or the neurome training/brain emulation system 100' of FIG. 13), although in alternative embodiments, at least some of the processing functions of these components can be performed in other processing components, such as the processor 140 of the auxiliary unit 124a. The peripheral device 118 is coupled to the auxiliary unit 124a of the brain interface assembly 114a via a wireless connection 142 (e.g., wireless radio frequency (RF) signals (e.g., Bluetooth, Wifi, cellular, etc.) or optical links (e.g., fiber optic or infrared (IR)) for communicating between the peripheral device 118 and the brain interface assembly 114a. Alternatively, wired connections between the peripheral device 118 and the brain interface assembly 114a may be used.

The database, server, or cloud structure 120 may be coupled to the auxiliary unit 124a of the brain interface assembly 114a (and/or the peripheral device 118) via a wireless connection 146 (e.g., wireless radio frequency (RF) signals (e.g., Bluetooth, Wifi, cellular, etc.) or optical links (e.g., fiber optic or infrared (IR)) for communicating between the database, server, or cloud structure 120 and the brain interface assembly 114a and peripheral device 118. Alternatively, a wired connection between the database, server, or cloud structure 120 and the auxiliary unit 124a of the brain interface assembly 114a and/or the peripheral device 118 may be used. In the case where additional or supplemental computational power is required (e.g., the neurome training processor 22 of the neurome training system 10 shown in FIG. 1, or the training and prediction processor 106 of neurome training/brain emulation system 100 shown in FIGS. 12A and 12B, or neurome training/brain emulation system 100' shown in FIG. 13) to train the neurome 14'.

Figure 15:
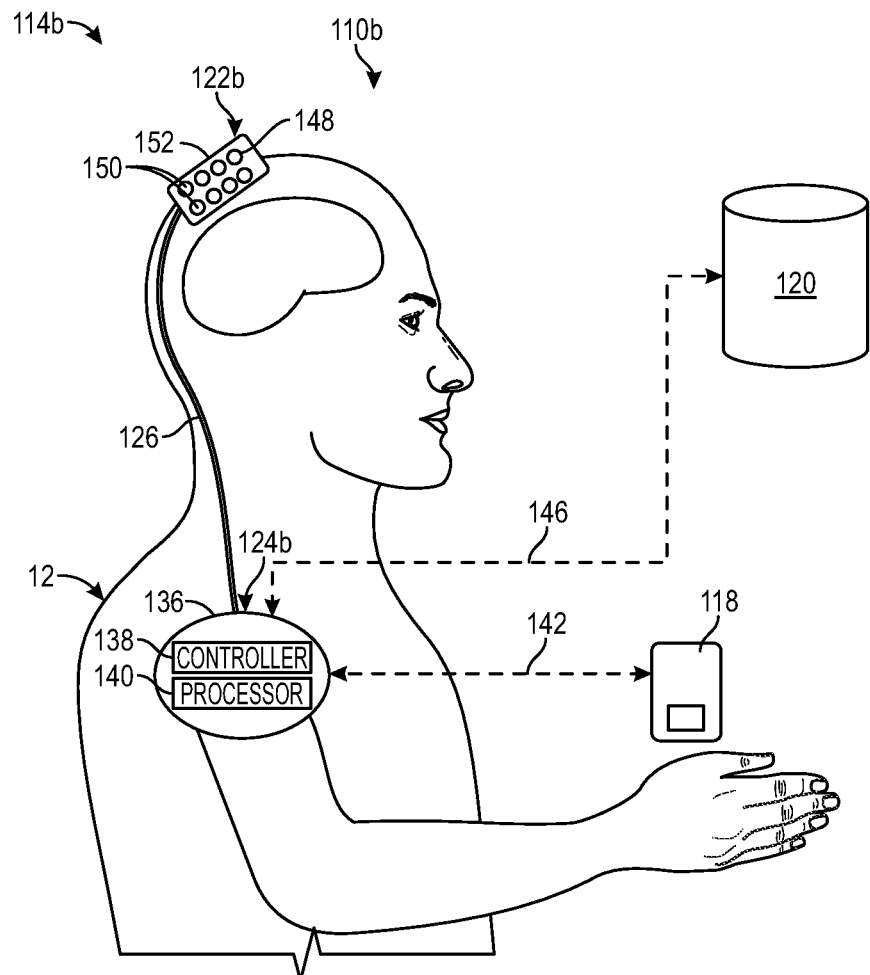
FIG. 15 is a view of another specific physical embodiment of the neurome training system of FIGS. 1-10, the neurome training/brain emulation system of FIG. 12A-12B, or the neurome training/brain emulation system of FIG. 13.

Referring to FIG. 15, a physical implementation of another embodiment of a system 100b that may embody the neurome training system 10 illustrated in FIGS. 1-10, the neurome training/brain emulation system 100 illustrated in FIGS. 12A-12B, or the neurome training/brain emulation system 100' illustrated in FIG. 13 will now be described.

The neurome training/brain emulation system 110b comprises an optically-based, time-domain, non-invasive brain interface assembly 114b configured for optically detecting neural activity in the brain 14 of the user 12. Example time domain-based optical measurement techniques include, but are not limited to, time-correlated single-photon counting (TCSPC), time domain near infrared spectroscopy (TD-NIRS), time domain diffusive correlation spectroscopy (TD-DCS), and time domain Digital Optical Tomography (TD-DOT). The non-invasive brain interface assembly 114b may, e.g., incorporate any one or more of the neural activity detection technologies described in U.S. Non-Provisional application Ser. No. 16/051,462, entitled "Fast-Gated Photodetector Architecture Comprising Dual Voltage Sources with a Switch Configuration" (now U.S. Pat. No. 10,158,038), U.S. patent application Ser. No. 16/202,771, entitled "Non-Invasive Wearable Brain Interface Systems Including a Headgear and a Plurality of Self-Contained Photodetector Units Configured to Removably Attach to the Headgear" (now U.S. Pat. No. 10,340,408), U.S. patent application Ser. No. 16/283,730, entitled "Stacked Photodetector Assemblies" (now U.S. Pat. No. 10,515,993), U.S. patent application Ser. No. 16/544,850, entitled "Wearable Systems with Stacked Photodetector Assemblies" (now U.S. Pat. No. 10,847,563), U.S. patent application Ser. No. 16/844,860, entitled "Photodetector Architectures for Time-Correlated Single Photon Counting," U.S. patent application Ser. No. 16/852,183, entitled "Photodetector Architectures for Efficient Fast-Gating," U.S. patent application Ser. No. 16/880,686, entitled "Photodetector Systems with Low-Power Time-To-Digital Converter Architectures" (now U.S. Pat. No. 10,868,207), U.S. Provisional Application Ser. No. 62/979,866 entitled "Optical Module Assemblies," U.S. Provisional Application Ser. No. 63/038,485 entitled "Control Circuit for a Light Source in an Optical Measurement System," U.S. Provisional Application Ser. No. 63/040,773 entitled "Multiplexing Techniques for Interference Reduction in Time-Correlated Signal Photon Counting," U.S. Provisional Application Ser. No. 63/064,249 entitled "Maintaining Consistent Photodetector Sensitivity in an Optical Measurement System," U.S. Provisional Application Ser. No. 63/027,018 entitled "Phase Lock Loop Circuit Based Adjustment of a Measurement Time Window in an Optical Measurement System," U.S. Provisional Application Ser. No. 63/044,521 entitled "Techniques for Determining a Timing Uncertainty of a Component of an Optical Measurement System," U.S. Provisional Application Ser. No. 63/059,382 entitled "Techniques for Characterizing a Nonlinearity of a Time-To-Digital Converter in an Optical Measurement System," U.S. Provisional Application Ser. No. 63/027,025 entitled "Temporal Resolution Control for Temporal Point Spread Function Generation in an Optical Measurement System," U.S. Provisional Application Ser. No. 63/057,080 entitled "Bias Voltage Generation in an Optical Measurement System," U.S. Provisional Application Ser. No. 63/051,099 entitled "Detection of Motion Artifacts in Signals Output by Detectors of a Wearable Optical Measurement System," U.S. Provisional Application Ser. No. 63/057,077 entitled "Dynamic Range Optimization in an Optical Measurement System," U.S. Provisional Application Ser. No. 63/074,721 entitled "Maintaining Consistent Photodetector Sensitivity in an Optical Measurement System," U.S. Provisional Application Ser. No. 63/070,123 entitled "Photodetector Calibration of an Optical Measurement System," U.S. Provisional Application Ser. No. 63/071,473 entitled "Estimation of Source-Detector Separation in an Optical Measurement System," U.S. Provisional Application Ser. No. 63/081,754 entitled "Wearable Module Assemblies for an Optical Measurement System," U.S. Provisional Application Ser. No. 63/086,350 entitled "Wearable Devices and Wearable Assemblies with Adjustable Positioning for Use in an Optical Measurement System," U.S. Provisional Application Ser. No. 63/038,459 entitled "Integrated Detector Assemblies for a Wearable Module of an Optical Measurement System," U.S. Provisional Application Ser. No. 63/038,468 entitled "Detector Assemblies for a Wearable Module of an Optical Measurement System and Including Spring-Loaded Light-Receiving Members," U.S. Provisional Application Ser. No. 63/038,481 entitled "Integrated Light Source Assembly with Laser Coupling for a Wearable Optical Measurement System," U.S. Provisional Application Ser. No. 63/079,194 entitled "Multimodal Wearable Measurement Systems and Methods," U.S. Provisional Application Ser. No. 63/064,688 entitled "Time Domain-Based Optical Measurement System and Method Configured to Measure Absolute Properties of Tissue," U.S. Provisional Application Ser. No. 63/138,159 entitled "Systems and Methods for Noise Removal in an Optical Measurement System," and U.S. Provisional Application Ser. No. 63/030,199 entitled "Time Resolved Histogram Data Compression and Dimensionality Reduction for Data Transfer, Optical Parameter Recovery, and Image Reconstruction," which are all expressly incorporated herein by reference in their entirety.

The brain interface assembly 114b includes a head-worn unit 122b that is configured for being applied to the user 12, and in this case, worn on the head of the user 12; and an auxiliary non-head-worn unit 124b (e.g., worn on the neck, shoulders, chest, or arm). Alternatively, the functionality of the unit 124b may be incorporated into the head-worn unit 122b, as described below. The auxiliary non-head-worn unit 124b may be coupled to the head-worn unit 122b via a wired connection 126 (e.g., electrical wires). Alternatively, the brain interface assembly 114b may use a non-wired connection (e.g., wireless radio frequency (RF) signals (e.g., Bluetooth, Wifi, cellular, etc.) or optical links (e.g., fiber optic or infrared (IR)) for providing power to or communicating between the respective head-worn unit 122b and the auxiliary unit 124b.

The head-worn unit 122b includes one or more light sources 148 configured for generating light pulses. The light source(s) 148 may be configured for generating one or more light pulses at one or more wavelengths that may be applied to a desired target (e.g., a target within the brain). The light source(s) 148 may be implemented by any suitable combination of components. For example, light source(s) 148 described herein may be implemented by any suitable device. For example, a light source as used herein may be, for example, a distributed feedback (DFB) laser, a super luminescent diode (SLD), a light emitting diode (LED), a diode-pumped solid-state (DPSS) laser, a laser diode (LD), a super luminescent light emitting diode (sLED), a vertical-cavity surface-emitting laser (VCSEL), a titanium sapphire laser, a micro light emitting diode (m LED), and/or any other suitable laser or light source.

The head-worn unit 122b includes a plurality of photodetector units 150, e.g., comprising single-photon avalanche diodes (SPADs) configured for detecting a single photon (i.e., a single particle of optical energy) in each of the light pulses. For example, an array of these sensitive photodetector units can record photons that reflect off of tissue within the brain in response to application of one or more of the light pulses generated by the light sources 148. Based on the time it takes for the photons to be detected by the photodetector units, neural activity and other attributes of the brain can be determined or inferred.

Photodetector units that employ the properties of a SPAD are capable of capturing individual photons with very high time-of-arrival resolution (a few tens of picoseconds). When photons are absorbed by a SPAD, their energy frees bound charge carriers (electrons and holes) that then become free-carrier pairs. In the presence of an electric field created by a reverse bias voltage applied to the diode, these free-carriers are accelerated through a region of the SPAD, referred to as the multiplication region. As the free carriers travel through the multiplication region, they collide with other carriers bound in the atomic lattice of the semiconductor, thereby generating more free carriers through a process called impact ionization. These new free-carriers also become accelerated by the applied electric field and generate yet more free-carriers. This avalanche event can be detected and used to determine an arrival time of the photon. In order to enable detection of a single photon, a SPAD is biased with a reverse bias voltage having a magnitude greater than the magnitude of its breakdown voltage, which is the bias level above which free-carrier generation can become self-sustaining and result in a runaway avalanche. This biasing of the SPAD is referred to as arming the device. When the SPAD is armed, a single free carrier pair created by the absorption of a single photon can create a runaway avalanche resulting in an easily detectable macroscopic current.

It will be recognized that in some alternative embodiments, the head-worn unit 122b may include a single light source 148 and/or single photodetector unit 150. For example, brain interface system 114b may be used for controlling a single optical path and for transforming photodetector pixel measurements into an intensity value that represents an optical property of a brain tissue region. In some alternative embodiments, the head-worn unit 122b does not include individual light sources. Instead, a light source configured to generate the light that is detected by the photodetector may be included elsewhere in the brain interface system 114b. For example, a light source may be included in the auxiliary unit 124b. In alternative embodiments, a module assembly may house the photodetector units 150 and the light source 148 in the same assembly and eliminate the need for long fiber optic cables. For example, head-worn unit 122b may include the wearable modular assembly wherein the wearable modular assembly includes a plurality of connectable wearable modules. Each wearable module includes a light source 148 configured to emit a light pulse toward a target within the brain of the user and a plurality of photodetector units 150 configured to receive photons included in the light pulse after the photons are scattered by the target. The wearable module assemblies can conform to a 3D surface of the user's head, maintain tight contact of the detectors with the user's head to prevent detection of ambient light, and maintain uniform and fixed spacing between light sources 148 and photodetector units 150. The wearable module assemblies may also accommodate a large variety of head sizes, from a young child's head size to an adult head size, and may accommodate a variety of head shapes and underlying cortical morphologies through the conformability and scalability of the wearable module assemblies. These exemplary modular assemblies and systems are described in more detail in U.S. Provisional Application Ser. Nos. 63/038,459; 63/038,468; 63/038,481; 63/064,688; 63/081,754; and 63/086,350, previously incorporated herein by reference.

The head-worn unit 122b further comprises a support housing structure 152 containing the light source(s) 148, photodetector units 150, and other electronic or optical components. In alternative embodiments, the housing structure 152 may include a single module assembly containing a single light source 148, plurality of photodetector units 150, and other electronic or optical components. In other alternative embodiments, the housing structure 152 may include a plurality of module assemblies tiled together, wherein each module assembly includes the light source 148, plurality of photodetector units 150, and other electronic or optical components. As will be described in further detail below, the support housing structure 152 may be shaped, e.g., have a banana, headband, cap, helmet, beanie, other hat shape, or other shape adjustable and conformable to the user's head, such that the photodetector units 150 are in close contact with the outer skin of the head, and in this case, the scalp of the user 12. The support housing structure 152 may be made out of any suitable cloth, soft polymer, plastic, hard shell, and/or any other suitable material as may serve a particular implementation.

While brain interface system 114b shows one head-word unit 122b, any suitable number of head-worn units 122b may be used, for instance at different locations on the head.

The auxiliary unit 124b comprises the housing 136 containing the controller 138 and the processor 140. The controller 138 is configured for controlling the operational functions of the head-worn unit 122b, whereas the processor 140 is configured for processing the photons acquired by the head-worn unit 122b to detect and localize the detected neural activity 24 of the user 12, as well as to determine the mental state of the user 12 based on the detected neural activity 24 of the user 12 if not performed by other processing units in the neurome training/brain emulation system 10b. The auxiliary unit 124b may additionally include a power supply (which if head-worn, may take the form of a rechargeable or non-chargeable battery), a control panel with input/output functions, a display, and memory. Alternatively, power may be provided to the auxiliary unit 124b wirelessly (e.g., by induction).

The neurome training/brain emulation system 110b further comprises the peripheral device 118 and the database, server, or cloud structure 120, which can function and be coupled to each other in the same manner described above with respect to the neurome training/brain emulation system 110a.

Referring now to FIGS. 16A-16D, different embodiments of the brain interface assembly 114b will be described. Such brain interface assemblies 114b may communicate wirelessly or via wire with the peripheral device 118 and database, server, cloud structure 120, as described above. Each of the brain interface assemblies 114b described below comprises a head-worn unit 122b having a plurality of photodetector units 150 and a support housing structure 152 in which the photodetector units 150 are embedded within individual slots or cut-outs. Each of the photodetector units 150 may comprise, e.g., a SPAD, voltage sources, capacitors, switches, and any other circuit components and other optical components (not shown) required to detect photons. Each of the brain interface assemblies 114b may also comprise one or more light sources (not shown) for generating light pulses, although the source of such light may be derived from ambient light in some cases. In alternative embodiments, the light source may be a component contained within of the photodetector units. Each of brain interface assemblies 114b may also comprise a control/processing unit 154, such as, e.g., a control circuit, time-to-digital (TDC) converter, and signal processing circuit for controlling the operational functions of the photodetector units 150 and any light source(s), and processing the photons acquired by photodetector units 150 to detect and localize the brain activity of the user 12. As will be described in further detail below, the control/processing unit 154 may be contained in the head-worn unit 122b or may be incorporated into a self-contained auxiliary unit. As will be set forth below, the support housing structure 152 may be shaped, e.g., have a banana, headband, cap, helmet, beanie, other hat shape, or other shape adjustable and conformable to the user's head, such that the photodetector units 150 are in close contact with the outer skin of the head, and in this case, the scalp of the user 12.

Figure 16A:
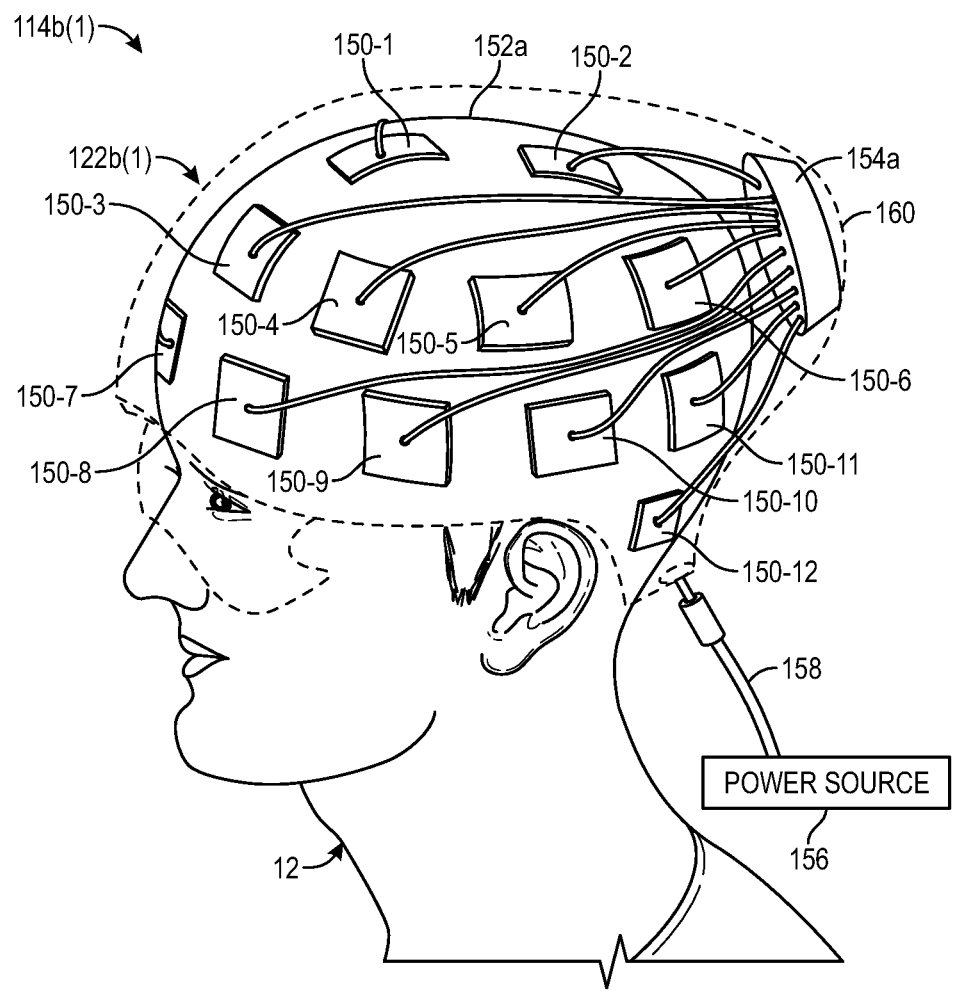
FIGS. 16A-16D are views of exemplary non-invasive wearable devices as used with the system of FIG. 15.

As shown in FIG. 16A, a brain interface assembly 114b(1) comprises a head-worn unit 122b(1) and a power source 156 coupled to the head-worn unit 122b(1) via a power cord 158. The head-worn unit 122b(1) includes the photodetector units 150 (shown as 150-1 through 150-12) and a control/processing unit 154a. The head-worn unit 122b(1) further includes a support housing structure 152a that takes a form of a cap that contains the photodetector units 150 and control/processing unit 154a. The material for the cap 152a may be selected out of any suitable cloth, soft polymer, plastic, hard shell, and/or any other suitable material as may serve a particular implementation. The power source 156 may be implemented by a battery and/or any other type of power source configured to provide operating power to the photodetector units 150, control/processing unit 154a, and any other component included within the brain interface assembly 122b(1) via the power cord 158. The head-worn unit 122b(1) optionally includes a crest or other protrusion 160 formed in the cap 152a for providing means of carrying/housing a control/processing unit 154a.

Figure 16B:
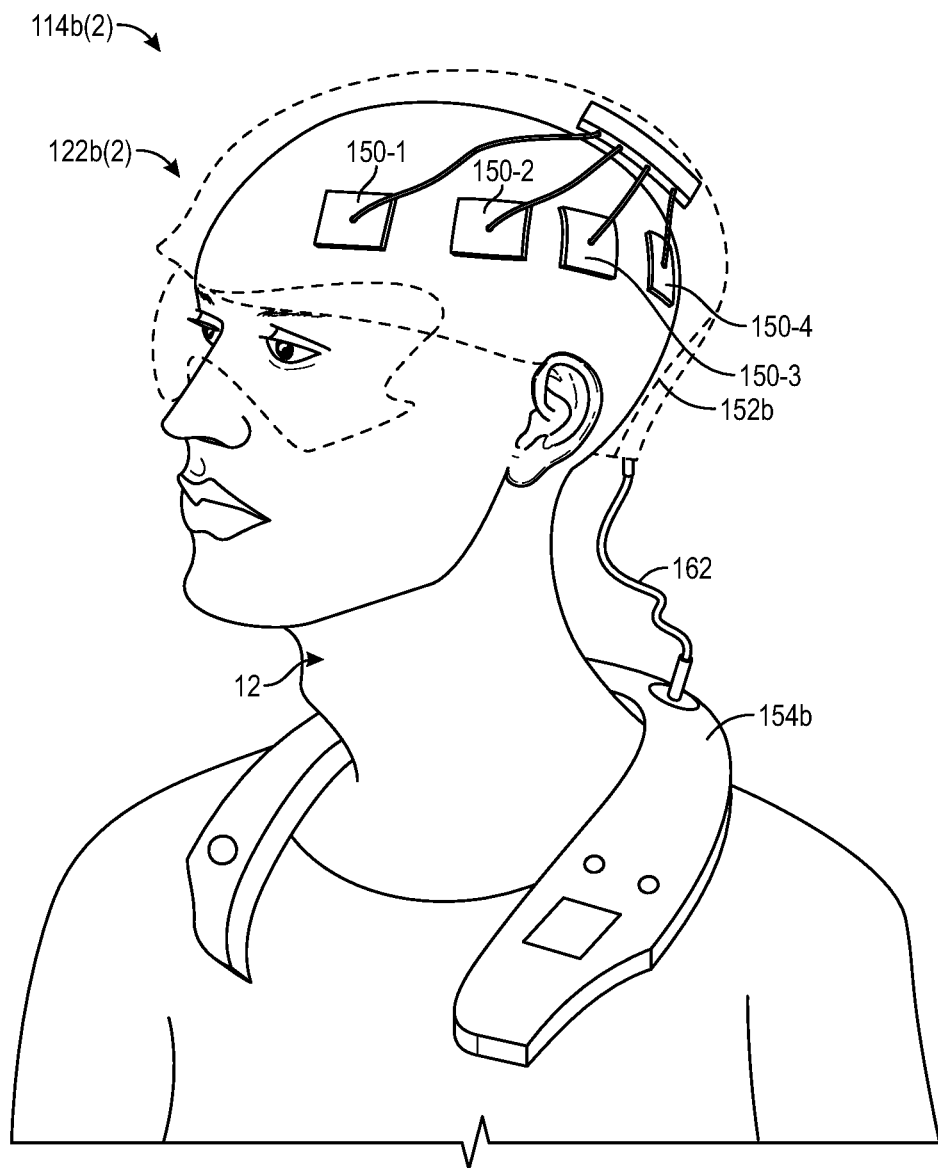

As shown in FIG. 16B, a brain interface assembly 114b(2) comprises a head-worn unit 122b(2) and a control/processing unit 154b coupled to the head-worn unit 122b(2) via a wired connection 162. The head-worn unit 122b(2) includes the photodetector units 150 (shown as 150-1 through 150-4), and a support housing structure 152b that takes a form of a helmet containing the photodetector units 150. The material for the helmet 152b may be selected out of any suitable polymer, plastic, hard shell, and/or any other suitable material as may serve a particular implementation. Unlike the control/processing unit 154a of the brain interface assembly 114b(1) illustrated in FIG. 16A, which is contained in the head-worn unit 122b(1), the control/processing unit 154b is self-contained, and may take the form of a garment (e.g., a vest, partial vest, or harness) for being worn on the shoulders of the user 12. The self-contained control/processing unit 154b may additionally include a power supply (which if head-worn, may take the form of a rechargeable or non-chargeable battery), a control panel with input/output functions, a display, and memory. Alternatively, power may be provided to the self-contained control/processing unit 154b wirelessly (e.g., by induction).

Figure 16C:
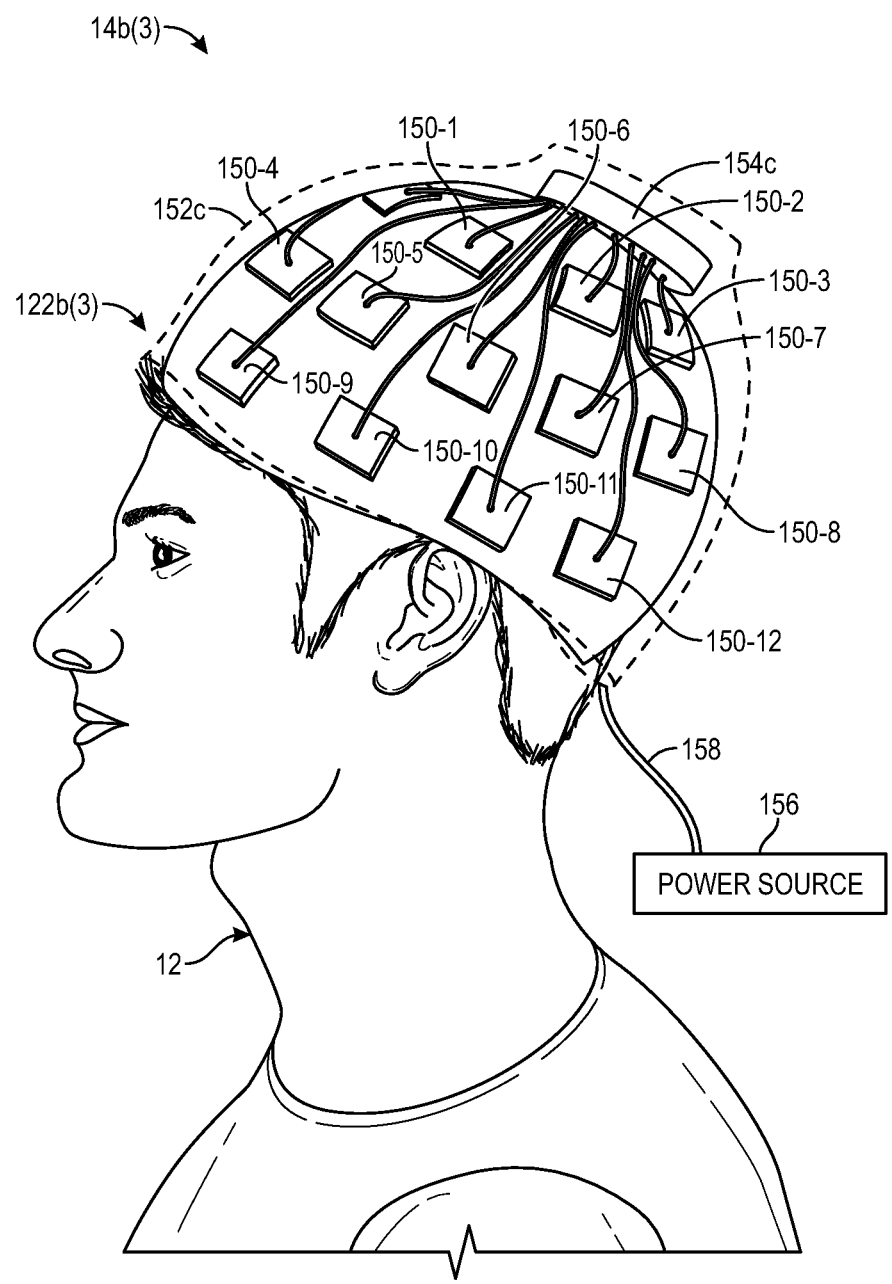

As shown in FIG. 16C, a brain interface assembly 114b(3) comprises a head-worn unit 122b(3) and a power source 156 coupled to the head-worn unit 122b(3) via a power cord 174. The head-worn unit 122b(3) includes the photodetector units 150 (shown as 150-1 through 150-12) and a control/processing unit 154c. The head-worn unit 122b(3) further includes a support housing structure 152c that takes a form of a beanie that contains the photodetector units 150 and control/processing unit 154c. The material for the beanie 152c may be selected out of any suitable cloth, soft polymer, plastic, and/or any other suitable material as may serve a particular implementation. The power source 156 may be implemented by a battery and/or any other type of power source configured to provide operating power to the photodetector units 150, control/processing unit 154c, and any other component included within the brain interface assembly 122b(3) via a wired connection 158.

Figure 16D:
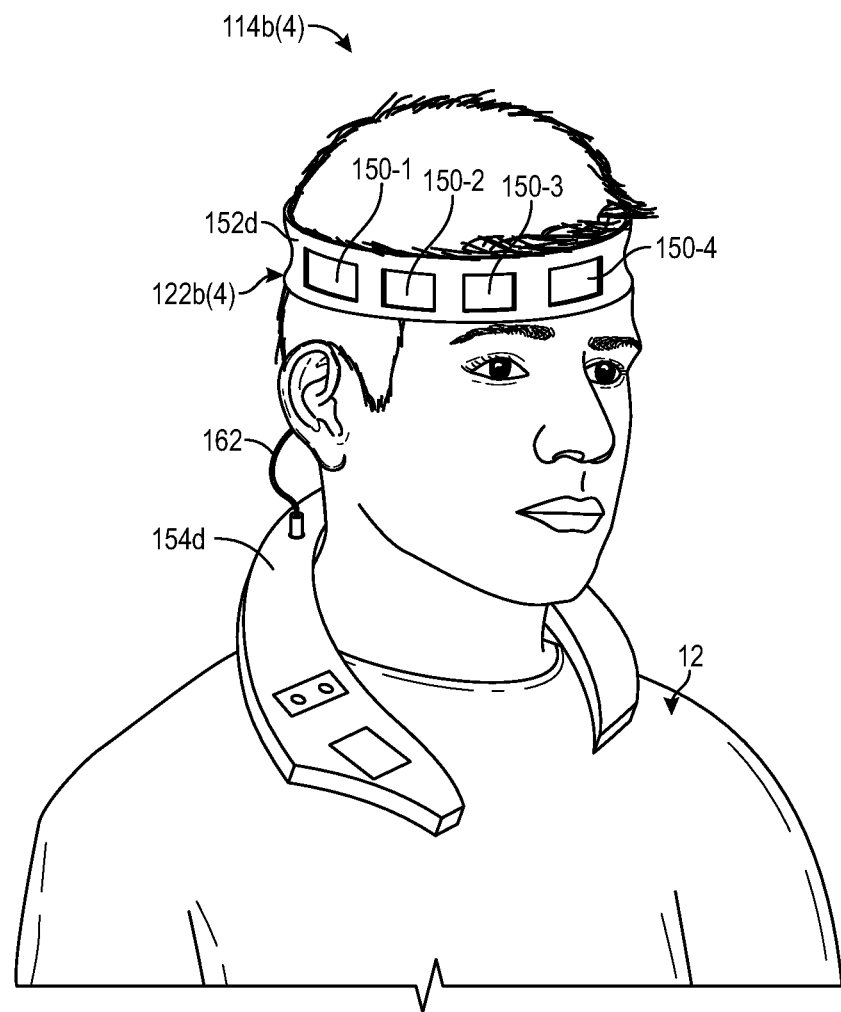

As shown in FIG. 16D, a brain interface assembly 114b(4) comprises a head-worn unit 122b(4) and a control/processing unit 154d coupled to the head-worn unit 122b(4) via a wired connection 162. The head-worn unit 122b(4) includes the photodetector units 150 (shown as 150-1 through 150-4), and a support housing structure 152d that takes a form of a headband containing the photodetector units 150. The material for the headband 152d may be selected out of any suitable cloth, soft polymer, plastic, hard shell, and/or any other suitable material as may serve a particular implementation. The control/processing unit 154d is self-contained, and may take the form of a garment (e.g., a vest, partial vest, or harness) for being worn on the shoulders of the user 12. The self-contained control/processing unit 154d may additionally include a power supply (which if head-worn, may take the form of a rechargeable or non-chargeable battery), a control panel with input/output functions, a display, and memory. Alternatively, power may be provided to the self-contained control/processing unit 154d wirelessly (e.g., by induction).

Figure 17:
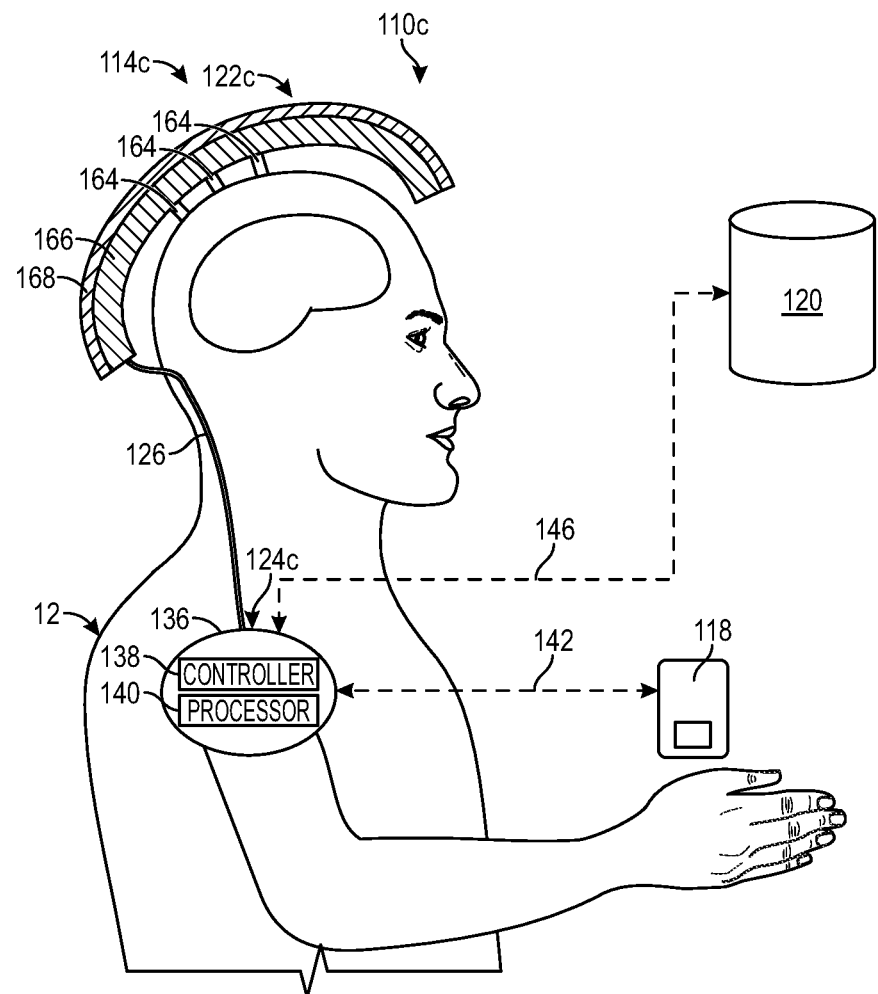
FIG. 17 is a view of still another specific physical embodiment of the neurome training system of FIGS. 1-10, the neurome training/brain emulation system of FIG. 12A-12B, or the neurome training/brain emulation system of FIG. 13.

Referring to FIG. 17, a physical implementation of still another embodiment of a system 100c that may embody the neurome training system 10 illustrated in FIGS. 1-10, the neurome training/brain emulation system 100 illustrated in FIGS. 12A-12B, or the neurome training/brain emulation system 100' illustrated in FIG. 13 will now be described.

The neurome training/brain emulation system 110c comprises a magnetically-based non-invasive brain interface assembly 114a configured for magnetically detecting neural activity in the brain 14 of the user 12. Example techniques of using the magnetically-based non-invasive brain interface assembly 114a are directed to the area of magnetic field measurement systems including systems for magnetoencephalography (MEG). The non-invasive brain interface assembly 114a may, e.g., incorporate any one or more of the neural activity detection technologies described in U.S. Pat. No. 16,428,871, entitled "Magnetic Field Measurement Systems and Methods of Making and Using," U.S. patent application Ser. No. 16/418,478, entitled "Magnetic Field Measurement System and Method of Using Variable Dynamic Range Optical Magnetometers", U.S. patent application Ser. No. 16/418,500, entitled, "Integrated Gas Cell and Optical Components for Atomic Magnetometry and Methods for Making and Using," U.S. patent application Ser. No. 16/457,655, entitled "Magnetic Field Shaping Components for Magnetic Field Measurement Systems and Methods for Making and Using," U.S. patent application Ser. No. 16/213,980, entitled "Systems and Methods Including Multi-Mode Operation of Optically Pumped Magnetometer(S)," (now U.S. Pat. No. 10,627,460), U.S. patent application Ser. No. 16/456,975, entitled "Dynamic Magnetic Shielding and Beamforming Using Ferrofluid for Compact Magnetoencephalography (MEG)," U.S. patent application Ser. No. 16/752,393, entitled "Neural Feedback Loop Filters for Enhanced Dynamic Range Magnetoencephalography (MEG) Systems and Methods," U.S. patent application Ser. No. 16/741,593, entitled "Magnetic Field Measurement System with Amplitude-Selective Magnetic Shield," U.S. patent application Ser. No. 16/820,131, entitled "Integrated Magnetometer Arrays for Magnetoencephalography (MEG) Detection Systems and Methods," U.S. patent application Ser. No. 16/850,380, entitled "Systems and Methods for Suppression of Interferences in Magnetoencephalography (MEG) and Other Magnetometer Measurements," U.S. patent application Ser. No. 16/850,444 entitled "Compact Optically Pumped Magnetometers with Pump and Probe Configuration and Systems and Methods," U.S. Provisional Application Ser. No. 62/842,818 entitled "Active Shield Arrays for Magnetoencephalography (MEG)," U.S. patent application Ser. No. 16/928,810 entitled "Systems and Methods for Frequency and Wide-Band Tagging of Magnetoencephalography (MEG) Signals," U.S. patent application Ser. No. 16/984,720 entitled "Systems and Methods for Multiplexed or Interleaved Operation of Magnetometers," U.S. patent application Ser. No. 16/984,752 entitled "Systems and Methods having an Optical Magnetometer Array with Beam Splitters," U.S. patent application Ser. No. 17/004,507 entitled "Methods and Systems for Fast Field Zeroing for Magnetoencephalography (MEG)," U.S. patent application Ser. No. 16/862,826 entitled "Single Controller for Wearable Sensor Unit that Includes an Array Of Magnetometers," U.S. patent application Ser. No. 16/862,856 entitled "Systems and Methods for Measuring Current Output By a Photodetector of a Wearable Sensor Unit that Includes One or More Magnetometers," U.S. patent application Ser. No. 16/862,879 entitled "Interface Configurations for a Wearable Sensor Unit that Includes One or More Magnetometers," U.S. patent application Ser. No. 16/862,901 entitled "Systems and Methods for Concentrating Alkali Metal Within a Vapor Cell of a Magnetometer Away from a Transit Path of Light," U.S. patent application Ser. No. 16/862,919 entitled "Magnetic Field Generator for a Magnetic Field Measurement System," U.S. patent application Ser. No. 16/862,946 entitled "Magnetic Field Generator for a Magnetic Field Measurement System," U.S. patent application Ser. No. 16/862,973 entitled "Magnetic Field Measurement Systems Including a Plurality of Wearable Sensor Units Having a Magnetic Field Generator," U.S. Provisional Application Ser. No. 62/975,709 entitled "Self-Calibration of Flux Gate Offset and Gain Drift To Improve Measurement Accuracy of Magnetic Fields from the Brain Using a Wearable System," U.S. Provisional Application Ser. No. 62/975,693 entitled "Nested and Parallel Feedback Control Loops for Ultra-Fine Measurements of Magnetic Fields from the Brain Using a Wearable MEG System," U.S. Provisional Application Ser. No. 62/975,719 entitled "Estimating the Magnetic Field at Distances from Direct Measurements to Enable Fine Sensors to Measure the Magnetic Field from the Brain Using a Wearable System," U.S. Provisional Application Ser. No. 62/975,723 entitled "Algorithms that Exploit Maxwell's Equations and Geometry to Reduce Noise for Ultra-Fine Measurements of Magnetic Fields from the Brain Using a Wearable MEG System," U.S. Provisional Application Ser. No. 62/975,727 entitled "Optimal Methods to Feedback Control and Estimate Magnetic Fields to Enable a Wearable System to Measure Magnetic Fields from the Brain," U.S. Provisional Application Ser. No. 62/983,406 entitled "Two Level Magnetic Shielding of Magnetometers," U.S. Provisional Application Ser. No. 63/076,015 entitled "Systems and Methods for Recording Neural Activity," U.S. Provisional Application Ser. No. 63/058,616 entitled "OPM Module Assembly with Alignment and Mounting Components as Used in a Variety of Headgear Arrangements," U.S. Provisional Application Ser. No. 63/076,880 entitled "Systems and Methods for Multimodal Pose and Motion Tracking for Magnetic Field Measurement Or Recording Systems," U.S. Provisional Application Ser. No. 63/140,150 entitled "Magnetic Field Measurement or Recording Systems with Validation Using Optical Tracking Data," and U.S. Provisional Application Ser. No. 63/135,364 entitled "Devices, Systems, and Methods with Optical Pumping Magnetometers for Three-Axis Magnetic Field Sensing," which are all expressly incorporated herein by reference in their entirety.

The brain interface assembly 114c includes a magnetoencephalography (MEG) head-worn unit 122c that is configured for being applied to the user 12, and in this case, worn on the head of the user 12; and an auxiliary non-head-worn unit 124c (e.g., worn on the neck, shoulders, chest, or arm). Alternatively, the functionality of the unit 124c may be incorporated into the head-worn unit 122c, as described below. The auxiliary non-head-worn unit 124c may be coupled to the head-worn unit 122c via a wired connection 126 (e.g., electrical wires). Alternatively, the brain interface assembly 114c may use a non-wired connection (e.g., wireless radio frequency (RF) signals (e.g., Bluetooth, Wifi, cellular, etc.) or optical links (e.g., fiber optic or infrared (IR)) for providing power to or communicating between the respective head-worn unit 122c and the auxiliary unit 124c.

The head-worn unit 122c includes a plurality of optically pumped magnetometers (OPMs) 164 or other suitable magnetometers to measure biologically generated magnetic fields from the brain of the user 12 and a passive shield 166 (and/or flux concentrators). By placing the passive shield 166 over the head of the user 12, the ambient background magnetic field arising from areas outside the passive shield 166 is greatly decreased and the OPMs 164 can measure or detect magnetic fields from activity occurring in the brain of the user 12 due to the reduction in the ambient background magnetic field.

An OPM is an optical magnetometry system used to detect a magnetic field that propagates through the human head. Optical magnetometry can include the use of optical methods to measure a magnetic field with very high accuracy—on the order of $1 \times 10^{-15}$ Tesla. Of particular interest for their high-sensitivity, an OPM can be used in optical magnetometry to measure weak magnetic fields. (The Earth's magnetic field is typically around 50 micro Tesla). In at least some systems, the OPM has an alkali vapor gas cell that contains alkali metal atoms in a combination of gas, liquid, or solid states (depending on temperature). The gas cell may contain a quenching gas, buffer gas, or specialized anti-relaxation coatings or any combination thereof. The size of the gas cells can vary from a fraction of a millimeter up to several centimeters, allowing the practicality of OPMs to be used with wearable non-invasive brain interface devices.

The head-worn unit 122c further comprises a support housing structure 168 containing the OPMs 164, passive shield 166, and other electronic or magnetic components. As will be described in further detail below, the support housing structure 168 may be shaped, e.g., have a banana, headband, cap, helmet, beanie, other hat shape, or other shape adjustable and conformable to the user's head, such that the OPMs 164 are in close contact with the outer skin of the head, and in this case, the scalp of the user 12. The support housing structure 168 may be made out of any suitable cloth, soft polymer, plastic, hard shell, and/or any other suitable material as may serve a particular implementation.

The head-worn unit 122c may also include a plurality of optically pumped magnetometer (OPM) modular assemblies, which OPM modular assemblies are enclosed within the head-worn unit 122c. The OPM modular assembly is designed to enclose the elements of the OPM optics, vapor cell, and detectors in a compact arrangement that can be positioned close to the head of the human subject. The head-worn unit 122c may also include an adjustment mechanism used for adjusting the head-worn unit 122c to conform with the human subject's head. These exemplary OPM modular assemblies and systems are described in more detail in U.S. Provisional Application No. 63/058,616, previously incorporated by reference. The magnetically-based head-worn unit 122c can also be used in a magnetically shielded environment with an open entryway which can allow for user movement as described for example in U.S. Provisional Application Ser. No. 63/076,015, previously incorporated by reference. User tracking movement in a magnetically shielded environment can include an optical user pose identification system and/or other sensing modalities as described more fully in U.S. Provisional Application Ser. Nos. 63/076,880 and 63/135,364, previously incorporated herein by reference.

The auxiliary unit 124c comprises the housing 136 containing the controller 138 and the processor 140. The controller 138 is configured for controlling the operational functions of the head-worn unit 122c, whereas the processor 140 is configured for processing the magnetic fields detected by the head-worn unit 122c to detect and localize the detected neural activity 24 of the user 12, as well as to determine the mental state of the user 12 based on the detected neural activity 24 of the user 12 if not performed by other processing units in the neurome training system 110c. The auxiliary unit 124c may additionally include a power supply (which if head-worn, may take the form of a rechargeable or non-chargeable battery), a control panel with input/output functions, a display, and memory. Alternatively, power may be provided to the auxiliary unit 124c wirelessly (e.g., by induction).

The neurome training/brain emulation system 110c further comprises the peripheral device 118 and the database, server, or cloud structure 120, which can function and be coupled to each other in the same manner described above with respect to the neurome training/brain emulation system 110a.

Figure 18A:
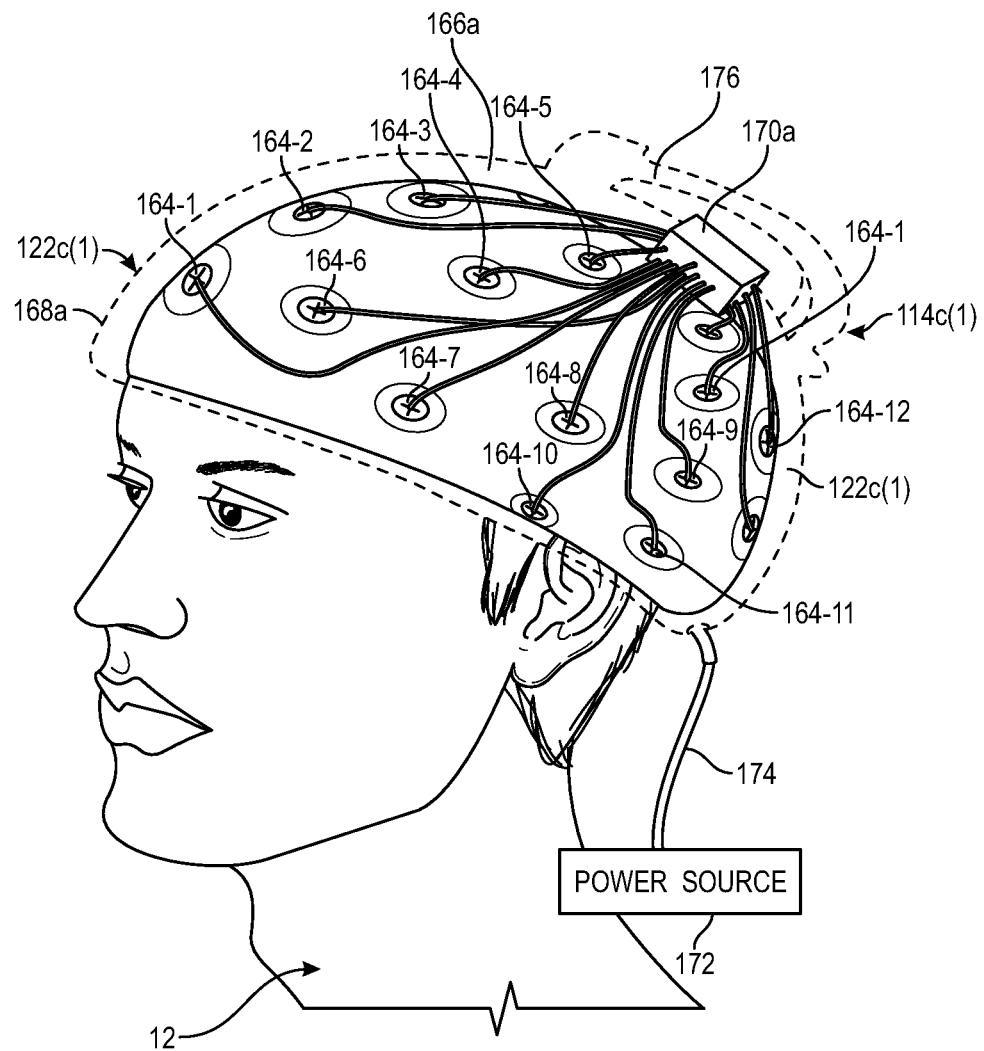
FIGS. 18A-18C illustrate exemplary non-invasive wearable devices as used with the system of FIG. 17.
Figure 18B:
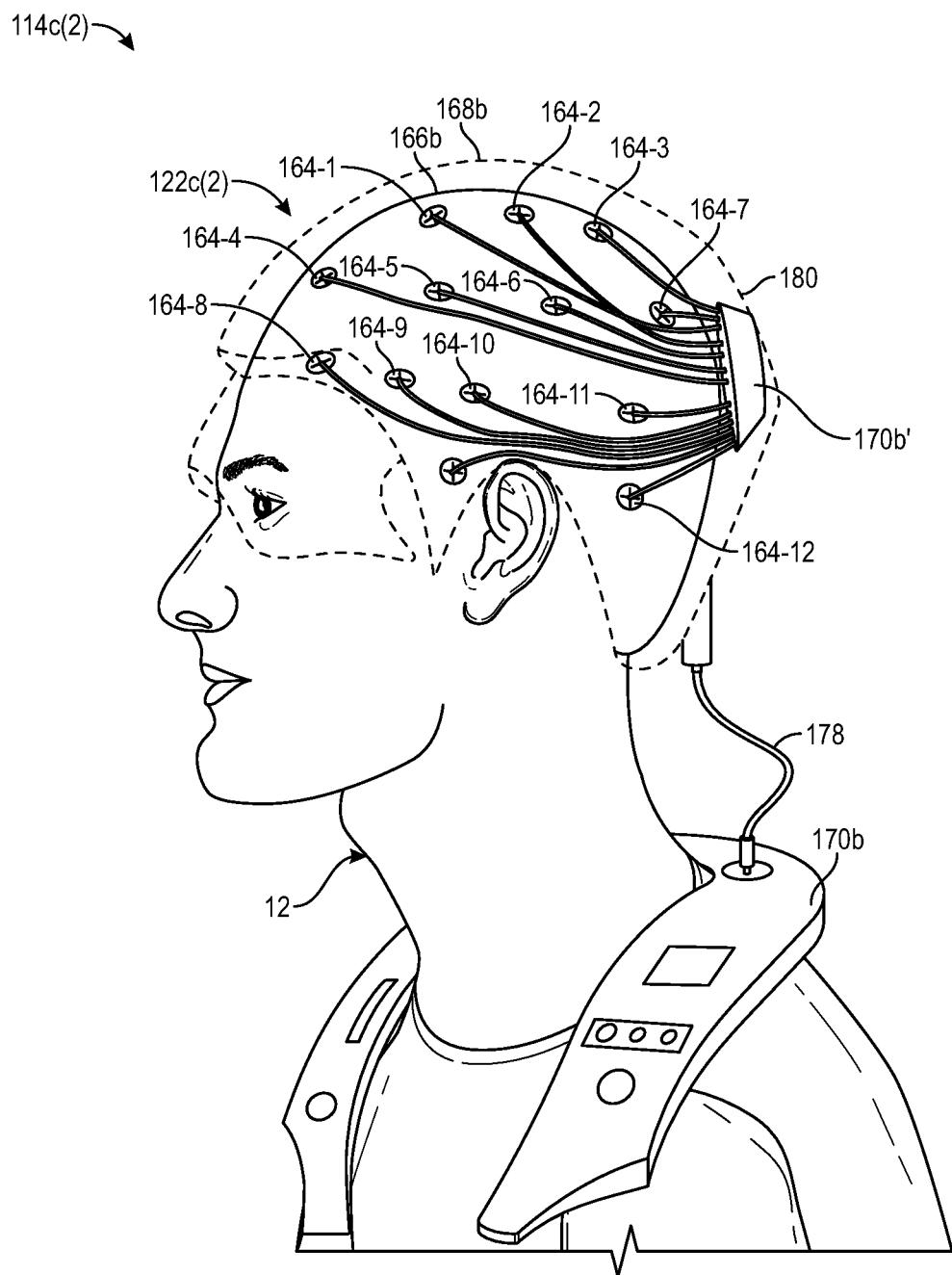
Figure 18C:
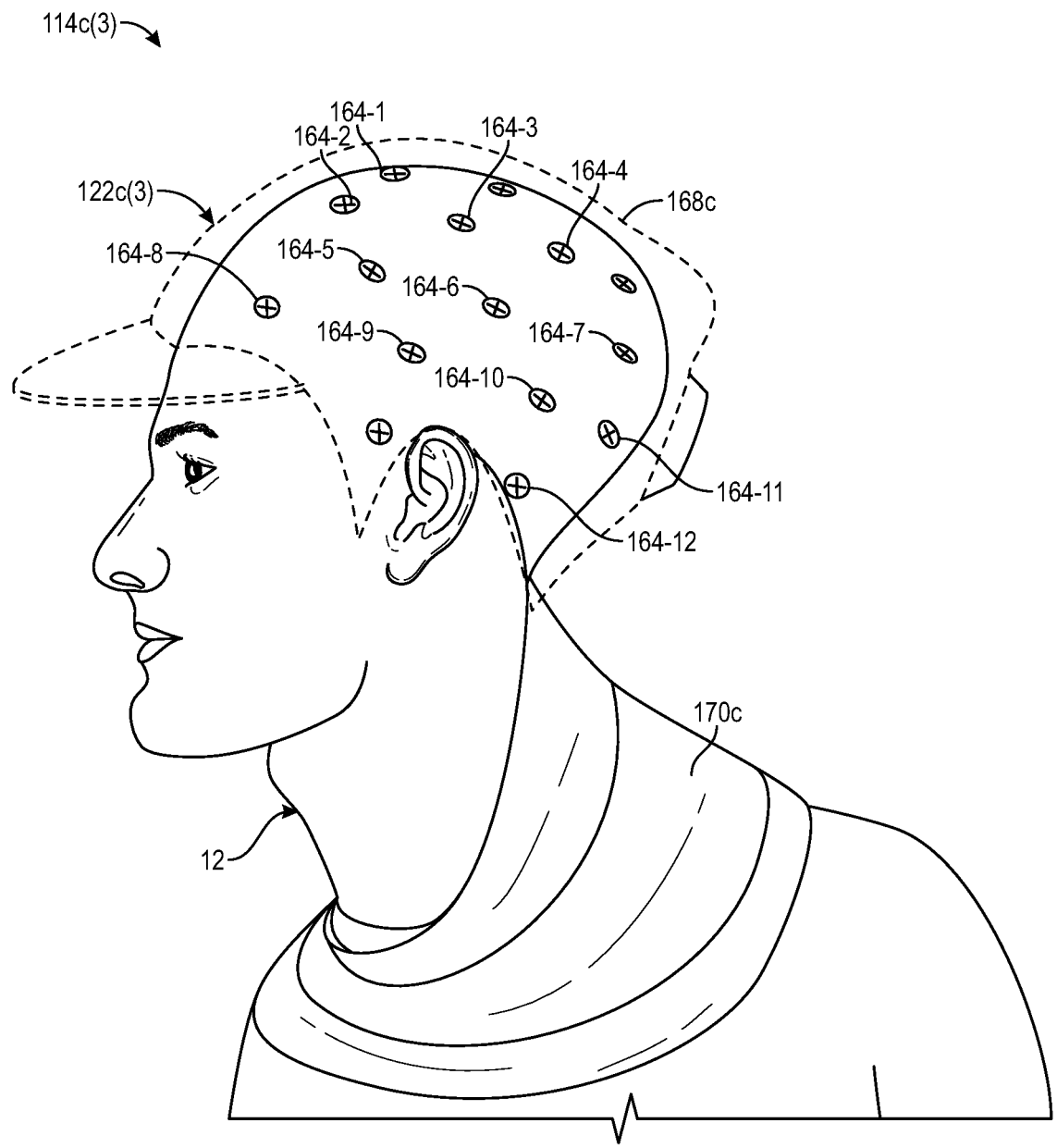

Referring now to FIGS. 18A-18C, different embodiments of the brain interface assembly 114c will be described. Such brain interface assemblies 114c may communicate wirelessly or via wire with the peripheral device 118 and database, server, cloud structure 120, as described above. Each of the brain interface assemblies 114c described below comprises a head-worn unit 122c having a plurality of OPMs 164, a passive shield 166, and a support housing structure 168 in which the OPMs 164 and passive shield 166 are embedded. Each of brain interface assemblies 114c may also comprise a control/processing unit 170 for controlling the operational functions of the OPMs 164, and processing the magnetic fields detected by the OPMs 164 to detect and localize the brain activity of the user 12. As will be described in further detail below, the control/processing unit 170 may be contained in the head-worn unit 122c or may be incorporated into a self-contained auxiliary unit. As will be set forth below, the support housing structure 168 may be shaped, e.g., have a banana, headband, cap, helmet, beanie, other hat shape, or other shape adjustable and conformable to the user's head, such that the OPMs 164 are in close contact with the outer skin of the head, and in this case, the scalp of the user 12.

As shown in FIG. 18A, a brain interface assembly 114c(1) comprises a head-worn unit 122c(1) and a power source 172 coupled to the head-worn unit 122c(1) via a wired connection 174. The head-worn unit 122c(1) includes the OPMs 164 (shown as 164-1 through 164-12) and a control/processing unit 170a. The head-worn unit 122c(1) further includes a support housing structure 168a that takes a form of a helmet that contains the OPMs 164, passive shield 166, and control/processing unit 170a. The material for the helmet 168a may be selected out of any suitable cloth, soft polymer, plastic, hard shell, and/or any other suitable material as may serve a particular implementation. The power source 172 may be implemented by a battery and/or any other type of power source configured to provide operating power to the OPMs 64, control/processing unit 170a, and any other component included within the brain interface assembly 122c(1) via the wired connection 174. The head-worn unit 122c(1) optionally includes a handle 176 affixed to the helmet 168a for providing a convenient means of carrying the head-worn unit 122c(1).

As shown in FIG. 18B, a brain interface assembly 114c(2) comprises a head-worn unit 122c(2) and a control/processing unit 170b coupled to the head-worn unit 122b(2) via a wired connection 178. The head-worn unit 122c(2) includes the OPMs 164 (shown as 164-1 through 164-12), and a support housing structure 168b that takes a form of a helmet that contains the OPMs 164 and passive shield 166. The material for the helmet 168b may be selected out of any suitable cloth, soft polymer, plastic, hard shell, and/or any other suitable material as may serve a particular implementation. Unlike the control/processing unit 170a of the brain interface assembly 114c(1) illustrated in FIG. 18A, which is contained in the head-worn unit 122c(1), the control/processing unit 170b is self-contained, and may take the form of a garment (e.g., a vest, partial vest, or harness) for being worn on the shoulders of the user 12. The self-contained control/processing unit 170b may additionally include a power supply (which if head-worn, may take the form of a rechargeable or non-chargeable battery), a control panel with input/output functions, a display, and memory. Alternatively, power may be provided to the self-contained control/processing unit 170b wirelessly (e.g., by induction). The head-worn unit 122c(1) optionally includes a crest or other protrusion 180 formed in the helmet 168b for providing means of carrying a control/processing unit 170b'.

As shown in FIG. 18C, a brain interface assembly 114c(3) comprises a head-worn unit 122c(3) and a control/processing unit 170c. The head-worn unit 122c(3) includes the OPMs 164 (shown as 164-1 through 164-12), and a support housing structure 168c that takes a form of a baseball cap that contains the OPMs 164 and passive shield 166. The material for baseball cap 168c may be selected out of any suitable cloth, soft polymer, plastic, hard shell, and/or any other suitable material as may serve a particular implementation. The control/processing unit 170c is self-contained, and may take the form of a garment (e.g., scarf) for being worn around the neck of the user 12. The self-contained control/processing unit 170c may additionally include a power supply (which if head-worn, may take the form of a rechargeable or non-chargeable battery), a control panel with input/output functions, a display, and memory. Alternatively, power may be provided to the self-contained control/processing unit 170c wirelessly (e.g., by induction).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of training a neurome that emulates a brain of a user, comprising:
   storing a neurome comprising a brain state regression model;
   peripherally inputting analog instances of a plurality of stimuli into the brain of the user from at least one source of content;
   detecting neural activity of the user in response to the analog instances of the plurality of stimuli peripherally input into the brain of the user;
   determining a plurality of brain states of the user based on the detected neural activity of the user;
   inputting digital instances of the plurality of stimuli into the neurome, such that the neurome outputs a plurality of determined brain states of an avatar; and
   modifying the neurome based on the plurality of determined brain states of the avatar and the plurality of determined brain states of the user by:
      extracting single-dimensional vectors of content features from the digital instances of the plurality of stimuli characterizing the at least one source of content;
      inputting the single-dimensional vectors of content features into a first input of the brain state regression model;
      inputting single-dimensional vectors of brain state features characterizing the determined brain states of the user into a second input of the brain state regression model, such that the brain state regression model outputs single-dimensional vectors of brain state features of the avatar that substantially match the single-dimensional vectors of brain state features of the user.

2. The method of claim 1, further comprising detecting peripheral physiological activity of the user in response to the analog instances of the plurality of stimuli peripherally input into the brain of the user from the at least one source of content, wherein the neurome is modified further based on the detected peripheral physiological activity.

3. The method of claim 1, further comprising acquiring a personal profile of the user, wherein the neurome is modified further based on the acquired personal profile.

4. The method of claim 3, wherein the personal profile comprises one or more of an internet browsing history of the user, a reading history of the user, and autobiographical information of the user.

5. The method of claim 1, wherein at least some of the plurality of different brain states of the user are different from each other, and at least some of the plurality of determined brain states of the avatar are different from each other.

6. The method of claim 1, wherein the plurality of determined brain states of the user comprises a plurality of physiological brain states of the user, and the plurality of brain state of the avatar comprises a plurality of physiological brain states of the avatar.

7. The method of claim 6, wherein the detected neural activity of the user comprises multi-dimensional time series of neural data, the method further comprising extracting brain state features from the time series of neural data characterizing the plurality of determined brain states of the user, wherein the neurome is modified based on the plurality of determined brain states of the avatar and the extracted brain state features characterizing the plurality of determined brain states of the user.

8. The method of claim 6, further comprising acquiring a plurality of mental brain states of the user in response to the analog instances of the plurality of stimuli peripherally input into the brain of the user from the at least one source of content, wherein the neurome is modified based on the plurality of determined mental brain states of the user.

9. The method of claim 8, further comprising correlating the plurality of acquired mental brain states of the user respectively to the plurality of determined physiological mental brain states of the user, wherein the neurome is modified based on the plurality of acquired mental brain states by storing the correlated plurality of acquired mental brain states of the user respectively and plurality of determined physiological mental brain states of the user in the neurome.

10. The method of claim 9, further comprising acquiring conscious input from the user indicating the plurality of mental brain states of the user in response to the plurality of analog stimulus instances, wherein the plurality of mental brain states of the user are acquired from the acquired conscious input of the user.

11. The method of claim 1, wherein the plurality of determined brain states of the user comprises a plurality of mental brain states of the user, and the plurality of brain states of the avatar comprises a plurality of mental brain states of the avatar.

12. The method of claim 11, further comprising determining a plurality of physiological brain states of the user based on the detected neural activity of the user, wherein the plurality of mental states of the user are determined based on the plurality of determined physiological brain states of the user.

13. The method of claim 1, further comprising extracting content features from the digital instances of the plurality of stimuli characterizing the at least one source of content, wherein the plurality of determined brain states of the avatar are determined based on the extracted content features.

14. The method of claim 1, wherein the brain state regression model comprises a deep neural network.

15. The method of claim 1, further comprising generating the digital instances of the plurality of stimuli.

16. The method of claim 15, wherein the at least one source of content is at least one real-world source of content, the method further comprising acquiring the analog instances of the plurality of stimuli from the at least one real-world source of content, wherein the digital instances of the plurality of stimuli are generated based on the acquired analog instances of the plurality of stimuli.

17. The method of claim 16, wherein generating the digital instances of the plurality of stimuli comprises digitizing the acquired analog instances of the plurality of stimuli.

18. The method of claim 16, further comprising:
identifying the acquired analog instances of the plurality of stimuli;
acquiring at least one virtual source of content; and
wherein the digital instances of the plurality of stimuli are generated from the acquired at least one virtual source of content that characterizes the acquired analog instances of the plurality of stimuli.

19. The method of claim 16, further comprising:
acquiring at least one virtual source of content, wherein the digital instances of the plurality of stimuli are generated from the acquired at least one virtual source of content; and
generating the analog instances of the plurality of stimuli from the generated digital instances of the plurality of stimuli.

20. The method of claim 19, further comprising selecting or modifying the at least one virtual source of content based on the plurality of determined brain states of the user.

21. The method of claim 20, further comprising generating meta data characterizing the plurality of stimuli;
logging the determined brain states of the user and the acquired meta data, wherein the at least one virtual source of content is selected or modified based on the logged determined brain states of the user and the acquired meta data.

22. The method of claim 15, further comprising:
generating meta data characterizing the plurality of stimuli, wherein the neurome comprises a plurality of brain state models; and
selecting one of the brain state models based on the generated meta data, wherein the neurome is modified by modifying the selected brain state model based on the plurality of determined brain states of the user and the plurality of determined brain states of the avatar.

23. The method of claim 16, further comprising modulating the analog instances of the plurality of stimuli, such that the modulated analog instances of the plurality of stimuli are peripherally input into the brain of the user.

24. The method of claim 1, wherein the plurality of stimuli comprises a first plurality of different stimuli, and wherein the plurality of determined brain states of the avatar comprises a plurality of different determined brain states of the avatar.

25. The method of claim 24, wherein the at least one source of content comprises a first plurality of different sources of content.

26. The method of claim 25, wherein the first plurality of different sources of content are all in the same genre.

27. The method of claim 26, wherein the same genre of the first plurality of different sources of content is selected from one of a genre of movies, a genre of songs, a genre of books, a genre of household appliances, a genre of automobiles, a genre of foods, a genre of drinks, a genre of artwork, and sources of consumable chemical substances.

28. The method of claim 24, further comprising:
generating at least one digital instance of at least one stimulus from at least one source of content different than any of the first plurality of different sources of content; and
inputting the at least one digital instance of the at least one stimulus into the neurome, such that the neurome outputs at least one determined brain state of the avatar predictive of at least one brain state of the user if at least one analog instance of the at least one stimulus had been peripherally input into the brain of the user.

29. The method of claim 28, wherein the at least one different source of content is in the same genre as the first plurality of different sources of content.

30. The method of claim 28, further comprising:
processing the at least one determined brain state of the avatar;
generating a practical result based on the at least one processed brain state of the avatar; and
outputting the practical result to the user.

31. The method of claim 30,
wherein generating the at least one digital instance of the at least one stimulus comprises generating digital instances of a second plurality of different stimuli from a second plurality of different sources of content, at least some of which are different from the first plurality of different sources of content; and
wherein inputting the at least one digital instance of the least one stimulus into the neurome comprises inputting the digital instances of the second plurality of different stimuli into the neurome, such that the neurome outputs a plurality of determined brain states of the avatar predictive of a plurality of brain states of the user if an analog instance of the each of the plurality of different stimuli had been peripherally input into the brain of the user; and
wherein generating the practical result comprises downselecting the second plurality of different sources of content.

32. The method of claim 31, further comprising selecting or modifying the second plurality of different sources of content based on the practical result.

33. The method of claim 31, wherein the first plurality of different sources of content and the second plurality of different sources of content are associated with a plurality of different products or services.

* * * * *